US006325475B1

(12) United States Patent
Hayes et al.

(10) Patent No.: US 6,325,475 B1
(45) Date of Patent: Dec. 4, 2001

(54) DEVICES FOR PRESENTING AIRBORNE MATERIALS TO THE NOSE

(75) Inventors: Donald J. Hayes, Plano; Christopher J. Frederickson, Little Elm; David B. Wallace, Dallas, all of TX (US)

(73) Assignee: Microfab Technologies Inc., Plano, TX (US)

( * ) Notice: Subject to any disclaimer, the term of this patent is extended or adjusted under 35 U.S.C. 154(b) by 0 days.

(21) Appl. No.: 08/837,646

(22) Filed: Apr. 21, 1997

Related U.S. Application Data

(60) Provisional application No. 60/025,526, filed on Sep. 6, 1996.

(51) Int. Cl.[7] ............. B41J 3/00; A61M 16/00; A61M 1/00; A61K 51/00
(52) U.S. Cl. ............. 347/2; 604/28; 424/1.13; 128/203.11
(58) Field of Search ............. 347/2, 83; 604/28; 424/1.13; 702/45; 222/160; 128/203.11, 203.12, 200.14

(56) References Cited

U.S. PATENT DOCUMENTS

| | | | |
|---|---|---|---|
| 3,683,212 | 8/1972 | Zoltan | 310/8.3 |
| 3,857,049 | 12/1974 | Zoltan | 310/8.1 |
| 4,159,672 | 7/1979 | Garguilo et al. | |
| 4,265,248 | * 5/1981 | Chuiton et al. | 128/630 |
| 4,310,474 | 1/1982 | Iyengar | |
| 4,380,018 | * 4/1983 | Andoh | 346/140 |
| 4,418,354 | 11/1983 | Perduijn | 346/140 R |
| 4,812,856 | * 3/1989 | Wallace | 346/1.1 |
| 4,887,100 | 12/1989 | Michaelis et al. | 346/140 R |
| 5,053,100 | 10/1991 | Hayes et al. | 156/294 |
| 5,229,016 | * 7/1993 | Hayes et al. | 222/590 |
| 5,365,645 | 11/1994 | Walker et al. | 29/25.35 |
| 5,400,064 | 3/1995 | Pies et al. | 347/68 |
| 5,426,455 | 6/1995 | Williamson et al. | 347/10 |
| 5,436,648 | 7/1995 | Storz et al. | 347/10 |
| 5,508,200 | * 4/1996 | Tiffany et al. | 436/44 |
| 5,565,148 | * 10/1996 | Pendergrass, Jr. | 261/30 |
| 5,591,409 | * 1/1997 | Watkins | 422/110 |
| 5,849,208 | * 12/1998 | Hayes et al. | 216/94 |
| 5,894,841 | 4/1999 | Voges | |
| 5,904,916 | * 5/1999 | Hirsch | 424/45 |

FOREIGN PATENT DOCUMENTS

B-70632/94 * 4/1997 (AU).

OTHER PUBLICATIONS

Cain, W.S., Cometto–Muniz, J.E. and Wijk, R.A. (1992) Techniques in the quantitative study of human olfaction. In M.J. Serby and K.L. Chobor (eds.) *Science of Olfaction*. Springer, NY, 279–308.

* cited by examiner

Primary Examiner—John Barlow
Assistant Examiner—An H. Do
(74) *Attorney, Agent, or Firm*—Locke Liddell & Sapp LLP

(57) ABSTRACT

An ink-jet dispenser for the micro-dispensation of airborne materials into an individual's airspace for inhalation or sniffing. The ink-jet dispenser will allow the study of temporal integration times, inter-nostril summation, backwards and forwards masking, and other olfactory phenomena.

46 Claims, 25 Drawing Sheets

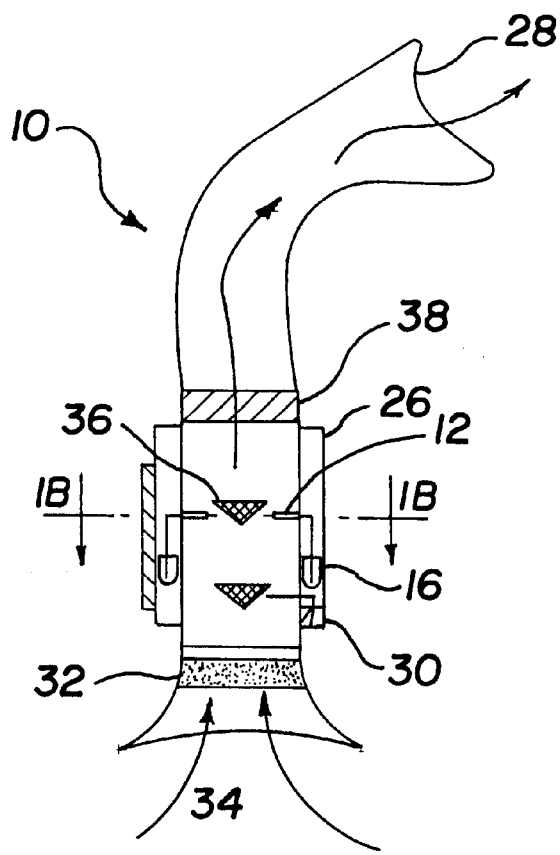
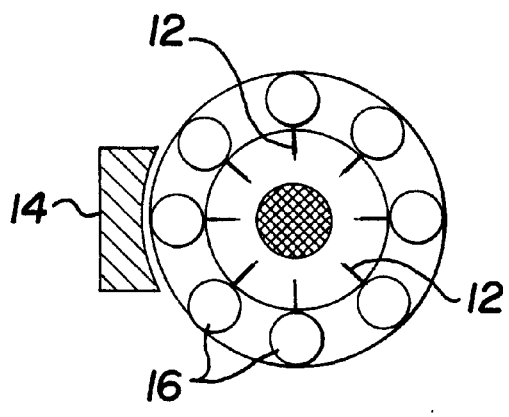
Fig. 1B
Fig. 1A
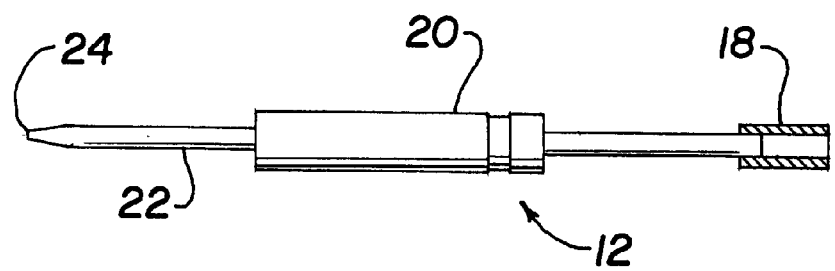
Fig. 1C

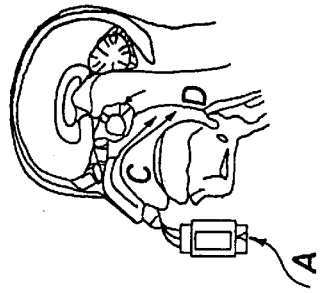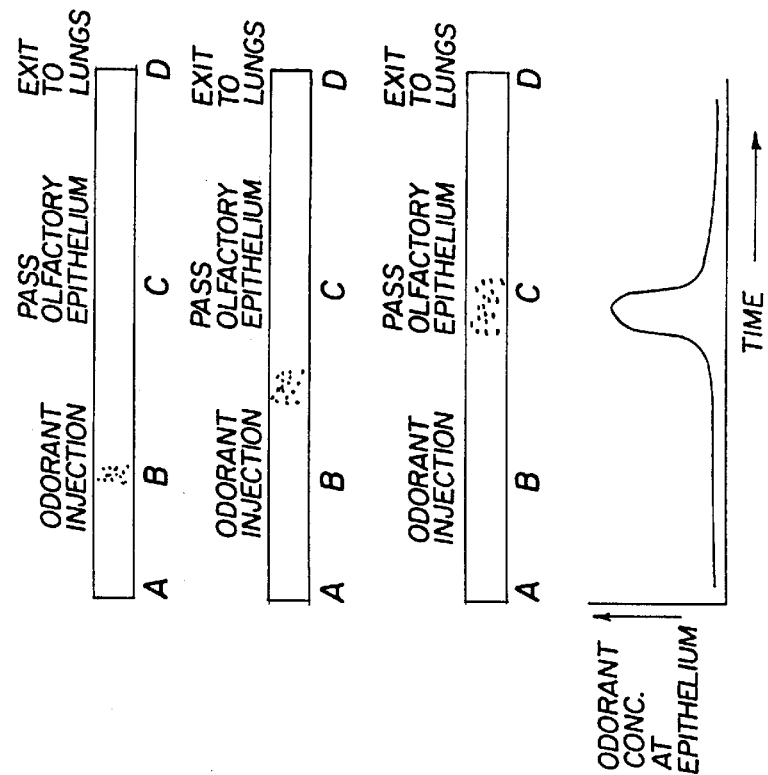
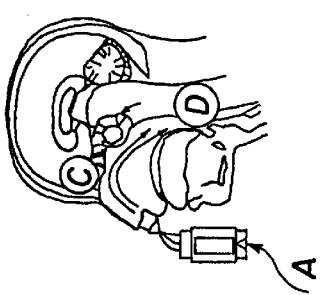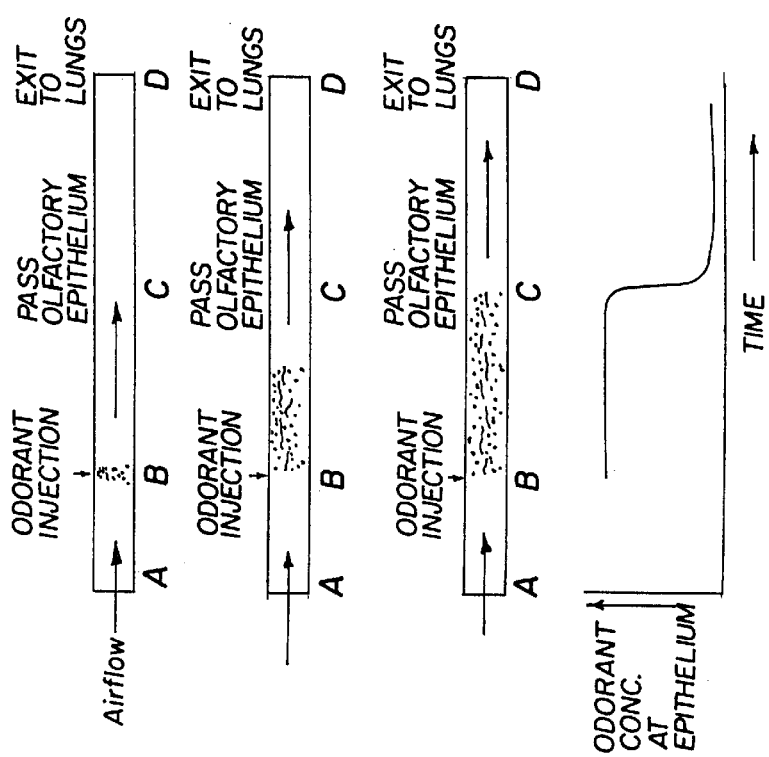
Fig. 22

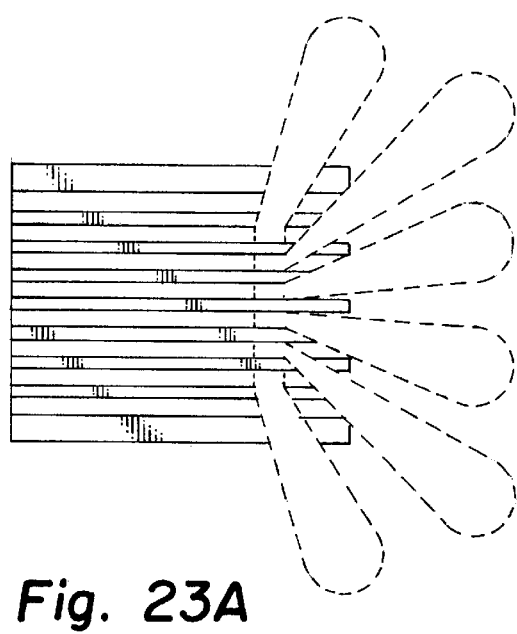
Fig. 23A
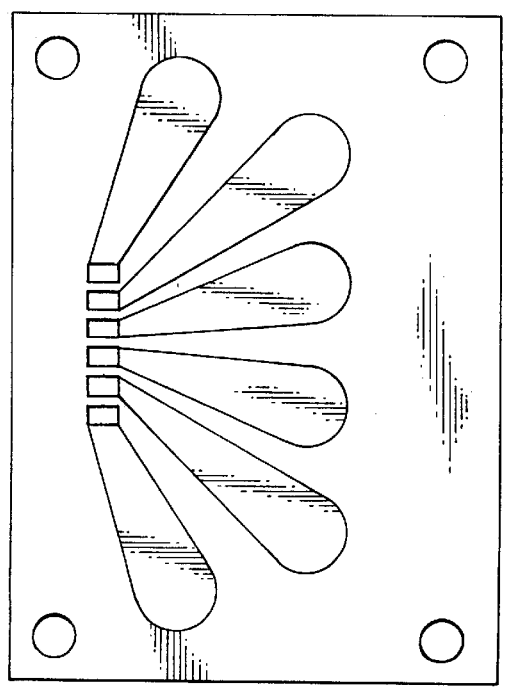 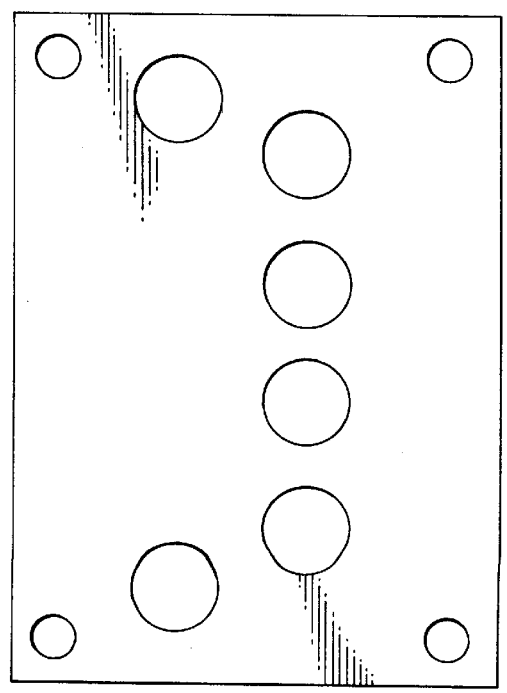
Fig. 23B          Fig. 23C

DEVICES FOR PRESENTING AIRBORNE MATERIALS TO THE NOSE

CROSS-REFERENCE TO RELATED APPLICATIONS

This application is a continuation-in-part of provisional patent application No. 60/025,526 filed by the same inventors Sep. 6, 1996 for which priority is claimed under 35 U.S.C. §119e.

BACKGROUND OF THE INVENTION

1. Field of the Invention

The present invention relates in general to the use of ink-jet technology to microdispense airborne materials into an individual's airspace for inhalation or sniffing.

2. Description of the Related Art

A. Purpose of the Invention

Nasal delivery of airborne materials is a vital input pathway to any organism, including human beings. Three aspects of nasal delivery are important: (1) Olfactory sensory cells have axons going directly into the central nervous system, and materials introduced into their cytoplasm via transmembrane uptake in the airway therefore have direct access to the "brain" side of the "blood-brain-barrier," via anterograde transport within the cells; (2) inhalation is the most direct route of drug delivery to the brain, because the blood returning from the lungs goes directly (via the right atrium and ventricle) to the ascending aorta, delivering an oxygen-rich (and drug-rich) bolus of blood to the brain; (3) the olfactory sense is of unique importance in controlling behavior, including the behaviors of eating, drinking, and vital social behaviors such as bonding, reproduction, and aggression.

For all three of the purposes described above, the precise, digital, interactive, controlled delivery of airborne materials into the nasal airways by solid-state chip-based ink-jet dispensing technology would be a vital and powerful new technique.

Another purpose of the invention is to deliver fragrances into the personal airspace and/or inspired airstream of people engaged in various kinds of entertainment, training or simulation using virtual reality (VR). VR has become a premiere tool for training and performance testing. The power of VR techniques, however, depends heavily upon the illusion of "being there," or a sense of "presence." When the sense of presence is strong and a subject is deeply immersed in the illusory environment, the subject begins to feel, act and think as if the situation were real. In the case of synthetic battlefield simulation and training, odors are often the very cues that a soldier/trainee needs to recognize in the emergency situations for which VR training and simulation is most useful. Indeed, some efforts have been made to add smells like leaking jet fuel and melting electrical wires to pilot and firefighter VR training. Direct digital control of odor presentation would be an asset in the VR application.

B. Related Art i. Alternative Methods of Drug Delivery

Drug delivery via the nasal or oral air passages is presently done with (a) hand-held, spray-atomizer inhalers, (b) table-top "vaporizer" type systems, (c) by application of volatile substances on the chest, or (d) (for illicit and/or recreational materials) by inhalation of ignition products or direct application of material to the olfactory epithelium.

ii. Alternative Methods for Aesthetic Presentation

Delivery of odoriferous materials to the nose for aesthetic purposes is generally done by (a) spreading volatile and odoriferous materials on the skin, (b) spraying them into the air from cans or bottles, or (c) delivering them into the air by mounting bars, cakes, or open aliquots of the materials in containers that can be fixed to walls, ceilings, and fixtures of the target space.

iii. Alternative Methods for Psychophysics

Testing smell abilities (olfactory psychophysics) is currently done by one of the following three methods: (1) by means of an "olfactometer," which is the most precise method used, in which complex pumps, valves, and plumbing are used to produce controlled vapor concentrations which are then delivered to the nose for inhalation at controlled temperature, pressure, and flow rate; (2) presenting plastic bottles containing known concentrations of odoriferous materials for a "sniff" by the subject; and (3) by microencapsulating and dispersing odoriferous materials on a paper substrate for release by scratching the surface (scratch and sniff).

iv. Virtual Reality

Three alternative methods have been used for delivering odors to the VR environment: (1) a "smell bar" impregnated with fragrances that can be robotically moved into and out of a position beneath the VR client's nostrils; (2) a robotic "scratch and sniff" system that releases odors into the subject's airstream; and (3) a system using fluid vials of odorants and a fan with air-handling tubes to bring selected odors into the region of the subject's nasal air-space.

C. Uses for the Invention

Diagnosticians, clinical investigators, and basic scientists all need better olfactory test systems. For the clinician, the list of neurologic and neuropsychiatric diseases where olfactory tests can aid in diagnosis is substantial and growing. Olfactory cerebral evoked potentials are also gaining use in the clinic as a means of assessing fronto-limbic and hemispheric abnormalities. An ink-jet dispenser system would be a practical alternative to either the complex olfactometer or the simple squeeze- or scratch-and-sniff approaches. Indeed, the precision of an ink-jet system would provide many research capabilities that would go beyond the typical olfactometer.

Olfactory testing is a vital diagnostic tool in neurology, psychiatry, and neuropsychology. Indeed, there are literally dozens of disorders for which the presence of olfactory deficits is an aid to diagnosis. These disorders include major dementing brain diseases, such as Huntington's chorea, Alzheimer's disease, Down's syndrome, Parkinson's disease, and Picks disease, and a diversity of other conditions including epilepsy, migraine headaches, multiple sclerosis, Korsakov's syndrome, schizophrenia, and certain kinds of head trauma.

Olfactory tests hold the promise of early, presymptomatic diagnosis and differentiation among dementing and other mental diseases. With Parkinson's disease, several groups have found that olfactory testing allows early detection and discriminates among different palsy-disorder subtypes. In Alzheimer's disease, the olfactory deficits also emerge quite early, and correlate with measures such as the extent of CNS volumetric loss. The early appearance of histopathology in the peripheral and central olfactory pathways in Alzheimer's disease, Down's syndrome and certain Parkinson's disease patients are probably responsible for the early emergence of olfactory deficits in those disorders. Early detection of emerging Huntington's chorea symptomology is also favored by recent data.

In all VR settings, adding smells would greatly enhance the sense of presence. Adding odor to any VR system is a cost-effective way to increase operator immersion.

SUMMARY OF THE INVENTION

The present invention is directed to ink-jet-based systems for the micro-dispensation of airborne materials into the inspired airstream or personal airspace of a subject. Preferably the airborne materials are presented in the form of a drug, fragrance or a substance comprising a volatile component. The systems of the present invention have utility in various applications such as virtual reality simulators, instrumentation including medical instrumentation, conditioning of environments, fragrance synthesis and calibration of chemical detection systems.

The microdispensing ink-jet-based systems of the present invention allow the study of temporal integration times, inter-nostril summation, backwards and forwards masking, and other phenomena that have only received the most cursory of attention due to methodological limitations. The microdispensing ink-jet-based systems of the present invention permit precise control of both the temporal envelope of the stimulus and the total number of molecules constituting the stimulus. According to a preferred embodiment of the present invention, the microdispensing ink-jet-based system allows for the digital dispensing of airborne materials. According to another preferred embodiment of the present invention, the microdispensing ink-jet-based system includes dual dispensers on parallel air tubes the airstreams of which can be separate or mixed so as to give separate stimulation of the two olfactory epithelia or simultaneous stimulation of both epithelia. A scaled-down version of the device of the present invention can also be used with laboratory animals, including rats, with a miniature head-mounting (similar to standard rat EEG-telemetry systems) used to maintain the dispensing device in a fixed position relative to the head.

The microdispensing, ink-jet-based systems of the present invention will enable digital, discrete, punctate dispensing of airborne materials as micelles, molecules or droplets into the inspired airstream which will give a crisp, abrupt stimulus onset for event-related brain potential recording.

According to a preferred embodiment of the present invention, as many as several thousand specific odorants can be loaded in a single odor-chip and dispensed in a random-access format, which will allow the response of individual receptors, or microzones of the olfactory epithelium or vomeronasal organ to be characterized.

The digital microdispensing ink-jet-based systems of the present invention overcome the disadvantages and drawbacks of the existing olfactory test and sensory stimulation formats and is fully automatic, more convenient, faster, and much more precise. The devices of the present invention permit extensive and detailed psychophysical testing with virtually no instrumental system to maintain, in essentially any clinical office setting. Increasing the speed, precision, and practicality of the olfactory analytical method will lead to more sensitive and more discriminating presymptomatic tests for clinic use. As promising examples, it is worth noting that direct measurements of hippocampal and paraphippocampal degeneration in Alzheimer's disease by MRI have shown high correlations with olfactory performance on the relatively coarse-grained U. Penn. Smell Identification Test ("UPSIT"). With a finer-grained olfactory assessment as provided by the ink-jet-based systems of the present invention, the likelihood of detecting nascent degenerative changes early in the patient's history will be very high.

The present invention is directed to the use of ink-jet technology to microdispense airborne materials. According to a first preferred embodiment of the present invention, ink-jet type dispensers are used to microdispense picoliter sized droplets of airborne materials directly into the air.

According to a second preferred embodiment of the present invention, ink-jet type dispensers are used to dispense microdrops of drugs, fragrances or volatile component containing substances onto a chip, the volatile substances are encapsulated with a thin cover film, and bubble-jet type technology is used to burst the encapsulating film by rapid resistance heating of the fluid, thus dispensing airborne materials directly from the chip, on demand.

According to the first preferred embodiment of the present invention, the ink-jet type dispensers can be used as an analytical test instrument, or as an aesthetic/cosmetic device for olfactory conditioning of environments.

In the case of the analytical olfactometry instrument, the jets dispense directly onto controlled airflow channels which in turn present the airborne material-laden air directly to a subject's nose. The jet-based dispenser preferably has dozens of jets loaded with different drugs, fragrances or volatile component containing substances, allowing dose, timing and mixtures of olfactants to be controlled with digital, interactive, programmable ease.

In the case of environmental conditioning for aesthetic or cosmetic purposes, the volatile component containing substance-jets may be used to micro-dispense fragrant fluids from their reservoirs directly into the environmental air directly into air-handling ducts, filters, plenums, and similar devices for uniform dispersion of the airborne materials through the target environment. In the cab of a vehicle, for example, jets may be used to dispense airborne materials directly into the air circulation system. In a room, the jets may be used to dispense airborne materials into heating and air conditioning ducts, filters, or vents.

In still another preferred embodiment of the present invention, a further version of environmental dispensing involves the placement of jets on, in, or near the nose of a subject, using glasses frames, a microphone-headset frame, a helmet, or other supporting framework. The close positioning of the jets to the nose of a subject allows the subject's olfactory input to be privately manipulated.

According to the second preferred embodiment of the present invention, the delivery of drugs, fragrances or volatile component containing substances from a chip into which the aliquots of drugs, fragrances or volatile component containing substances have been previously printed and encapsulated has all of the applications as described above with respect to the first preferred embodiment. The difference between the two methods is that the chip can be preloaded with hundreds or thousands of different materials in as small as a millimeter-sized chip and can be stored for an indefinite shelf life, whereas the liquid-bearing ink-jet holds fewer different substances and is larger and more complex. The liquid-dispensing ink-jet design, however, may hold a larger volume of each substance, and thus is appropriate for applications requiring larger volumes of stimuli.

The devices of the present invention provide advantages over the prior art systems because ink-jet dispensing of airborne materials is precise, discrete, digital, programmable, and interactive. The speed and accuracy of the dispensing of airborne materials is several orders of magnitude better with ink-jet dispensing than can be obtained with any other method. Moreover, because the devices can be made exquisitely small, on the order of several hundred per linear inch, the size of the systems of the present invention can be reduced to a few cubic inches (for a jet-type) or a few cubic millimeters (for a chip-type device).

The olfactory stimulators of the present invention can be controlled by digital electronics thus making all types of digital, computer, and interactive control possible. With these systems, many different rates, intensities, and combinations of airborne materials can be presented at a mere keystroke or switch closure. Moreover, because the systems of the present invention can easily dispense volumes as small as a few hundred picoliters of fluid, they can provide exquisitely fast and precise olfactory inputs, near the threshold (approximately 10 billion molecules) of human olfaction.

The olfactory stimulating devices of the present invention will relieve all end users of the difficulty of preparing any of their to-be-tested materials because the units will be pre-loaded with stimuli.

The miniature size of the devices of the present invention makes novel applications possible. The devices can be fitted inside any airhandling systems (such as scuba airways, pilot airways, automotive airhandlers), they can be worn (on glasses, helmets, decorative pins, microphone holders), or they can be concealed near subjects (in head rests, door jambs, table centerpieces, television chassis). All of these applications open new horizons to olfactory access.

According to an alternate embodiment of the present invention, the compact, solid-state volatile substance dispenser, will "print" miniature clouds of airborne materials into the airspace in front of a VR trainee/subject's nose. The device can be smaller than the typical cartridges used in ink-jet printers and two such devices would fit onto VR goggles or face masks for direct dispensing into the nasal airspace. Binasal stimulation is attainable for directional cues based on olfactory and/or intranasal trigeminal signals. Dispensing of the airborne materials can also be accomplished inside closed face masks or breathing masks.

In still another embodiment of the present invention, volatile substances can be "printed" on the edges or onto the mating faces of a greeting card. According to this embodiment of the invention, the volatile substances preferably are mixed with polymers so that when the greeting card is opened, an aroma is liberated.

In still another embodiment, the olfactory stimulating devices of the present invention can be used to synthesize fragrances by micro-dispensing one or more airborne materials in various combinations.

BRIEF DESCRIPTION OF THE DRAWINGS

Other advantages and features of the invention will become more apparent with reference to the following detailed description of presently preferred embodiments thereof in connection with the accompanying drawings, wherein like reference numerals have been applied to like elements, in which:

FIG. 1A is a schematic view of an ink-jet-based digital dispenser according to the present invention;

FIG. 1B is a cross-section taken along line 1B—1B of FIG. 1A;

FIG. 1C is a schematic view of the functional elements of the micro-dispensing device incorporated in the ink-jet-based digital dispenser shown in FIGS. 1A and 1B;

FIG. 22 is a schematic view of a long and short duration olfactory stimulus from an ink-jet based digital dispenser according to the present invention;

FIG. 23A is a schematic view of microreservoirs and manifolds attached to six parallel ink-jet channels;

FIG. 23B is a schematic view of an upper layer of a laser etched plate forming manifolds for the ink-jet channels shown in FIG. 23A;

FIG. 23C is a schematic view of a lower layer of a laser etched plate forming reservoirs for the ink-jet channels shown in FIG. 23A;

DESCRIPTION OF THE PREFERRED EMBODIMENT

Figure 2:
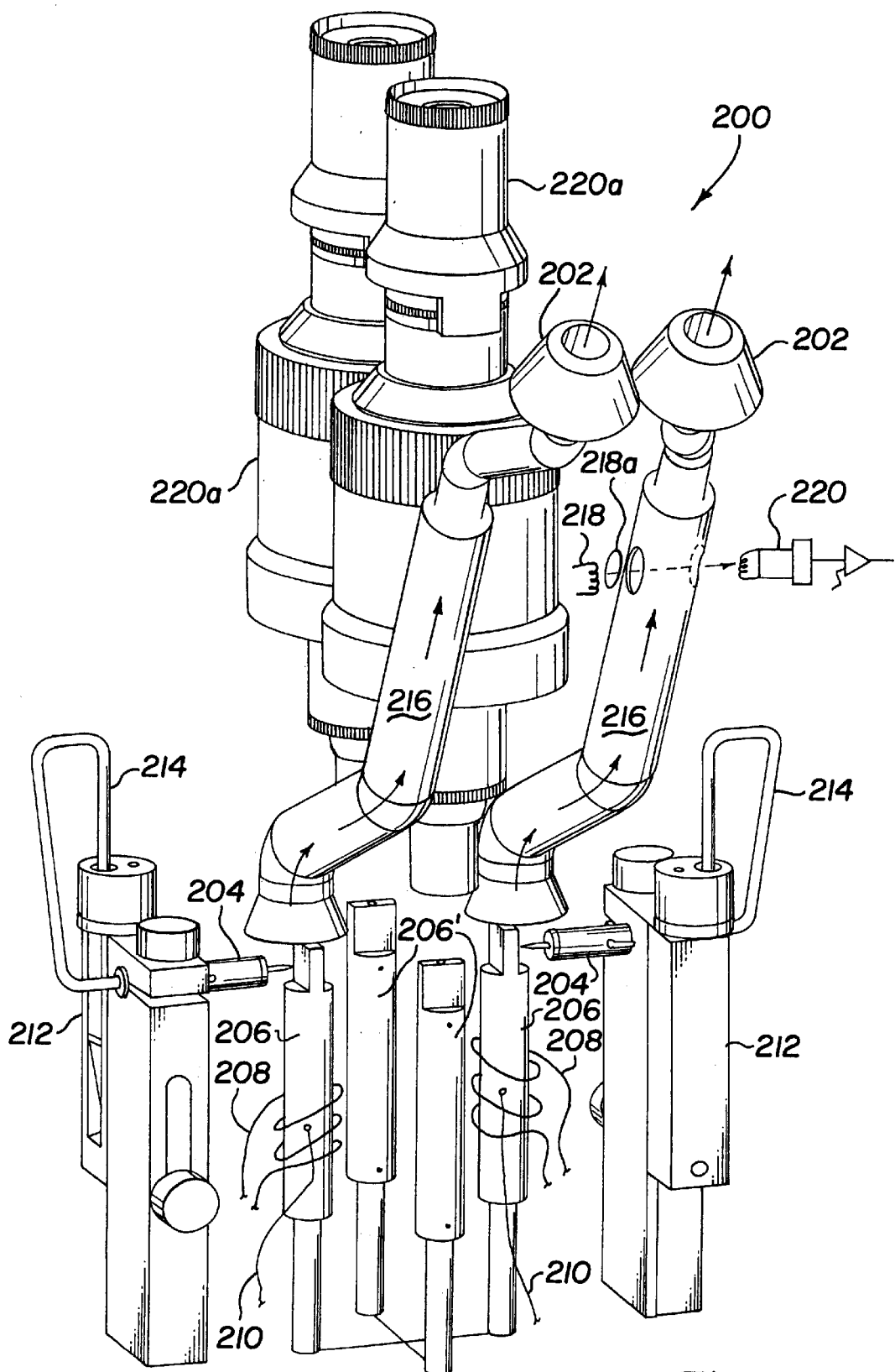
FIG. 2 is a schematic view of an ink-jet-based digital dispenser according to the present invention.

As shown schematically in FIGS. 1A and 1B, the digital dispenser 10 of the present invention includes ink-jet micro-dispenser technology by incorporating piezoelectric transducer jets 12 which may be formed of piezoelectric material such as lead zirconate titanate (PZT). Those of ordinary skill in the art will recognize, however, that the piezoelectric transducer can be replaced by other transducers such as electrostrictive transducers, magnetostrictive transducers and electromechanical transducers. As shown in FIG. 1B, the digital dispenser 10 preferably includes eight piezoelectric microdispensing channels 12.

The test substances may be dispensed from reservoirs 16 in which test substance volume dispensing resolution preferably will be in the range of 200 picoliters. The test substances may include drugs, fragrances and volatile component containing substances. The test substances may also include nicotine for use in a cigarette withdrawal regimen.

The piezoelectric microdispensers 12 are integrated into individual, modular mechanical and hydraulic assemblies. These assemblies in turn are integrated into the airborne material delivery system. Conventional control electronics 14 and software design well known to those of ordinary skill in the art for use in solder microdispensing are used in the digital dispenser 10. The digital dispenser 10 according to the present invention permits the optimization of microdispenser operating parameters in terms of waveform and frequency for the airborne material/vehicle combinations.

According to a preferred embodiment of the present invention, water, ethanol and propylene glycol are used as the fluid vehicles for low concentration airborne material dispensing. All the test substances of interest are soluble in water, ethanol or propylene glycol, and none of the vehicles will interfere with olfactory thresholds for the 10 to 1000 picoliter dispensing volumes employed by the digital dispenser 10 of the present invention. The surface tensions and viscosities (magnitude and Newtonian vs. non-Newtonian) of the pure test substance solutions to be used are within the range such that their dispensing performance will be acceptable.

A schematic of the functional elements of the micro-dispensing device 12 of the digital dispenser 10 of the present invention is shown in FIG. 1C. As shown in FIG. 1C, the micro-dispensing device 12 incorporated in the device of the present invention includes a fluid fitting 18, a piezoelectric crystal 20, a glass tube 22 and an orifice nozzle 24. The fabrication technology and processes as well as the operating characteristics of this type of device are disclosed and claimed in U.S. Pat. Nos. 5,227,813, 5,235,352, 5,334,415, 5,345,256, 5,365,645, 5,373,314, 5,400,064, 5,402,162, 5,406,319, 5,414,916, 5,426,455, 5,430,470, 5,433,809, 5,435,060, 5,436,648 and 5,444,467, the entire disclosures of which are hereby incorporated herein by reference. The functional elements of the micro-dispensing device 12 of the digital dispenser 10 of the present invention as shown in FIG. 1C are integrated into a housing 26 that includes a fluid fitting as shown in FIG. 1A. This assembly is installed into a mechanical assembly that includes an electrical connector, fluid reservoir 16, and fluid filter. It also provides the mechanical reference surfaces for mating with the digital dispenser 10 of the present invention.

Airflow in the direction of the arrows shown in FIG. 1A is passive and is controlled by a subject's sniff or inhalation. The interface 28 to a subject preferably is similar to the output of a nasal inhaler, with one output for each nostril, although the interface may also have a single output for both nostrils. The total air volume for each channel preferably is less than 200 ml to insure that all of the airborne material is inhaled during a sniff (average of 0.5 liter/second flow rate during a 0.5 second sniff). Preferably a fan (not shown) and an activated charcoal filter 32 will be attached to the inlet 34 of the device 10 to provide a brief air purge to remove any residual test substance from the system between trials.

The dispensers 12 are targeted onto heated screens 36, preferably formed of platinum, to vaporize the test substance and vehicle. Preferably the platinum screens 36 are heated during the air purge between trials. A water dispenser 30 can be activated to humidify the air. Also, it is preferred that two heated platinum screens 36 are used to allow binasal testing.

If required, an aerosol blocking filter 38 may be included to filter aerosol particles (larger than 1 $\mu$m) that might be generated during high frequency multiple droplet dispensing events, due to later droplets impacting into a pool.

In a preferred embodiment, the digital dispenser 10 includes eight droplet generators. Each micro-dispensing device 12 is evaluated in a test stand with isopropanol being used as a test fluid. Droplet size and velocity as a function of drive voltage and frequency are measured for several frequencies. Droplet velocity is measured by stroboscopically "freezing" the drops in space and measuring the droplet-to-droplet distance ($V=f\lambda$) through a microscope. Drop size is measured by measuring the flow rate of the drop stream over a precise time interval.

Each test substance/vehicle solution of interest is tested for its microdispensing performance in the test stand over a range of concentrations. For threshold testing of the sense of smell, 3–4 orders of magnitude dynamic range (60–80 decismels), where:

$$1 \text{ decismel} = \frac{\log 10 \text{ [odor concentration]}}{20}$$

are needed. This is achieved by a combination of varying the concentration of the test substance in the vehicle and varying the amount dispensed. For example, the delivered mass requirements of one olfactory stimulation could require dispensing a single 200 picoliter drop of dilute (such as $10^{-2}$) solution for the minimum and 100 drops (delivered over 0.05 seconds at 2 kHz) of pure test substance for the maximum. In this case, two solutions of the test substance would be used. Waveforms previously developed for ink-jet printing may be used to develop optimum waveforms for each test substance of interest. The drive waveform parameters, voltage, number of drops to be dispensed, and frequency are downloaded to the drive electronics 14 for each dispensing event. A system control program is used to automate repeated dispensing events, to control an audible "sniff now" signal, to control the heater elements of the heated screens 36, and to control the humidifier jet 30. The system of the present invention also provides a variable time delay between dispensing of the test substance and the audible signal in order to allow the airborne material to fully permeate the air volume to be inhaled. Even when using software event control, the response of the control system will be less than 0.1 seconds.

Referring now to FIG. 2, an alternate embodiment of the digital dispenser is shown therein. The digital dispenser 200 generates odoriferous gas clouds in an air stream and can be used for testing human smell, with the human subject sniffing at the nostril pads 202 or to monitor the physical characteristics of gas clouds by infrared (IR) densitometry. Preferably the nostril pads 202 fit snugly against the fleshy perimeter of the nares openings of the human subject.

According to the digital dispenser 200, an odoriferous fluid is jetted from a jet 204 onto a wick 206 which can be heated by a heating coil 208 and monitored by a thermocouple 210. The temperature regulated hot wick 206 vaporizes the odoriferous fluid. In a preferred embodiment, the vapor from the hot wick 206 may be pulled by vacuum or pushed by pressurized nitrogen gas through airtubes 216 at a constant velocity so as to permit calibration of the digital dispenser 200. In another preferred embodiment, the wicks 206 were made by gluing together two resistance temperature devices ("RTD's") and coating the pair with an aluminum ceramic adhesive (Cotronics Corp. Durapot). One RTD was used as a temperature sensor, the other, as a heater. Preferably, a proportional controller maintained wick temperature within a few degrees centigrade.

The odoriferous fluid is stored in reservoirs 212 which are in fluid communication with a jet feed line 214. The fluid reservoirs 212 preferably are small diameter coiled tubes attached directly to the back of the jets 204. Airflow up the airtubes 216 is indicated by the arrows in FIG. 2. Those of ordinary skill in the art will recognize that the digital dispenser 200 can be constructed to have a single airtube or dual airtubes 216 as shown in FIG. 1C. The airflow carries the gas cloud through an infrared beam generated by a source 218 and detected by an infrared detector 220. The gas cloud exits the airtube 216 at the nostril pads 202. The gas clouds generated in the digital dispenser 200 can be detected either by a human subject sniffing at the nostril pads 202 or by the IR beam interruption.

The two jets 204 are controlled by two electronic drive boxes, and the two wicks 206 are controlled by two temperature controllers.

The digital dispenser 200 preferably also includes a pair of microscopes 220a and an extra pair of wicks 206'. This configuration allows the jets 204 to be rotated and aimed at the wicks 206'. The microscopes 220a allow observation of drop formation from the jets 204 and the aim of ejection from the jets 204 to the wicks 206'.

As noted above, the vapor from the wick 206 was monitored by an IR absorptiometry system. The IR beam is generated by a regulated IR filament 218. The IR beam is collimated and aimed to pass through the gas cloud in the airtube 216, then through a narrow-pass glass filter (218a) which is set to the peak absorption of the odorant vapor (2.4 μm). The intensity of the transmitted IR radiation is monitored by a solid state IR detector 220 cooled by an internal peltier device (solid state electronic cooler).

Figures 3A, 3B:
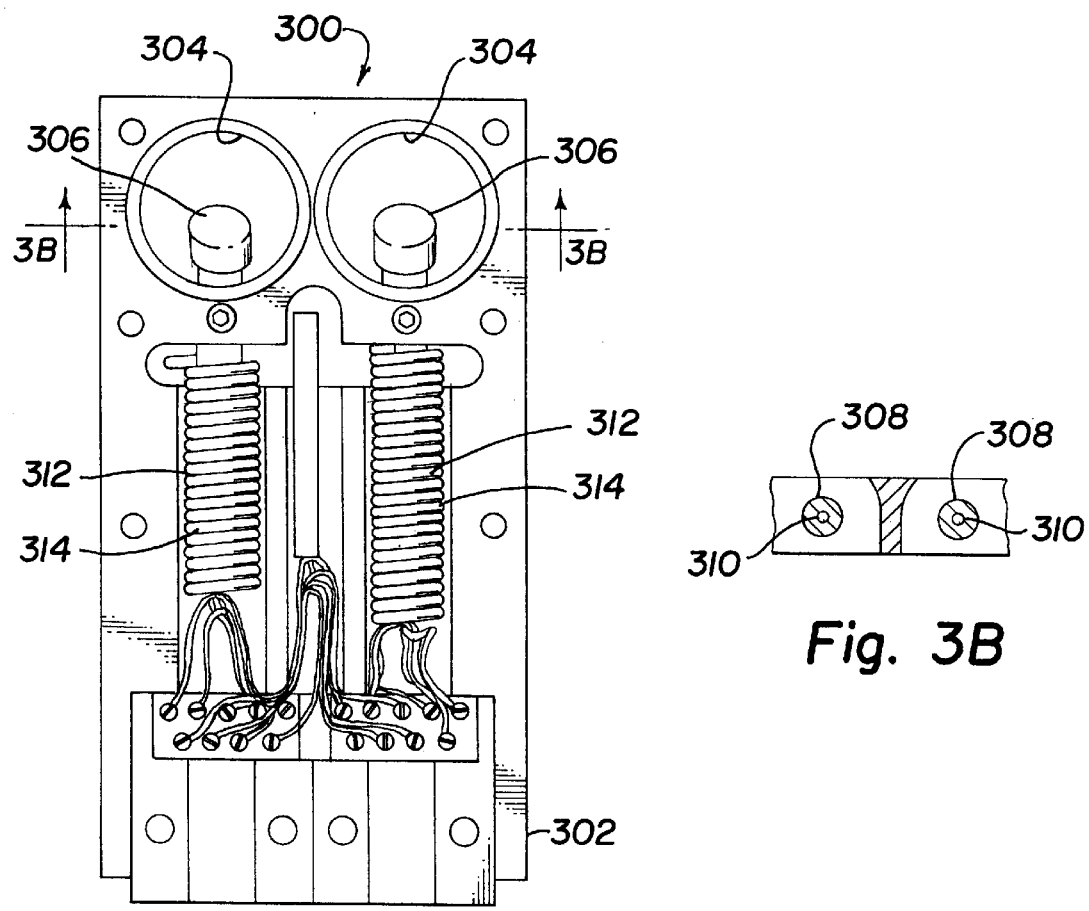
FIG. 3A is a schematic view of an ink-jet-based digital dispenser according to the present invention.
FIG. 3B is a cross-section taken along line 3B—3B of FIG. 3A.

Referring now to FIGS. 3A and 3B, another alternate embodiment of the digital dispenser according to the present invention is shown therein in which the back cover of the apparatus has been removed FIG. 3A. According to the embodiment shown in FIGS. 3A and 3B, the digital dispenser 300 is characterized by a block of aluminum 302 in which the airtubes 304 are reduced to two short holes drilled through the block of aluminum 302. The wicks 306 are placed within these holes and the jets 308 are placed inside the aluminum block, with the dispensing nozzles 310 aimed at the wicks 306. The fluid reservoirs 312 are miniature tubes 314 that are coiled around the bodies of the jets 308. The coiled tube reservoirs 312 were found to be particularly advantageous in that if the orientation of the device in space is changed the meniscus of the fluid in the reservoirs will not be altered to an extent that will affect the jetting characteristics of the jets 308 since the inlet and outlet of the fluid reservoirs 312 cannot be separated in space. Control of the wicks 306, preferably, is by two programmable temperature controllers such as Omega® CN7600 temperature controllers which operate in proportional integral derivative (PID) mode. The wicks 306 preferably are resistance temperature devices (RTD's) that are placed back to back, so that one RTD device is used for heating and one is used for feedback to maintain proper temperature of the wicks 306. The wicks 306 may be Omega® TFD RTD's and may be controlled by a proportional controller. The jets 308 preferably are controlled in a conventional manner well known in the art or by a battery-powered drive system.

Figure 4:
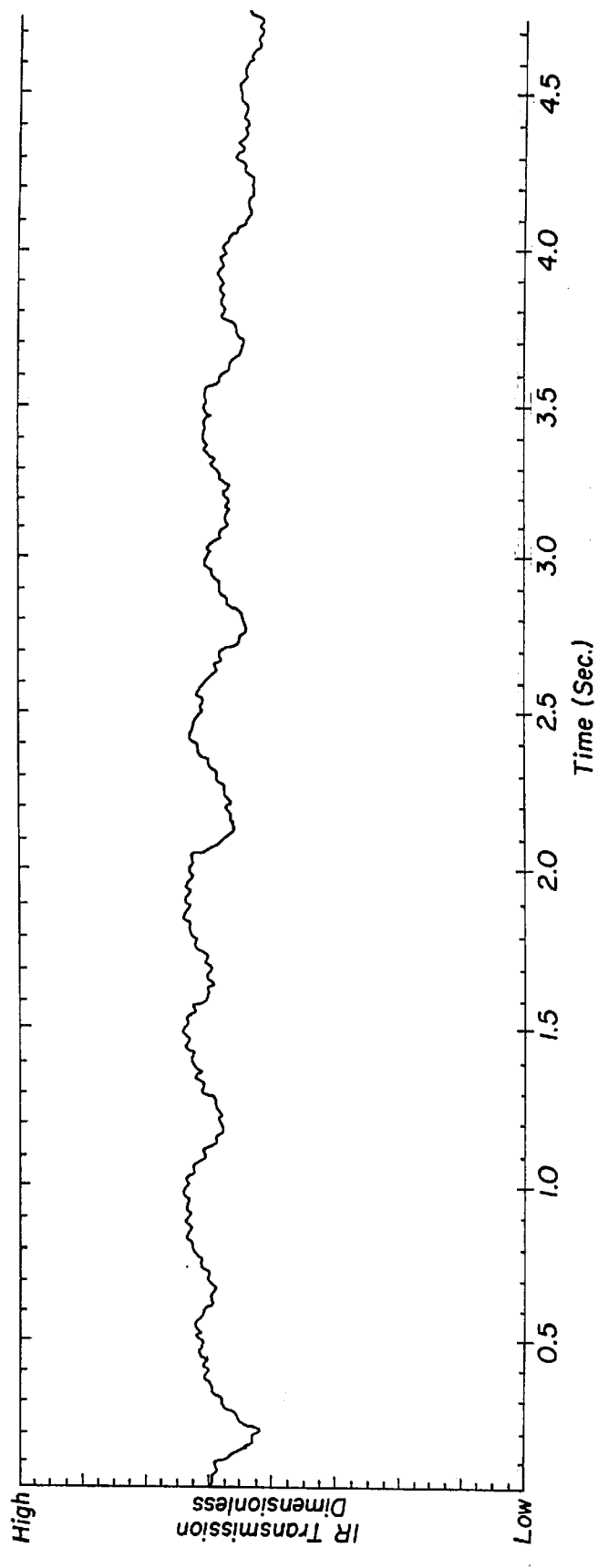
FIG. 4 is a graph of relative IR signal versus time for gas cloud generation in the ink-jet-based digital dispenser illustrated schematically in FIG. 2.

Referring now to FIG. 4, the voltage proportional to the IR beam that is directed across the airtube 216 of the device shown in FIG. 2 is shown. Downward deflection of the signal indicates that the IR beam is being absorbed by the gas cloud. Repetitive drops of fluid were dispensed on the heated wick 206 at a rate of 2 drops per second. As shown in FIG. 4, each drop generated a slight "dip" in the IR signal. Each drop had a volume of about 100 picoliters (pl) and a mass of about 100 nanograms (ng) which constituted about 3 nMoles of gas, total.

Figure 5:
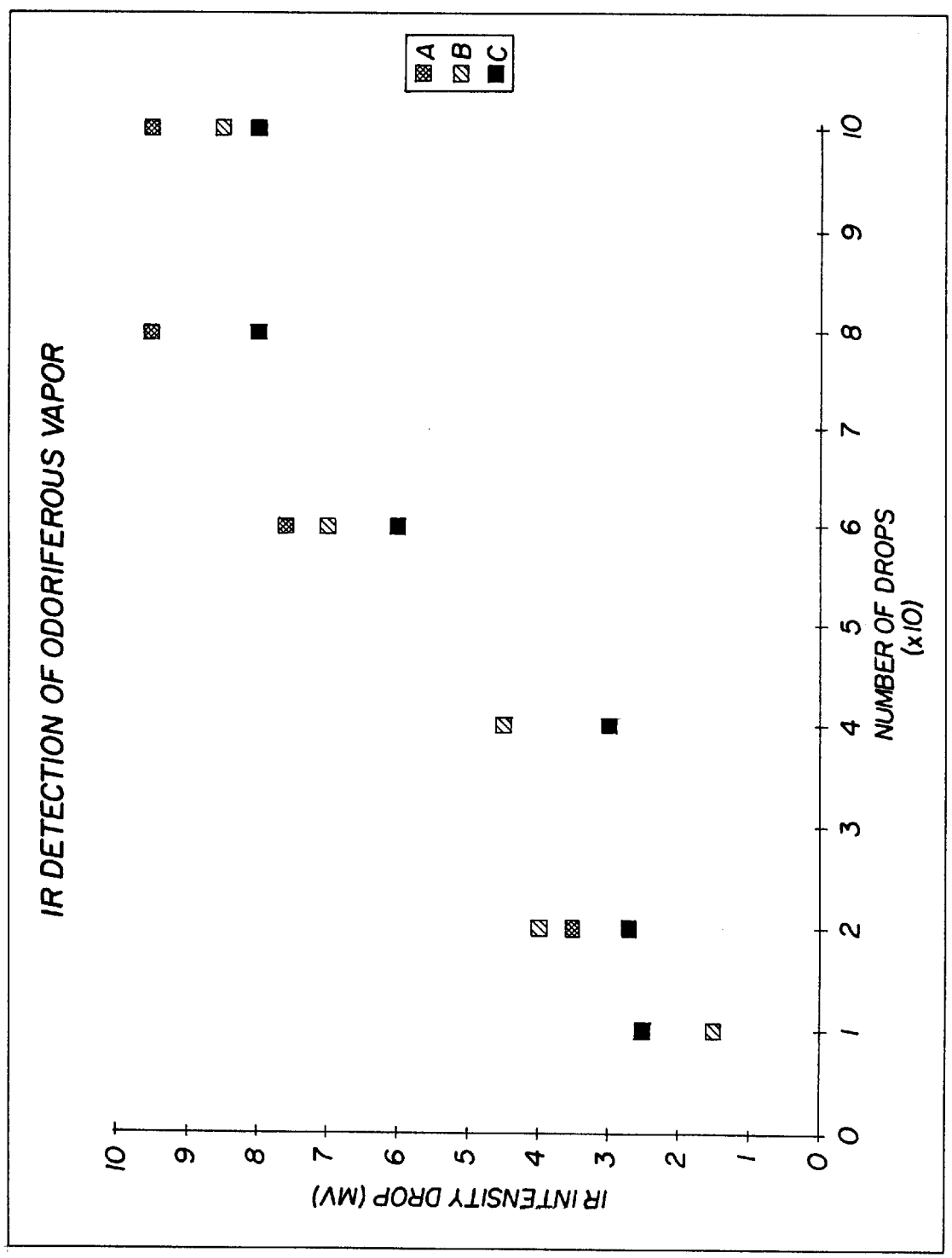
FIG. 5 is a graph of IR intensity versus number of drops of fluid dispensed onto the wick of the ink-jet-based digital dispenser illustrated schematically in FIG. 2.

FIG. 5 shows three trials conducted with the device shown in FIG. 2 of the effect on the gas cloud concentration as the number of fluid drops dispensed is varied from 10 to 100 (1000 to 10000 pl). FIG. 5 confirms by IR absorptiometry that the gas cloud concentration, in terms of IR beam intensity, rose monotonically with increasing numbers of fragrance micro drops delivered to the wick 206. The drops of fluid were delivered in bursts at a rate of 1000 per second.

Figure 6:
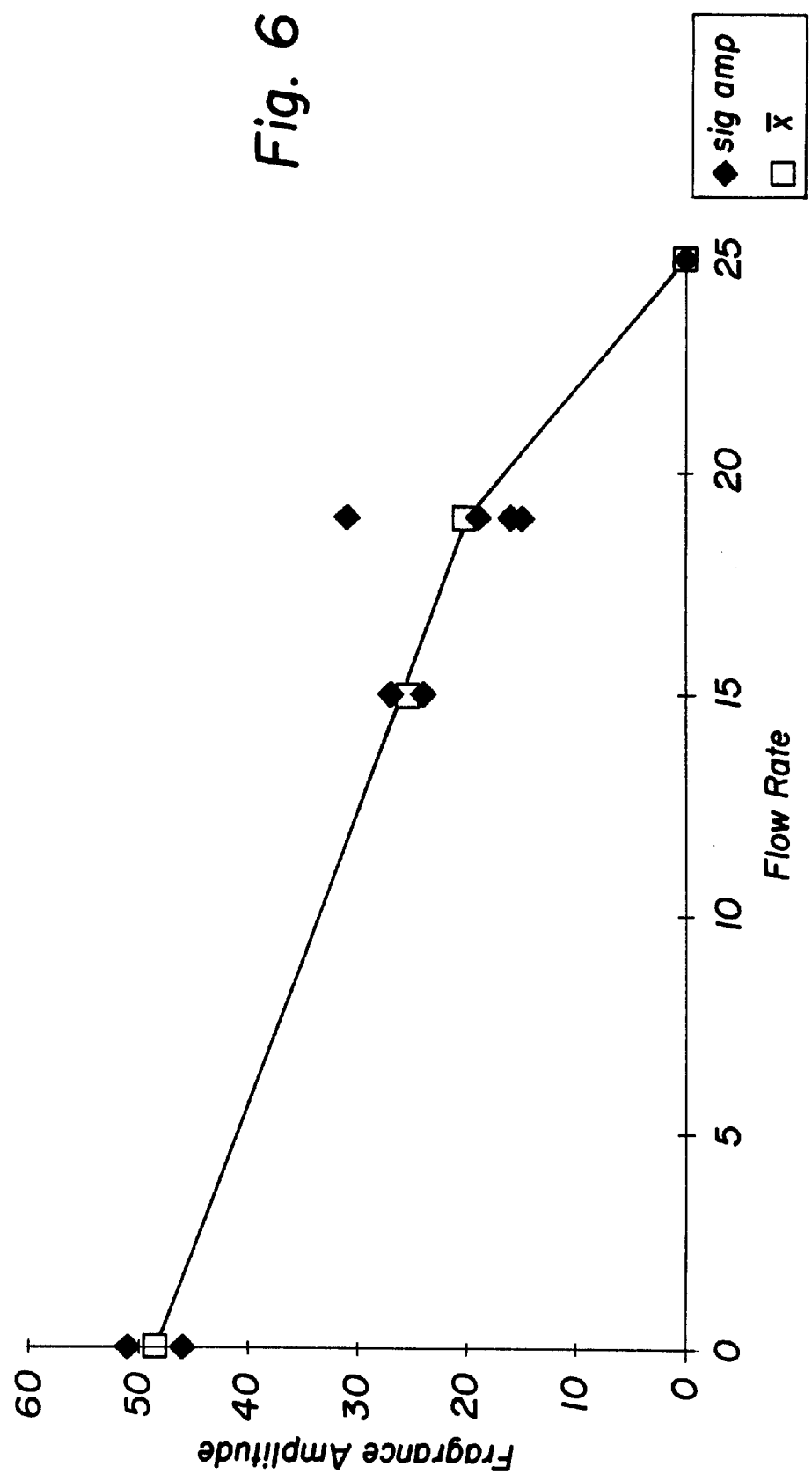
FIG. 6 is a graph of concentration of gas in the airtube of the ink-jet-based digital dispenser illustrated schematically in FIG. 2 observed by IR densitometry versus forced air flow rate.

FIG. 6 shows the effect of forced air flow through the type of apparatus shown in FIG. 2 on the gas concentration in the airtube 216 observed by IR densitometry. As shown, the concentration of gas in the airtube 216 became more dilute with an increasing rate of forced air flow. In other words, the odorant concentration ascending the airtube 216 is a linear function of flowrate through the airtube 216 when the odorant volume (i.e. the number of fluid drops) and the wick temperature were both held constant, the velocity of air flow controlled the concentration of the odoriferous gas.

Figure 7:
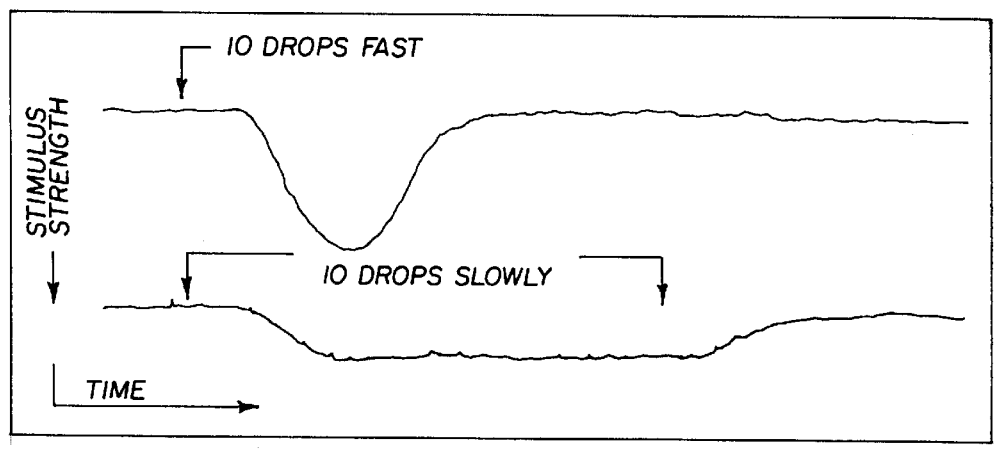
FIG. 7 is a graph of IR intensity versus time for a brief large amplitude puff (upper trace) and a longer, smaller amplitude puff (lower trace) in the ink-jet-based digital dispenser illustrated schematically in FIG. 2.

FIG. 7 shows that the temporal envelope of the gas cloud can be varied by the rate at which the fluid is dispensed. FIG. 7 shows that olfactory stimuli can be generated with complex temporal waveforms. Such stimuli can be pivotal as stimuli for olfactory evoked potential research, and for studying the temporal characteristics of olfactory perception and the olfactory deficits diagnostic of diseases such as Alzheimer's. FIG. 7 shows that by simply changing the rate at which drops are dispensed, the same total volume of odorant (700 pl) can be presented as a brief, large amplitude puff (upper trace) or a longer, smaller amplitude puff (lower trace) by varying the rate at which the odorant drops are dispensed on the wick. The waveforms shown in FIG. 7 are averages of 4 trials with the signal recorded directly by IR absorptiometry. Thus, FIG. 7 shows that by simply changing the rate at which drops are dispensed, the same total mass of odor (same total number of molecules) can be delivered as either a single burst or brief puff or a sustained, steady-state concentration. Any arbitrary temporal pattern can be achieved in this way. This advance allows the temporal characteristics of olfaction in normal and diseased subjects to be probed.

Figure 8:
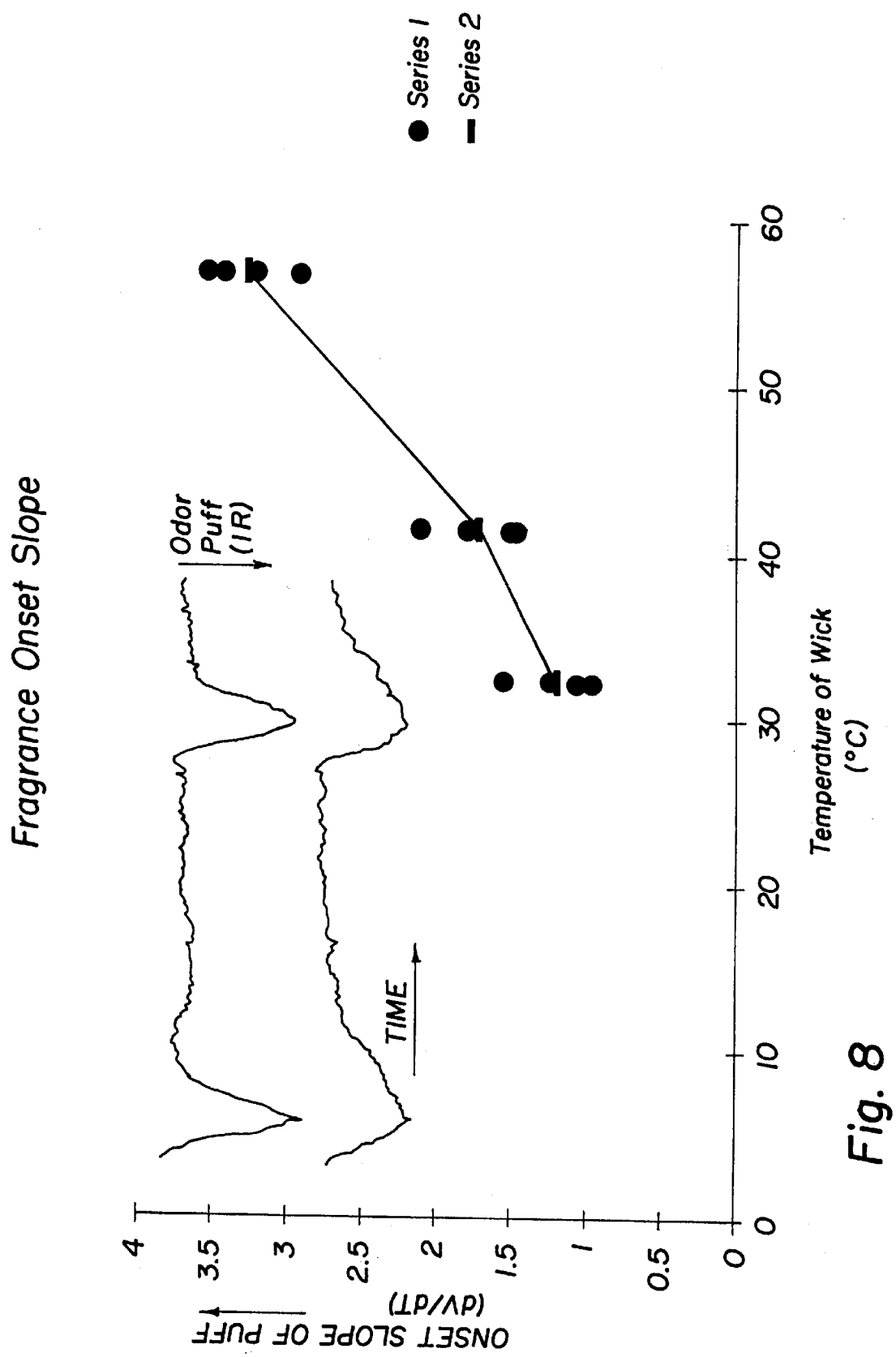
FIG. 8 is a graph of the onset slope of the IR gas-detection signal versus the temperature of the wick of the ink-jet-based digital dispenser illustrated schematically in FIG. 2.
Figure 9:
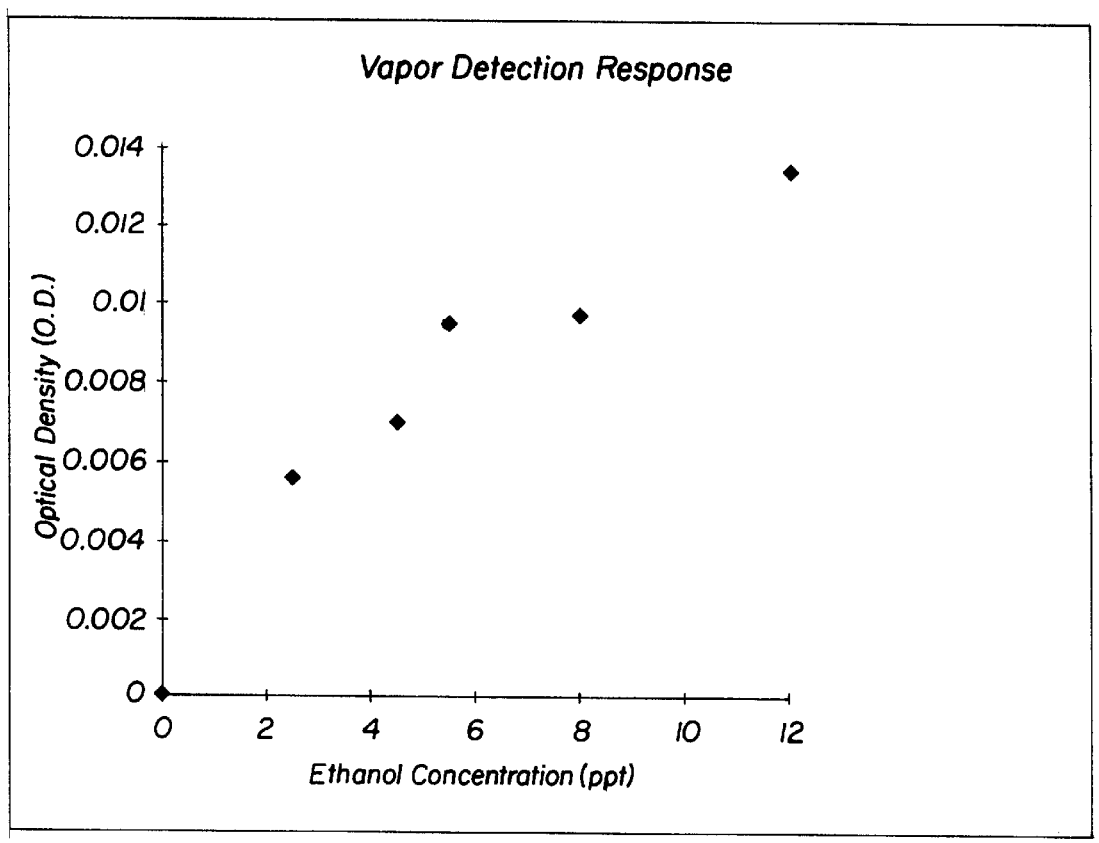
FIG. 9 is a graph of optical density (O.D.) versus ethanol concentration in parts per thousand for a vapor detection response for the ink-jet-based digital dispenser illustrated schematically in FIG. 2.

FIG. 8 is a graph of the onset slope of the IR gas-detection signal versus the temperature of the wick 206 of the apparatus shown in FIG. 2. The temperature of the wick 206 changes the initial rate of gas generation and the hotter the wick the more abrupt is the onset of the gas cloud.

When the flow of gas through the airtube 216 is controlled by flow regulators, vacuum or pushed by pressurized nitrogen, it is possible to generate and deliver known and constant concentrations of ethanol vapor (by mixing nitrogen saturated with ethanol vapor and clean, dry nitrogen) at known and constant flow rates through an airtube such as that represented by reference numeral 216. With this system, it is possible to calibrate the IR vapor detector 220 to known concentrations of odorant vapor (ethanol). Such calibration data, showing the optical density (O.D.) to be a linear function of the vapor concentration are shown in FIG. 9.

FIG. 10 shows the results of sensory testing with 100% ethanol and demonstrates the importance of the temperature of the vaporization wick 206. As shown in FIG. 10, small volumes of ethanol dispensed at up to 8 nl generated only sub-threshold gas puffs when the vaporization wick 206 was at room temperature, whereas when the vaporization wick 206 was heated to approximately 100° C., the subject could readily detect as little as 200 pl (one microdrop) of the ethanol.

Direct physical measurement of the vapor puffs by IR absorptiometry explained the psychophysical findings noted above. Specifically, the wick temperature was found to directly control both the rise time and the amplitude of the vapor puff ascending through the airtube 216. As shown in FIG. 8, the wick temperature was varied over the range of 32 to 56° C., and the fragrance "puff" was monitored by IR absorption as it ascended the airtube 216. The leading edge of the puff stimulus was distinctly sharper and of larger amplitude with the hotter wicks. Also, the insets show the temporal waveforms of the generated odor puffs. As shown, the odor puff has a more abrupt onset and offset (i.e. dV/dt is larger) when the wick is hot ("a") than when it is cooler ("b"). Several sets of similar observations are plotted in the graph. The time calibration for the inset is 0.5 sec.

FIGS. 11A and 11B show human subject detection thresholds for the left, right and left+right combined nostrils according to tests conducted on the apparatus of FIG. 2. As shown in FIGS. 11A and 11B, one nostril showed a lower threshold than the other, and the combined nostril presentation yielded a threshold lower than either nostril tested separately. Three thresholds (s1–s3) were attempted in each condition. The staircase method was used.

Referring now to FIG. 12, the chip-based dispenser 50 of the present invention comprises a dispenser array 52 containing a multiplicity of tiny individual dispensing elements. These elements may all contain the same test substance (for repeated testing), contain different concentrations of the same substance (for sensitivity testing), different substances (including blocking and interacting agents), or a combination of these. Typical fluids would contain odorants for olfactory stimulation or testing, or drugs for nasal or bronchial delivery, fragrances for fragrance synthesis or odorants for periodic testing of detectors such as smoke detectors. According to the embodiment of the present invention concerning fragrance synthesis, the chip-based dispenser 50 comprises multiple samples of the odorants used to make perfumes. By digitally controlling the release of one or more odorants, fragrances may be synthesized.

According to the embodiment of the present invention concerning test detectors, a fluid may be puffed periodically to determine if a detector is working. Also, different volumes of odorants may be dispensed to calibrate or determine the sensitivity of such a detector.

The individual functional elements in the dispenser array will each include a fluid reservoir, 200–500 μm in diameter and height, filled with the test substance solution; a heating element to drive off the test substance solution; conductors connecting the ends of the heating element to the drive electronics; and a 20–50 μm diameter orifice through which the test substance is expelled. The configuration of an individual functional element in an array dispenser is shown schematically in FIG. 15. By using the parallel fabrication processes described below, this single element geometry can be repeated over an array so that densities of over 400 elements per square centimeter are achieved, as shown in FIG. 12. As shown in FIG. 12, the chip-based dispenser of the present invention also includes control electronics PROM 14, a heated evaporator 36 and the airflow moves through the device in the direction of the arrows shown in FIG. 12.

The individual dispenser elements 54 shown in FIGS. 13A and 13B depict a storage configuration and an operating configuration, respectively. In the storage configuration, a protective film cover 56 is put on and covers the orifice 58 of the element. To convert the storage configuration to the operating configuration, the protective film 56 is removed from the orifice 58 immediately prior to use. This type of system can be used for variable rate airborne material injection, or on/off airborne material injection over a period of time. To dispense test substance vapor over time, heat is added by means of the heating element 60 to increase the vapor pressure of the test substance solution 62 in a controlled manner. To eject airborne material 62 rapidly, heat is injected rapidly enough to cause a small fraction of the fluid 62 in direct contact with the heating element 60 to vaporize, causing a vapor bubble to form on the heating element 60. This vapor bubble causes a pressure rise in the remaining fluid 62 so that most of the fluid 62 in the reservoir is ejected instantaneously. This mode of operation is analogous to thermal ink-jet printing, which is widely used in office printers by Hewlett-Packard, Canon, and others. Finally, as shown in FIGS. 13A and 13B, the individual dispenser elements 54 preferably include chamber walls 64 formed of a polyimide material and further include conductors 66.

An alternate configuration is shown in FIG. 14. In this configuration, the fluid reservoir remains sealed until the instant the airborne material 62 is released. To eject airborne material 62 rapidly, heat is injected rapidly enough to cause a small fraction of the fluid 62 to vaporize, causing a vapor bubble to form on the heating element 60. This vapor bubble causes a pressure rise in the remaining fluid 62 so that the film 56 covering the orifice 58 is removed by failure of the adhesive. Most of the fluid 62 in the reservoir 54 is ejected instantaneously in the process of "blasting" off the microscopic orifice seal 56.

Figure 18:
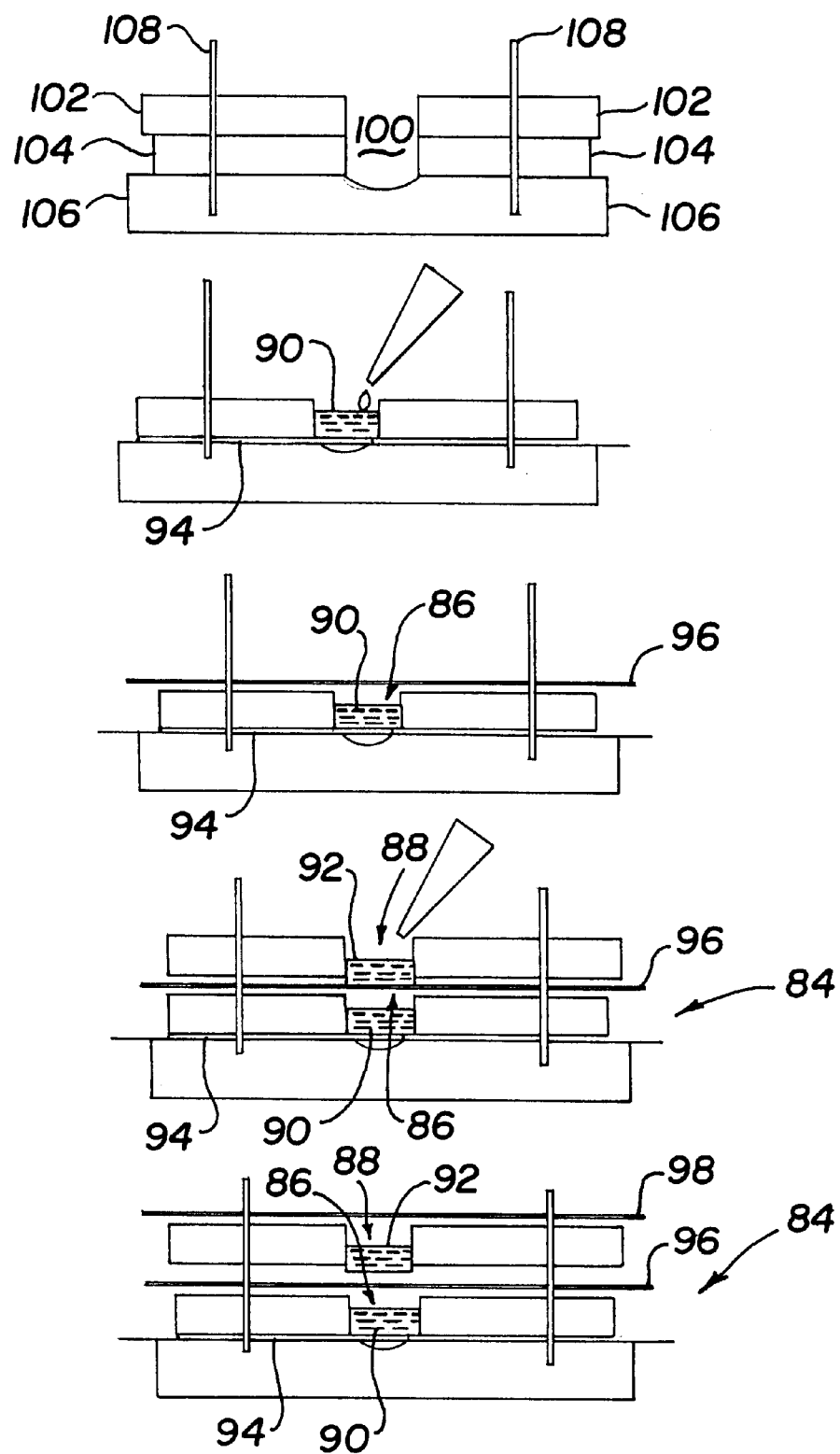
FIG. 18 is a schematic view of an another alternate embodiment of an individual dispenser element incorporated in the chip-based microdispenser according to the present invention and a method for the fabrication thereof.

Another alternate configuration of a dispenser element 84 is shown in FIG. 18. In this configuration which is similar to the configuration shown in FIG. 14, the dispenser element contains two fluid reservoirs 86 and 88. The fluid reservoir 86 contains water 90 and the fluid reservoir 88 contains a test substance 92. The fluid reservoir 88 remains sealed until the instant the test substance 92 is released. To eject the test substance 92, heat is injected by means of the heater element 94 in a manner to cause the water 90 to vaporize and burst the membrane 96 separating the reservoir 86 from the reservoir 88 and membrane 98. Most of the test substance 92 in the reservoir 88 is ejected instantaneously in the process of "blasting" off the membrane 98.

The fabrication of the chip-based dispensers 52 of the present invention utilizes processes and materials that are currently used in high volume flex-circuit manufacturing (e.g., the flex circuit for ink-jet print heads which is manufactured in volumes in excess of 10,000,000 a year) and other proven ink-jet print head manufacturing processes. Specifically, the fabrication methods developed for piezoelectric ink-jet print heads described in U.S. Pat. Nos. 3,857,049, 4,584,590, 4,825,227, 4,536,097, 4,879,568, 4,887,100, 5,227,813, 5,235,352, 5,334,415, 5,345,256, 5,365,645, 5,373,314, 5,400,064, 5,402,162, 5,406,319, 5,414,916, 5,426,455, 5,430,470, 5,433,809, 5,435,060, 5,436,648 and 5,444,467, the entire disclosures of which have been incorporated herein by reference.

Figures 13A, 13B:
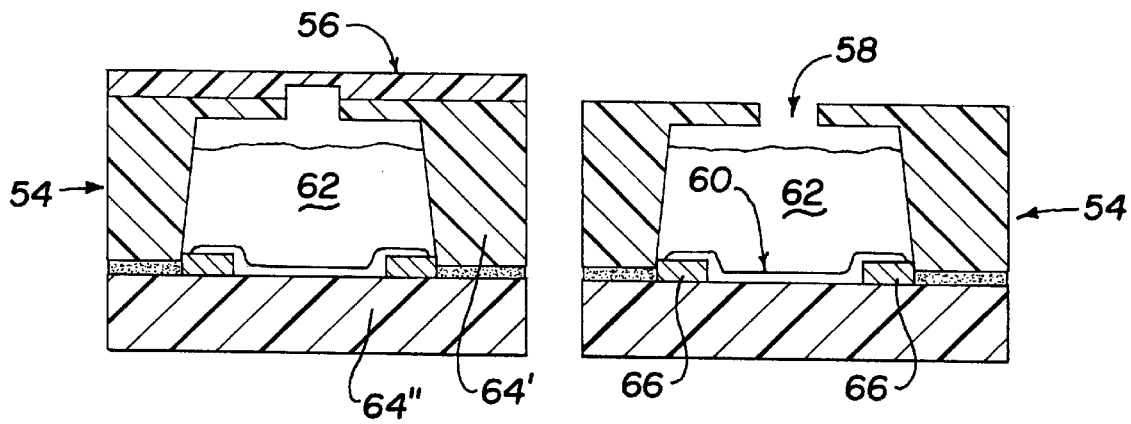
FIGS. 13A and 13B are schematic views of individual dispenser elements incorporated in the chip-based microdispenser according to the present invention.

The test substance dispensing element 54 shown in FIGS. 13A and 13B is produced from two multilayer polymer film materials 64' and 64", such as polyimide, as discussed below with reference to FIG. 15. The film 64' that has the fluid reservoir machined into it consists of a 200–500 $\mu$m thick (8–20 mils) layer of material that machines well (i.e., rapidly, repeatably, and with smooth machined surfaces) between two removable film layers. One of these layers is a protecting layer for an adhesive layer underneath it.

Figure 15:
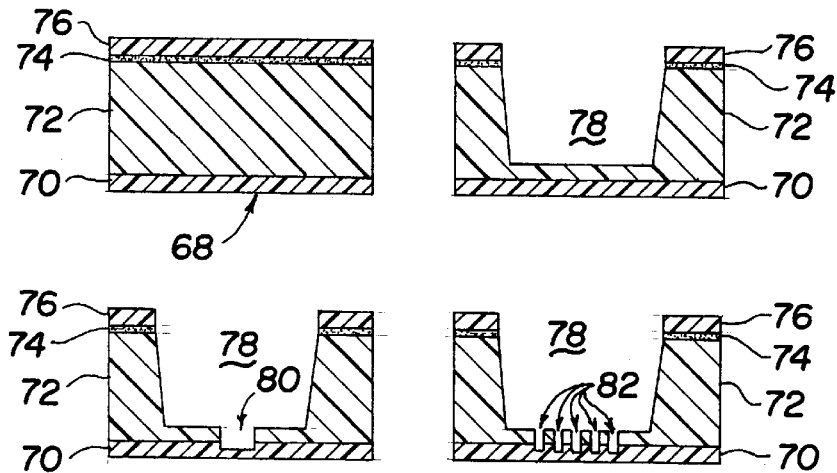
FIG. 15 is a schematic view of a two-step excimer laser ablation process for forming the reservoirs of the individual dispenser elements incorporated in the chip-based microdispenser according to the present invention.

FIG. 15 depicts a two-step excimer laser ablation process. The process is conducted on a starting material 68 which includes a film cover 70, a polymer film layer 72 disposed on the film cover 70, an adhesive layer 74 disposed on the polymer film layer 72 and a film cover 76 disposed on the adhesive layer 74. In the first step of the excimer laser ablation process, the fluid reservoir 78 is machined in the film cover 76, the adhesive layer 74 and the polymer film layer 72. In the second step of the excimer laser ablation process, the orifice 80 or orifice array 82 are machined into the polymer film layer 72 and the film cover 70. Preferably, a sheet of adhesive backed, 0.5 mm thick polyimide is excimer laser machined with 0.5 mm holes on 2 mm centers to form the fluid reservoirs 78. Step-and-repeat focal point machining (i.e., one hole at a time) may be used instead of a mask.

Figure 14:
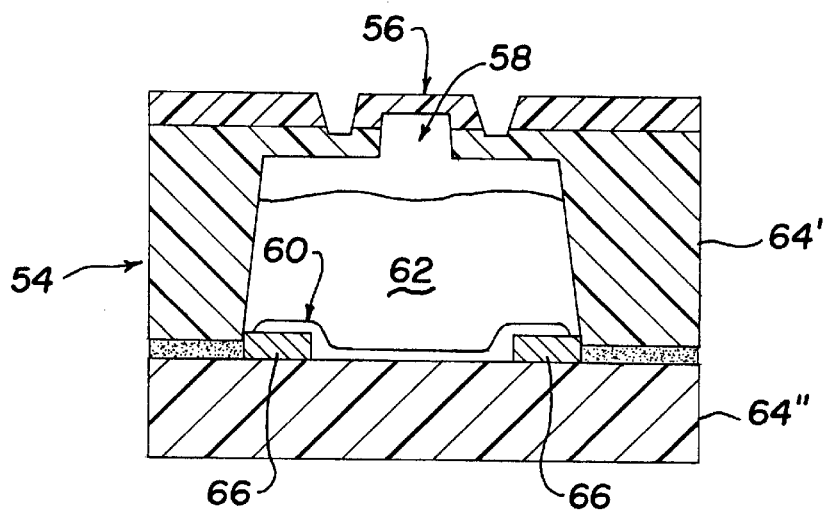
FIG. 14 is a schematic view of an alternate embodiment of an individual dispenser element incorporated in the chip-based microdispenser according to the present invention.

The alternate configuration of the individual dispenser elements shown in FIG. 14 requires reversing the film and performing an additional laser ablation step.

Masks with 200–500 repetitions of the same pattern can be used to produce an entire array at the same time (5–10 seconds per ablation step). The material will then be translated and the process repeated, resulting in a large number of arrays being produced on a continuous piece of film material. The processes and materials are very similar to those used to fabricate ink-jet printer orifice plates as disclosed in the patents mentioned above and incorporated herein by reference. The processes and materials can be used to produce an orifice plate having 120 channels on 170 $\mu$m centers.

The second multilayer film 64" is a conventional flex circuit containing the electrical leads for the heating elements. The conductors 66, preferably made of copper, are defined using a photolithographic process. Each pair of conductors 66 preferably have a spacing corresponding to the fluid reservoir width at one end, and a width spacing suitable for interconnecting to the control electronics at the other end.

Figure 17:
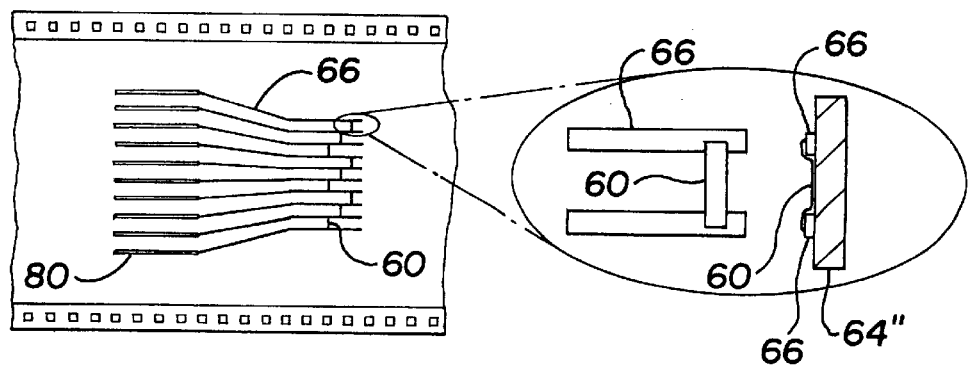
FIG. 17 is a schematic view of heating elements deposited onto flex circuit material for the individual dispenser elements incorporated in the chip-based microdispenser according to the present invention.

The heating elements are screen printed across the conductors using a thick film polymer resistor material. The width of the resistor preferably is 100 $\mu$m and the thickness preferably is 20 $\mu$m. A family of carbon filled polymer materials designed for screen printing onto flex circuit material is commercially available for this purpose from Grace Specialty Polymers. These materials are available in resistivities from 1$\Omega$/sq to 100 M$\Omega$/sq. FIG. 17 illustrates one of a number of circuits on industry standard 35 mm TAB (tape automated bonding) flex circuit film with copper conductors and resistors 80 printed between conductors 66.

Polymer resistor material is dispensed onto the flex circuit conductors 66 using a small gauge syringe. All the conductors 66 are shorted by a single dispense of the epoxy, but only two conductors 66 will be connected at any time, so the effective heating element 60 will consist of the 170 $\mu$m segment between the two active conductors 66. After curing, the resistance will be measured. Based on the measured resistance, the resistivity of the polymer resistor material will be adjusted to achieve the desired resistance (a few Ohms) and the heater element 60 will be applied to 20–30 flex circuits.

Figure 16:
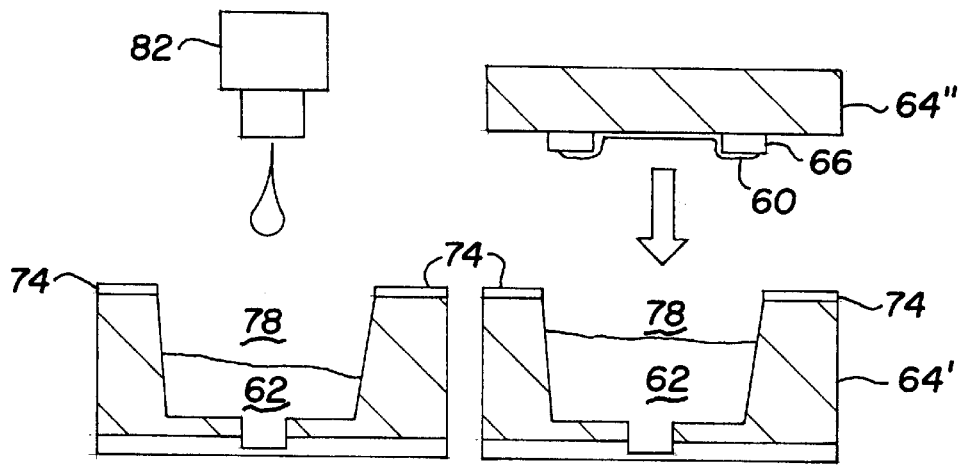
FIG. 16 is a schematic view of the final assembly of the individual dispenser elements incorporated in the chip-based microdispenser according to the present invention.

Final assembly of the dispenser array 52 involves dispensing the volatile substance fluids 62 from an ink-jet type dispenser 82 into the fluid reservoirs 78, removing the film material 76 protecting the adhesive 74, and assembling the heater flex circuit layer 64" to the fluid reservoir layer 64', as illustrated in FIG. 16. For larger reservoirs (500 $\mu$m, or 100 nanoliters volume), high speed solenoid valves preferably may be used to dispense the volatile substances. This type of valve is in common usage in large character printers in the industrial marking industry and has adequate resolution down to approximately 50 nanoliters. For smaller volumes, drop-on-demand piezoelectric ink-jet dispensing is used to dispense multiple 250 picoliter droplets at 2 kHz. To fill a 200 $\mu$m (8 nanoliter) reservoir, would require 32 droplets and 4 milliseconds.

After the test substances 62 are dispensed into the reservoirs 78, the film layer 76 protecting the adhesive 74 is removed and the film 64" containing the heater 60 is attached, sealing the fluid reservoir 78.

After assembly, the shelf life of the test substance dispensing elements 54 is determined by the stability of the test substance solutions 62.

The final assembly of the test substance dispensing elements 54 will allow a determination of the energy power threshold that causes a transition from vapor phase mass transport to fluid phase ejection resulting from bubble formation (boiling) on the heater 60. It will also allow a combination of analytical and empirical methods to be used to identify the transient mass transport characteristics as a function of total energy input, instantaneous power, reservoir/orifice geometry, and fluid level in the reservoir. It will further allow a determination of the optimum design/ operating conditions for the configuration with the "blast-off" orifice cover. Finally, it will allow a determination of the optimum geometry and operating conditions needed to achieve the preferred test substance delivery rates.

According to the present invention the design tools will be developed to optimize the design(s) of the chip-based test substance dispenser 52. Because of the extremely large range of olfactory sensitivity to different substances, chip-based test substance dispensers 52 have a broad range of requirements, and thus have to be optimized for different sets of these requirements. This makes the development of the design tools extremely important.

Of particular importance is the characterization of vapor phase versus fluid phase mass transfer. It is clear that fluid phase mass transfer provides more rapid response times, larger and discrete mass transfer rates, and limits an individual channel to one or two dispensing events. Vapor phase mass transfer is more controllable over time, and has smaller and continuously variable dispensing rates. The behavior of the chip-based dispenser 52 will determine the selection of the mass transfer means.

Analytical methods will be used for vapor phase mass transfer modeling and to predict the onset of bubble formation (boiling) on the heater. Dispensing elements according to the present invention will be fabricated and water will be used as the fluid for both the experimental and analytical evaluations. The analytical and experimental results will be used to predict the optimum geometry and operating conditions to achieve the preferred test substance delivery rates according to the present invention.

A finite element model of the chip-based dispenser 52 of the present invention will be generated using ANSYS. A three dimensional model will be used because, although the geometry will be substantially axisymmetric, the heating element 60 will not be, and the local temperature at the surface of the heating element 60 is one of the key outputs, since it will determine the onset of boiling, and thus fluid phase mass transfer.

The geometry will be parameterized to allow optimization studies to be conducted more efficiently. Non-dimensional analysis will also be used to scale the solution.

The fluid will be treated as a constant volume element (i.e., the mass transfer problem will not be solved directly in ANSYS so that the free surface will not move) in analyzing a given geometric model. Therefore, four geometric models will be constructed with the fluid level in the reservoir at four different levels.

The Rayleigh number is the nondimensional parameter that characterizes natural convection heat transfer. For water, a 50° C. temperature differential, and a characteristic dimension of 500 $\mu$m, the Rayleigh number is approximately 150. In a close space, conduction heat transfer dominates for Rayleigh numbers less than 1000. Therefore, buoyancy driven convection will be assumed negligible, up to the point that boiling occurs.

The heating element 60 will be modeled by assigning it a constant heat flux value. Latent heat effects will be modeled by assigning a variable heat flux to the fluid surface proportional to the rate of mass transfer due to vaporization. The evaporation rate will be calculated assuming the air above the fluid is saturated, thus making the mass transfer rate proportional to the heating rate. This assumption requires that diffusion through the orifice be small, and results in a zero mass flow at steady state. The system will never approach steady state and diffusion effects will be small since only short duration (1 $\mu$s to 1 ms) heating pulses will be used. Only transient solutions will be obtained, and the coupling of the heat and mass transfer solutions will use a backward differencing scheme.

FIG. 18 shows a typical five step procedure for forming the dispenser elements 84. First, three polyimide sheets 102, 104 and 106 are stacked and fixed by locating pins 108. The stacked polyimide sheets 102, 104 and 106 are then ablated in a manner similar to that described above with respect to FIG. 15 to form a central cavity 100. Next, the polyimide sheets 102, 104 and 106 are separated and the sheets 104 and 106 are reassembled with a resistive heater element 94 inserted between them. Sheets 104 and 106 are bonded together (by thermal or sonic welding) and thereafter water 90 is loaded into the central cavity 100. Next membrane 96 and the overlying polyimide piece 102 are stacked in place and bonded to the structure below, sealing the water 90 into the central cavity 100 to form a water reservoir 86. The test substance to be dispersed 92 is then loaded into the central cavity 100. Finally, membrane 98 is bonded over the top of polyimide sheet 102, sealing the test substance 92 into the central cavity 100 to form a test substance reservoir 88.

Figure 19A:
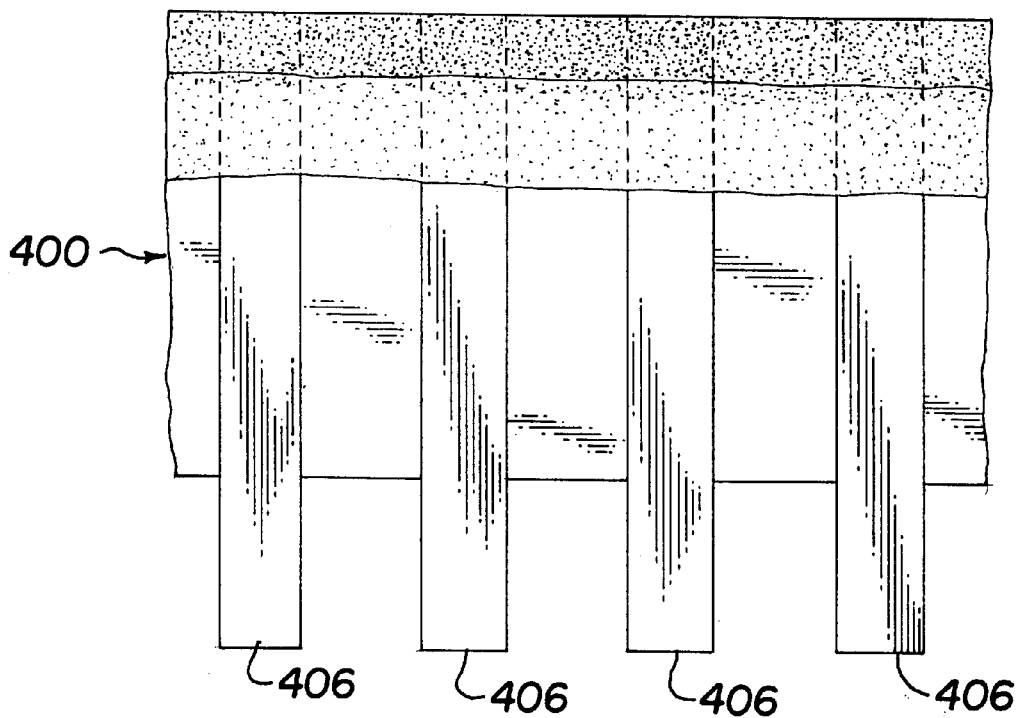
FIGS. 19A, 19B and 19C are scanning electron micrographs of the chip-based microdispenser according to the present invention.
Figure 19B:
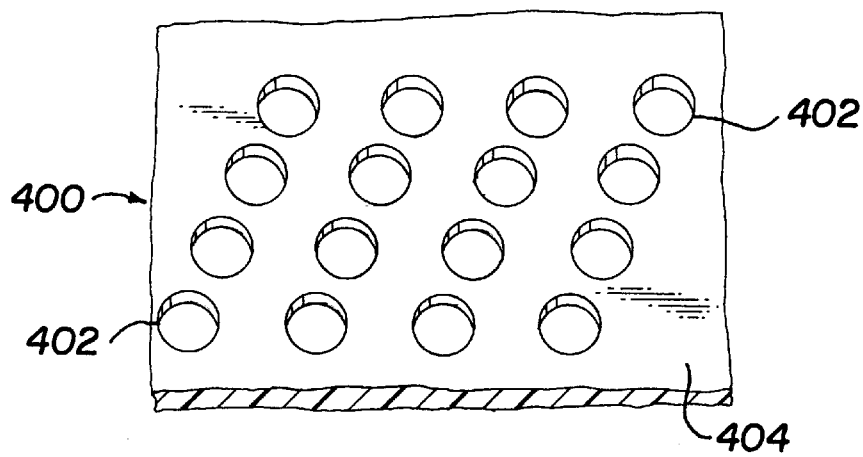
Figure 19C:
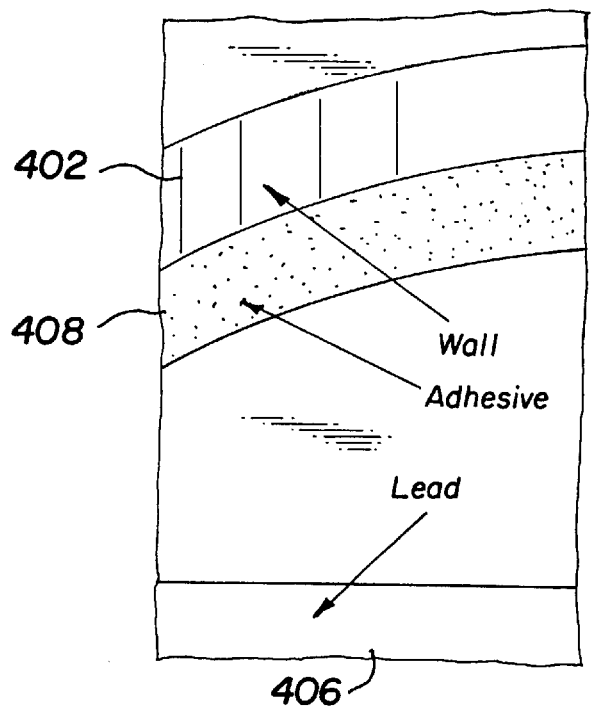

FIGS. 19A, 19B and 19C are scanning electron microscope views of a prototype "bubble-chip" type fragrance dispenser 400, with multiple wells 402 on a single "chip" 404 of plastic according to the second embodiment of the present invention. As shown in FIG. 19A electrodes 406 are provided in the bottom of the individual odor wells 402 shown in FIG. 19B. The electrodes 406 in the bottom of the wells 402 can blast the contents of the wells 402 out as a gas cloud by rapidly heating the fluid contents in the wells 402. As shown in FIG. 19C, the wells 402 are sealed with an adhesive layer 408. The bubble chips according to the present invention can be built and filled at a density of about 650 wells per square centimeter.

The odor generator chips may be constructed of two main layers, including one layer each of 250 $\mu$m thick, type A mylar (polyester) film obtained from Allied Plastic Supply, Inc., Addison, Tex. and one 125 $\mu$m thick polyimide flex circuit. The cylinders of the liquid wells were holes drilled through the polyester and the floors of the wells were the single sheet of polyimide flex circuit.

The electrical leads used to "fire" individual bubbles were leads that were plated onto the polyimide flex circuit (FIG. 19A) before joining the polyimide "floor" to the polyester "cylinders". As shown in FIG. 19A, four gold leads (70 $\mu$m) are printed onto the polyimide flex-circuit base. The lowest portion of the leads span an opening, the middle portion is backed but uninsulated on the top. Two such leads in a well bottom formed the heating circuit and the odorant fluid served as the resistive element. A nineteen conductor flexible film circuit was used. The electrical conductors plated onto the surface of the film were 50 $\mu$m wide and 25 $\mu$m thick in the area of the liquid wells.

To assemble the device, Viscor SS2200 double coated polyester 0.5 mil film coated on both sides with acrylic pressure sensitive adhesive was used to laminate the wells onto the conductor-containing bottom plate. The VS2200 was joined to the 250 $\mu$m polyester layer and the resulting "sandwich" (FIG. 19C) was excimer laser machined (Neuman Micro Systems, Inc.). FIG. 19C shows a detail of a bottom joint in an odor well. One gold-plated electrode lead is visible at the bottom, as is the approximately 0.002 inches thick layer of adhesive and the base of the well wall. The wells that were machined were 300 $\mu$m ID, set in rows that were 375 $\mu$m apart. FIG. 19B shows sixteen odor wells (350 $\mu$m diameter) after excimer drilling into polyester, then bonding to the flex-circuit "floor" of the chip. The wells are adapted to hold an odorant when filled. After the machining of the wells, the bottom layer of the VS2200 adhesive was exposed, and the well were thus bonded onto the flex-circuit "floor" by pressure bonding.

To "fire" the jets, the principle of ohmic heating was used, in which the to-be heated material (the odorant solution) is used as the heating element by passing current through that liquid. Conductive (and odoriferous) liquid was introduced into each well by micro pipette. The resistive liquid consisted of a solution of standard saline and 20% ethanol odorant. A 100–1000 msec square wave pulse ($\mu$amp levels) was used to "fire," i.e., rapidly vaporize, the fluid.

Figure 20:
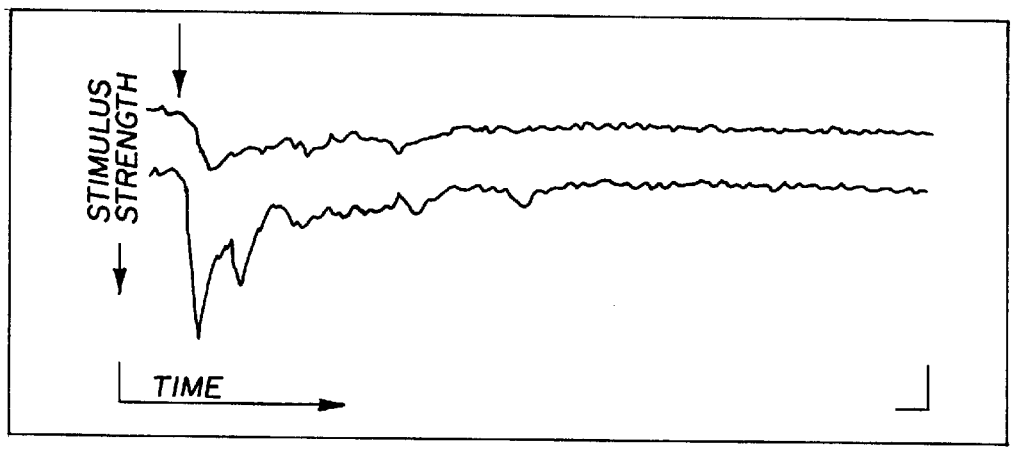
FIG. 20 is a graph of relative IR signal versus time for a gas cloud generated by blasting the contents of one odor well into the space just above a microdispenser according to the present invention.

To monitor the vapor puffs arising when bubbles were fired, bubble chips were placed at the bottom of an IR absorptiometry system and the ascending vapor puffs were monitored by IR absorptiometry. FIG. 20 shows typical results when bubbles were fired. A single current pulse fires the bubbles (upper trace) and larger initial currents give a faster and bigger puff (lower trace).

FIG. 20 are IR signal tracings of relative IR signal versus time for odorant puffs generated by flash boiling the odorant (2–4 nl) out of a single well into the space just above a bubble-chip type dispenser according to the second preferred embodiment of the present invention. The upper IR trace shows the temporal envelope of the gas cloud generated when the fluid is heated with 50 volts. The lower IR trace shows the temporal envelope of the gas cloud generated when the fluid is heated with 120 volts. As shown in FIG. 20, higher current gives a sharper initial rise in gas concentration (lower trace) than lower heating current (upper trace).

EXAMPLE 1

In order to establish the basic feasibility of the microdispensing approach to olfactometry, pilot threshold testing was conducted. The data from such testing show that the jetting produces well-controlled stimulus variation, with detection thresholds in the vicinity of 1–2 microdrops of fluid.

For these studies, fragrances were purchased commercially (vanilla extract, oil of peppermint, banana extract) and were used without modification. Each of the fluids consisted of a few percent concentration of extract dissolved in a 65:35 mixture of water and ethyl alcohol. These fluids were loaded into a piezoelectric fluid microdispenser, and the appropriate driving pulse parameters for producing consistent, reliable droplets were established by direct microscopic monitoring of the droplet formation.

Once stable drop-on-demand jetting was obtained, the jets were used to dispense from 1 to 200 microdrops onto the tip of a cotton swab. The number of drops was preselected by a digital program. Drop volume was measured directly by collecting 60,000 drops (1 kHz for 1 min) in a microfuge tube. Drop volume was calculated to be 91 picoliter. The variance on individual drop volume was not measured directly, but prior experience with similar jetting indicates drop-to-drop variance is under 2–5% (SD/mean).

For subject testing, the cotton swab that had either just been wetted by microdrops or had been left unwetted (lure) was handed to the subject for sniffing. The test design was a forced-choice paradigm with blank trials (lures) and odor trials presented in a quasi-random order, 20 times each. This same block of 40 trials was repeated once for each odor intensity level, with the number of microdrops of volatile substance used to govern the intensity of the stimulus.

Figure 21:
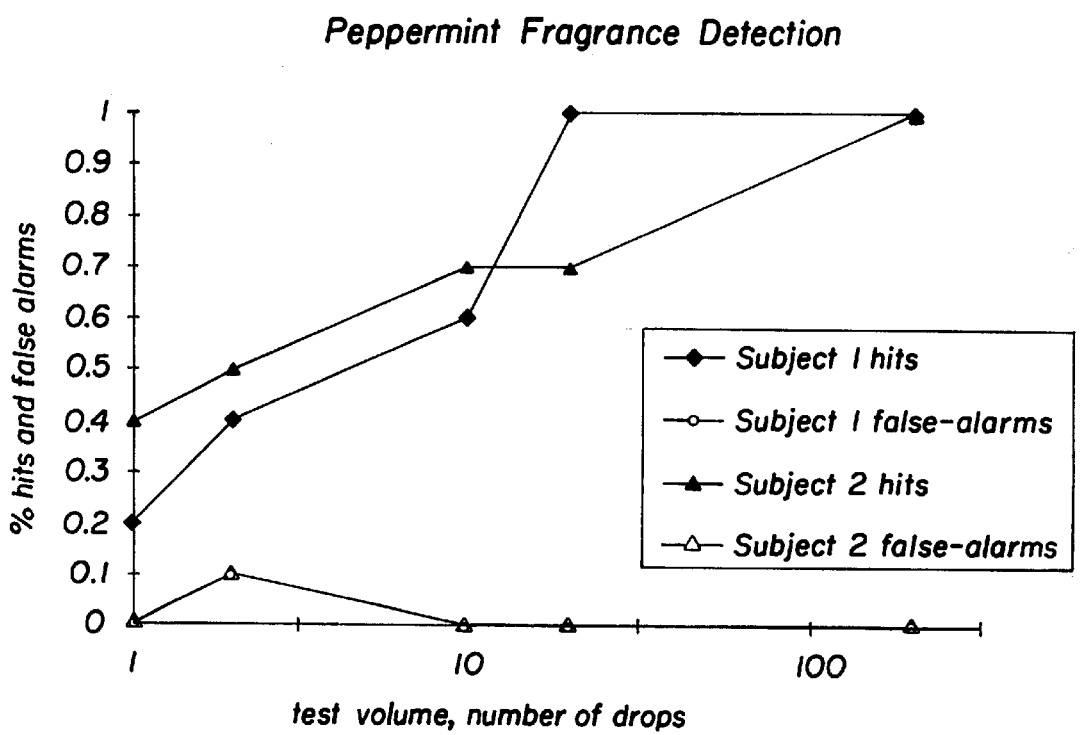
FIG. 21 is a plot of threshold data using an ink-jet-based digital dispenser according to the present invention.

FIG. 21, which is a plot of percent hits and false alarms against number of drops, shows that the hit rates for two subjects were monotonic functions of the number of microdrops, and that the hit rate was substantially above the false alarm rate for odor concentrations as low as 1 or 2 drops (i.e. 91–182 picoliters) of fragrance. (The d' values for the number of drops range from 1.03 to 6.17.) The single 91 picoliter drop corresponded to approximately $10^{-11}$ Moles of peppermint oil (6% w/v soln), i.e., about $10^{12}$ molecules of the volatile substance. These studies demonstrated that microjetting is adaptable to delivery of airborne materials and that the microscopic volumes dispensed by ink-jet methods are ideally-suited to olfactory studies.

EXAMPLE 2

To conduct prototype testing, the chip-based dispenser 52 will be placed in a beaker of water to fill the dispenser with water. The beaker will then be placed in a vacuum that is high enough to cause most of the air trapped in the fluid reservoirs 78 to expand out of the orifices, break free and rise to the surface. When the beaker is returned to atmospheric pressure, the water will be pulled into the fluid reservoirs 78 by the release of the vacuum.

The heating elements 60 will be driven by a 24V DC power supply switched by a solid state relay with less than a 20 $\mu$s response time. Instantaneous current (and thus power) will be measured using a current probe. The heating element 60 electronics will be capable of delivering over 50 $\mu$J of power in pulse durations of less than 20 $\mu$s to the heater element. This capability mirrors the capability of the drive electronics in a conventional thermal ink-jet printing system.

The chip-based dispenser 52 will be mounted in a small chamber which will have temperature and humidity instrumentation. The chamber will also cause the air to remain quiescent during the testing.

Mass transfer rates will be determined by optically observing the fluid volume level as a function of time. A microscope, CCD camera, image capture board, and image analysis software will be used to acquire the data automatically for later processing. The average fluid level will be measured using the image analysis software, and the volume of the fluid will be calculated from the known reservoir geometry, which will have a conical section rather than a cylindrical section of uniform diameter. Mass transfer rates will be determined by plotting the fluid volume versus time curves for the case of vapor phase (nonboiling) mass transfer. For fluid phase (boiling) mass transfer, ejection of the fluid occurs over such a short period of time (less than a millisecond) that it can be considered instantaneous. Thus, fluid phase mass transfer will be quantified on a per pulse basis.

Mass transfer will be characterized as a function of one geometric parameter (orifice area; some devices will have a single 40 $\mu$m diameter orifice, and others will have two 40 $\mu$m diameter orifices) and two electrical parameters (voltage and pulse width). An experiment will be designed with sufficient resolution to construct a response surface for these three parameters.

EXAMPLE 3

Human subjects will be given smell threshold and/or odor identification tests lasting from 30 to 60 minutes, using low levels of pleasant or neutral odors, such as butanol, eugenol, and cinnamon. The protocol will be to have the subjects sniff a test substance and confirm whether or not they can smell it and, if so, to identify the test substance.

Test protocols will involve no more than 8–16 odors to be identified in an odor identification test, and no more than 15–25 up and down intensity steps for a given threshold test, with a maximum of 3 threshold tests per subject.

Fragrances will be presented by microdispensing miniscule amounts into the vapor a subject is asked to sniff. Five minute breaks will be given between tests (more frequently if requested), and no more than 45–60 minutes total testing will be done per subject.

The subject population at SMU will be drawn from the entire student body, which is 95% between the ages of 17 and 23, 52% female, and 22% minorities, of whom approximately 10% are African American, and the remainder are predominantly of Hispanic, Asian, and Native American origin.

The subject population at UC-Irvine will be drawn from normal and Alzheimer's diseased aged subjects, ranging from 55 to 85 years of age. This group is approximately 50% female.

EXAMPLE 4

The digital dispenser 10 of the present invention will permit the probing of new dimensions of human olfaction. The analytical capability of the digital dispenser 10 can be used to understand how olfactory signals are summed over time (to the millisecond range) and (when combined with endoscopic presentation) over the space of the olfactory epithelium. Thus, presenting brief "clouds" of airborne molecules or droplets allows exploration of the temporal integration (approximately 100 ms) and, with endoscopic systems, the spatial integration (approximately 10,000 to 100,000 square microns of olfactory epithelium or the vomeronasal organ) of sensory responsiveness of the olfactory epithelium and the vomeronasal organ (which is specially tuned to pheromones).

The resolution of these basic psychophysical issues will allow the determination of the most reliable and most useful patterns to use for diagnostic work. By injecting miniature "clouds" of airborne molecules or droplets into the inspired airstream, olfactory stimuli can be delivered that are very brief, relative to the overall duration of a voluntary sniff (about 0.5 seconds in duration) or an inhalation (2–4 second duration). This is shown schematically in FIG. 22. Actual examples of such temporal "sculpting" of the gas stimulus are shown in FIG. 7. There will be some smoothing of these temporal functions, due to turbulence as air flows through the nasal meatuses and around the turbinate bones. Retention and release of test substance molecules on the airway surfaces will also produce some temporal smearing of the olfactory stimulus. Still, a temporal dimension will be introduced into olfactory testing by the microdispensing of airborne molecules or droplets into the inlet of the nostrils.

The digital dispenser 10 of the present invention will allow a determination of empirical data such as what temporal patterns of stimulation during a single sniff or single inhalation give the strongest subjective response (i.e., lowest "threshold" or largest d' of a Receiver Operating Curve), how responses from the two nostrils are integrated, what the time-constants are for inter-nostril integration, whether there is an olfactory directional sense, whether there is a dominant hemisphere when dissimilar airborne materials are presented to the two nostrils, whether there is a directionality of olfactory signals due to inter-nostrils differences, whether concentration and duration will be interchangeable (for a fixed total number of airborne materials) over about 600 milliseconds, with little further integration thereafter and whether different airborne materials give different integration functions, as is the case with different adaptation functions for different airborne materials.

The results of these determinations will yield a normative baseline for novel areas of human performance that will provide sensitive indicators of neuropathology. The digital dispenser can be configured as a hand-held device to be used by a clinician in the office (or even in the field) that can precisely probe for within and between nostrils effects. In view of the possibility that olfactory asymmetries could be useful predictors of brain disease, these studies could lead to a practical and powerful olfactory diagnostic tool.

The choice of test substances to be loaded in the microjets 12 include, but are not limited to, pyridine, eugenol, 1-butanol and mercaptan which are commercially available from International Flavors and Fragrances, Inc. as well as some test substances shown to be especially difficult to identify for patients with Parkinson's and Alzheimer's such as cinnamon, chocolate, strawberry and pizza which are commercially available from 3M Microfragrances. Other test substances are disclosed in Table 3 in Amoore, J. E. (1991): Specific anosmias in *Smell and Taste in Health and Disease*, ed. by T. V. Getchell et al., Raven Press, New York, pp. 655–664, the entire disclosure of which is incorporated herein. These other substances include: fruity (isoamyl acetate), etherish (methyl ethyl ketone), camphor (1,8-cineole), clove (eugenol), cinnamon (cinnamaldehyde), minty (1-carvone), thyme (thymol), rosy (2-phenylethyl alcohol), citrous (geranial), floral (phenylethyl methyl ethyl carbinol), lily (lyral), violet (B-ionone), vanilla (vanillin), amber (thujamber), musky (w-pentadecalactone), garlic (allicin), fishy (trimethylamine), halogen (iodoform), burnt (pyridine), phenolic (4-ethylphenol), sweaty (isovaleric acid), urinous (5a-androst-16-en-3-one), repulsive (phenylisocyanide), spermous (1-pyrroline), fecal (skatole), resinous (isoamyl alcohol), gassy (tert-butyl mercaptan), acid (acetic acid), buttery (2,3-butanedione), earthy (2-methylisoborneol), vegetable (methional), cyanide (hydrogen cyanide), malty isobutyraldehyde), sulfide (hydrogen sulfide) and armpit (trans-3-Methyl-2-hexenoic acid).

Still other test substances include: peanut, soap, paint thinner, motor oil, smoke, lemon, menthol, onion, licorice, wintergreen, orange, lilac, grape, gasoline, bubble gum, chocolate, mint, root beer, cherry, strawberry, fruit punch, rose, turpentine, pine, pizza, watermelon, grass, natural gas, cinnamon, pineapple, coconut, dill pickle, clove, banana, garlic, peach, lime, leather, gingerbread, cheddar cheese, musk, cedar, apple, black pepper, chili, tomato, pumpkin pie, skunk, whiskey and honey.

The concentration of test substance and the temporal envelope of presentation, as well as the inter-nostrils differences can all be controlled by merely changing the number of digitally-controlled microdrops to be dispensed into the airstream. In all cases, the maximum mass of airborne materials injected into the airstream will be kept well below the saturation point, so that condensation of the test substances onto the air passages will be minimized.

For a typical logarithmic series of test substance intensities, the dispensers 12 can dispense increasing masses of test substance by increasing the number of drops dispensed. Jetting at 1 to 10,000 drops/second, a single jet 12 can dispense over a 4 log-unit range of test substance intensity in 1 second. For greater temporal compression, jets 12 with differing concentrations can be used. For most test substances, a range of 40 decismels (100-fold concentration range) includes the thresholds of about 98% of all subjects (i.e., ±2 standard deviations), so that 80 decismels (10,000-fold) is more than an adequate dynamic range for the system.

The test subjects will hear an audible "beep," informing them to start an inhalation (or sniff), and the airborne materials will be dispensed at a pre-determined delay after the start of inspiration.

In most of these tests, the dependent variable is whether the subject is sensitive to the stimulus, which can be conceptualized as either a "threshold" (using a threshold model) or as sensitivity, d' (using signal detection theory). In these tests it will be possible to rapidly present any arbitrary airborne material concentration level and any arbitrary duration of airborne material, so the maximally-sensitive approach of producing ROC curves and determining d' for different stimuli is feasible. In these tests it will also be possible to conduct staircase, or modified staircase design threshold tests.

Specifically, tests to determine how airborne material input is integrated over time, can be conducted by taking three temporal envelopes of stimulus (early transient, gradual ramp, and fixed "square wave") with the total amount of airborne material being held constant across all three conditions. These three stimulus "shapes" would then be presented at, for example, 5–10 different overall intensity levels (using steps of 5 or 10 decismels (0.25–0.5 log units)) to see whether the threshold number of molecules for detection (50% level in a staircase design) is systematically different for the three different temporal envelopes. For a single subject, three reversals in the staircase series will be accepted for a threshold determination. Approximately 1.0 hour of subject time would be required for this determination.

The findings concerning the normative baseline data will be extended to a direct pilot comparison of normal and Alzheimer's disease patients. The analytical power of the digital dispenser 10 of the present invention will provide unprecedented sensitivity in detecting the deficits associated with various dementias. These preliminary trials with clinical populations will show the best directions to follow for maximally sensitive diagnostic tests. The more sensitive and accurate testing of olfactory function, achieved by the ink-jet dispenser 10 of the present invention, will yield superior diagnostics. These pilot tests are a first step toward identification of tests that discriminate patient populations from each other and from non-diseased patients. The Alzheimer's disease patients and their age-matched controls will be drawn from subject populations that are already enrolled in programs at the UC-Irvine Institute for Brain Aging and Dementia. These patients will have been given the conventional olfactory test battery described in Kesslak et al., "Olfactory tests as possible probes for detecting and monitoring Alzheimer's disease," *Neurobiology of Aging*, 9: 399–403 (1988) and Kesslak et al., "Quantitation of magnetic resonance scans for hippocampal and parahippocampal atrophy in Alzheimer's Disease." *Neurology*, 41: 51–54 (1991).

There are several mechanisms by which the ink-jet dispenser 10 of the present invention will improve the practice of olfactory diagnostic testing: (1) by making existing tests faster, simpler and cheaper; (2) by making complex laboratory tests simple to run; (3) by making existing tests more accurate; (4) by testing more thoroughly; and (5) by testing new dimensions of olfaction.

The ink-jet dispenser 10 of the present invention will contribute to clinical practice via mechanisms 1, 2, 3 and 4 noted above. The studies to develop and collect normative baseline data and examine temporal characteristics of human olfaction will show the gains in speed, precision, and simplicity.

The pilot studies with patient groups will also explore mechanism 5, namely, the possibility that there are dimensions of olfaction that will show more robust differences among the dementing disease populations and between those populations and normals than do the existing tests.

EXAMPLE 5

The digital dispenser 10 of the present invention will permit a determination of whether tests of inter-nasal stimulus integration are powerful discriminators for detecting Alzheimer's disease.

A "mini-odor-identification" test will be administered consisting of 8 or 16 test substances to be identified. The test substances will be administered using the ink-jet dispenser 10 of the present invention.

The tests will use a bi-nasal paradigm in which a detection threshold is run in the left nostril, another in the right, and a third in which the stimuli are presented bi-nasally. In all cases the subject will be sniffing bi-nasally, from two parallel air tubes. What will vary is whether airborne material is dispensed into the left nostril, the right nostril, or both. The order of the three tests will be varied across subjects, to control for practice and/or adaptation effects.

It is expected that these tests will reveal threshold elevations in the Alzheimer's patients, as has been found in most prior studies. Furthermore, because Alzheimer's central neuropathology is preferentially located within olfactory-processing structures, it is suspected that there may be dramatic deficits in the Alzheimer's group in the bi-nasal integration threshold tests. This is because thresholds using bi-nasal stimulation probably involve a higher-order central olfactory processing than simple unilateral detection. It is suspected that the bi-nasal integration that takes place in the airborne material identification process might also be preferentially disordered in these patients as well. Thus, the improvement in airborne material recognition performance that occurs with bi-nasal (versus uni-nasal) stimulation in normals may be selectively impaired in the Alzheimer's patients.

Aged male and female normal volunteers and patients with Alzheimer's disease (AD) will be assessed for their ability to detect, discriminate and identify airborne materials. Normal controls will receive the Mini Mental State Examination ("MMSE"), a test of general cognitive function, and will have to provide a comprehensive medical history to establish their health. The young group will be between 25 to 45 years of age. The aged group will be between 55 to 85 years of age. AD patients will be 55 years of age or older and diagnosed according to the NINCDS-ADRDA task force guidelines. The diagnosis is based on gradual onset and progression of symptoms, evidence of dementia on the Mini-Mental State Examination, and exclusion of alternate diagnoses by history, neurological examination, MRI or CT scan of the head, and laboratory tests: complete blood count, electrolytes, renal, hepatic, and thyroid functions, calcium, B12, and folic acid levels, and negative syphilis serology. These subjects will be recruited from groups currently enrolled in ongoing clinical programs at the Aging and Neurologic Disease Center at UC-Irvine.

In addition to the standard clinical assessment, the subjects utilized for these test studies of the device 10 of the present invention will be ones that have also been given the UPSIT odor identification test and the olfactory delayed matching-to-sample test. Both of these tests have been evaluated in the Kesslak et al. papers mentioned above and Wu et al., "Olfactory memory in unmedicated schizophrenics." *Schizophr. Res.* 9:41–7 (1993) and found to be sensitive to the pathology of Alzheimer's disease.

It is estimated that the testing of 8 patients (and 8 control subjects) on each of the two tests should take approximately 32 hours of actual testing time.

Thresholds: Threshold testing will be done by a variant of the staircase design, where three detections in a row or three misses in a row will generate a reversal. Butanol, mercaptan and eugenol are suitable test substances for the threshold tests, however, those of ordinary skill in the art will recognize that other suitable volatile substances may be used. The different intensity steps will be ½ log unit steps (10 decismels), and will be produced by driving the microdispensers 12 to dispense from 1 to 1000 microdrops (total 8 intensity levels) in a 500 microsecond burst.

Inter-Nasal Testing: With a microdispenser 12 addressing each of the left and right airways, the left and right nostrils can be stimulated independently or together. The threshold tests will be done three times, once for each nostril, and once for both.

Odor Recognition Tests: This test will use 8 individual test substances, and will be similar to the UPSIT in general design. After a single dispense of a single test substance the subject will be asked which of 4 names best describes the odor. The test substances are commercially available from International Flavors and Fragrances, Inc., and include the fragrances which Alzheimer's patients have been shown to be poor at identifying. To conduct the tests, the test substance solutions will be loaded in microjet reservoirs 16, then a fixed number of microdrops of the test substance solution will be dispensed on demand. For these tests, the dispense-value will be set to be 4 standard deviations (about 25 decismels) above the normal age-matched subjects threshold, as estimated from the data generated in the normative baseline performance tests.

As noted above, the digital dispenser of the present invention can be incorporated into virtual reality (VR) systems. According to such systems, the speed of odor presentation is not generally viewed as a preeminent consideration because odors typically have slow onset and offset in circulating air. However, millisecond-range time delays between the two nostrils have been found to have signal (directional) value in normal subjects. The speed of dispensation of the test substances is important for generating compelling illusions of olfactory space. For example, to simulate the presence of a single point source of odor near an observer, the intensity of the smell should change with head movements or simulated movements through space. A distant source, in contrast, would "appear" as a relatively constant level of odor regardless of relatively small head displacements, and treadmill "walking." The digital dispenser of the present invention, can present any arbitrary spatio-temporal waveform of olfactory stimulation to the subject. The digital dispenser adapted for use in the VR environment is placed on the visor, helmet or face mask of a subject participating in an unencumbered dismounted infantryman simulation training environment.

Human olfaction is exquisitely sensitive: as few as $10^{10}$ molecules of potent odors can be detected by the average human subject. With a substance such as skatol (which is a key odor in excrement), the detection threshold is about $10^{-9}$ $\mu$moles per liter of air. For a moderately strong stimulus like butyric acid (a main component of body odor), about $10^{-6}$ $\mu$moles per liter are needed, with the actual "sniff" using from 0.02 to 0.2 liters.

The feasibility of carrying odors in a compact dispensing device cartridge depends on the amount of material that must be stored. Using butyric acid as an example, it is clear that a strong stimulus (such as 20 decismels (100×) above threshold only requires $10^{-3}$ $\mu$moles of the material in the 1 liter volume needed for several good sniffs. Because the $10^{-3}$ $\mu$moles of material will "scent" the subject's nasal passages for many seconds (1–15 minimum), the strong scent of body odor can be maintained with about 4 "puffs" of odor per minute, or 240 per hour. This uses a total of only 0.24 $\mu$moles of material for 1 hour of a strong body odor. For the liquid, this is about 21 $\mu$g or ~21 nl. Even for 1000-fold weaker stimuli, the fluid volume required is still only 21 $\mu$l for a liquid, or about 210 $\mu$l for a 10% solution. For a system using 10 or 20 different odors, this worst-case scenario still gives only 2.5–5.0 cc of fluid needed for a massive, continuous smell stimulation of all 20 smells at once, all the time. In short, the material required to generate smells can easily be carried on a VR visor, faceplate, or helmet.

In the VR environment, the feasibility of carrying the device must also be considered. The digital multi-channel fluid dispensers of the present invention may have as many as 120 discrete channels per linear inch, with the entire driver for all channels of a 19-jet device being about the size of two pencil erasers. Together with a PROM for logical control and multiplexing of signals, and a small OP-AMP driver, the entire package should not be bigger than 1 cubic inch.

The apparatus can be mounted on a helmet-mounted VR system that interacts with the DIS world. This system can be integrated into a HMMWV/scout rear turret for the operator of a man-slewed 0.50 cal machine gun. By linking to the DIS in a helmet-mounted system the digital dispenser can be incorporated directly into ongoing battlespace simulations. Putting olfactory information directly into the PDU will assign one or more "scent surrounds" to objects in the synthetic environment.

The device of the present invention will be based on existing technology for multi-channel piezoelectric printheads. These devices currently have up to 120 discrete fluid channels per linear inch and print at up to 10,000 drops per second. The main components of the device will be (i) fluid microreservoirs, (ii) piezoelectric fluid jetting devices, (iii) an evaporator "wick" onto which fluid drops will be jetted for evaporation into air, and (iv) power supply and drive electronics.

The fluidic properties of a variety of odoriferous fluids will need to be explored. Fragrance technology and ink-jet technology will have to be combined to produce these fluids.

The main subtasks are as follows:
  a. Selection of ingredients: chemical components utilized to modify fluid properties, such as viscosity or surface tension, will need to be selected for a neutral odor; modified cellulose, polyols, and polysaccharides used as food ingredients will be tested; odorant chemicals will be selected on the basis of vapor pressure, solubility, and efficiency.
  b. Initial formulations: desired odorant chemicals will be formulated into jettable fluids of suitable concentrations and be submitted to jetting characterization. Ambient and accelerated stability testing will be concurrently tested. Formulation development will be iterative.
  c. Formulations will be tested with prototype dispensing device equipment to prove operability and efficacy of odor stimulation.

These studies will establish some basic psychophysical parameters for the digital dispenser of the present invention. The basic psychophysical parameters include identifying:

a. What is the optimum location (relative to the nostril) for the evaporator wick and dispensing jet?
b. What are the thresholds, psychophysical power functions, sensitization or habituation rates when the test substances are dispersed by the digital dispenser in the freely-roaming subject?

c. What spatio-temporal envelopes of odor intensity will properly simulate large versus small spaces and near versus distant sources?

d. Can inter-nasal differences generate localization cues?

A six fluid array print head will be constructed. Each fluid will have one channel, or a total of 6 individually controllable dispensing channels in an array approximately ¼" wide. The key new design development will be a six fluid manifold and miniature reservoirs for the print head and the associated fluid delivery system.

As is well known by those of ordinary skill in the art and as disclosed in U.S. Pat. No. 5,433,809, the entire disclosure of which has been incorporated herein, piezoelectric material (usually lead-zirconium-titanate, or PZT) is prepared initially in a standard fashion: a large rectangular block is formed and a temporary metallization is applied to two sides of the block. A high voltage is then applied across the two metallization layers to orient the piezoelectric properties of the material. Because the design uses the piezoelectric material in shear mode, the poling metallization must be removed. The block of piezoelectric material is then sliced into rectangular pieces that will be formed into individual print heads. These pieces are much larger in two of their three dimensions: 25×25×8 mm and 20×25×0.25 mm being typical for this design, where the former is referred to as the "bottom" PZT and the latter is referred to as the "thin" PZT. Metallization is applied in a batch (i.e., multiple parts at the same time) deposition process to the two large areas of both the bottom and thin blocks. This is the functional metallization that will be used to actuate individual jets. Preparation of the piezoelectric material blocks is performed by the piezoelectric material supplier. These parts are commercially available from Motorola, Hoechst, or Aura Ceramics.

Next, a bottom and a thin block of piezoelectric material are laminated together with electrically conductive epoxy such that their poling directions are aligned. This "sandwich" structure is then machined with a precision diamond saw, creating both fluid channel openings and channel actuator structures. The laminating and sawing operations are well known to those of ordinary skill in the art and are disclosed in U.S. Pat. No. 5,433,809, the entire disclosure of which has been incorporated herein by reference. Both the channel and wall widths for the array to be fabricated according to the present invention will be 200 $\mu$m, and channel depth/wall height will be 400 $\mu$m.

Sawing will be accomplished according to techniques well known to those of ordinary skill in the art and preferably by using a precision diamond saw (commonly used to make ferrite read-write heads for disk drives.

After sawing, a dielectric material such as paralyene or Dow epoxy preferably is used to coat the channels. This layer allows the use of electrically conductive materials in the channel and preferably applied in a layer that is less than 10 $\mu$m thick. Paralyene preferably is deposited using CVD (chemical vapor deposition), while Dow epoxy preferably is deposited using spin coating.

The tops of the channels will be created by attaching a cover plate to the machined sandwich structure. The cover plate will be made of a second sandwich of two plates, both previously machined by excimer laser to create the fluid reservoirs and manifolds. The material of these plates is selected from excimer-machinable, stiff material well known to those of ordinary skill in the art. FIGS. 23A, 23B and 23C show a schematic of the manifold, reservoir assembly. The reservoirs shown would hold about 2–3 $\mu$l of fluid, which is enough to generate 25,000 individual, perceptible "puffs" of odor (using 200 pl drops). Clearly, larger reservoirs could be attached, as needed.

An excimer laser ablation process preferably is used to machine the 6 precision 65 $\mu$m diameter orifices into an adhesive backed polymer film that attaches to one end of the printhead. The orifices are machined to align to the fluid channels when assembled. This array will be fabricated using a projection mask. The back of the channels are sealed with an acoustic energy absorbing polymer. These process steps are well known to those of ordinary skill in the art and are disclosed in U.S. Pat. No. 5,433,809, the entire disclosure of which has been incorporated herein by reference.

When the sandwich structure is formed, the lower piezoelectric block is longer at the rear (i.e., the surface opposite from the orifice plate) of the printhead, thus leaving a metallization layer exposed. The sawing process thus creates individual metallized bonding pads. A flex-circuit will be attached to these pads, allowing the metallization layer in the middle of each channel wall (i.e., actuator) to be individually addressed electrically.

The drive electronics for operating the print head preferably include four sets of 16 channels drivers in one testbed, a controlling PC, and an arbitrary pattern generator. The drive electronics in the eventual productions will be implemented in low-voltage digital logic circuitry and high voltage analog drivers.

To evaluate an individual dispensing channel, a camera and microscope is aligned to observe the droplet formation process while being illuminated by an LED that is strobed at the same frequency as the drops are being formed (10–3,000 Hz). Initial device waveform parameters (pulse timings and magnitude; two timing parameters are required) are selected from test data using isopropanol as a working fluid. The waveform is adjusted to achieve the desired drop velocity and/or drop formation quality (satellite free; trajectory angle). Droplet velocity will be measured by stroboscopically "freezing" the drops in space and measuring the droplet-to-droplet distance ($V=f\lambda$) through a microscope. At low frequencies, when only a single drop is in the field of view of the microscope, the phase of the strobe light will be varied and the velocity will be determined by the distance the drop moves in this time interval (time is measured on an oscilloscope, and $V=\Delta X/\Delta t$). Drop size will be measuring the flow rate of the drop stream over a precise time interval (1–2 minutes, depending on the frequency), and dividing the flow rate by the droplet creation rate.

Once the dispensing devices have been calibrated with isopropyl alcohol, the odorant solutions will be introduced. Drive pulse parameters will be varied to determine the optimal driving pulses for ejecting target-sized drops of odorant. With 65 $\mu$m orifices, the drops will be approximately 80 $\mu$m in diameter. A high-velocity output of 6–10 m/s is preferred in this application, because the goal is to fire odor drops faithfully onto the miniature "evaporation wick" that preferably is located 4–8 mm from the jet orifice. Higher drop velocity will allow a more distant wick and thus, better airflow.

As required, fluids tested in these jets may be modified further in viscosity, surface tension, and other characteristics well known to those of ordinary skill in the art to improve the jetting characteristics.

This evaporation wick is the evaporative/radiator for converting the microscopic liquid drop of odorant to a gaseous vapor that can be smelled. The surface area-to-volume ratio of microscopic drops is so large that the usual problem in jetting of this type is to prevent evaporation in flight. Regardless, a small wick preferably is placed in front of jet orifices, and the jets will dispense onto the wick. Several concepts will be evaluated for the wick. For instance, a conductive mesh (e.g., of nichrome) that can be heated by resistive current flow or a conventional nichrome wire resistance heater surrounded by a suitable, inert "plastic cotton" may be used. The heated wick will be used if applications require smelling materials with low vapor pressure and/or smelling materials in VR environments where the ambient temperature is unusually low.

Wick design evaluation will be conducted by simple psychophysical threshold testing or, for more direct assessment, by taking direct physical measurements of the vaporization process. The latter studies could allow faster and more precise modeling of the evaporative process. Monitoring temperature changes (driven by the evaporative process) at the wick with miniature thin-film thermocouples is one method that could be used for this. Another is to use a model odorant that is a strong UV absorber, and use an interrupted-beam UV photometric method to monitor the actual concentration of gas molecules at various points around the wick. Tests will be conducted to determine how the distance between the evaporator wick and a subject's nostril affects responses. Such tests involve the taking of three distances with the total number of odorant molecules held constant across all three conditions. These three stimuli would then be presented at 5–10 different overall intensity levels (using steps of 5 or 10 decismels (0.25–0.5 log units)) to see whether the threshold number of molecules for detection (50% level in a staircase design) is systematically different for the three wick-nostril distances. Approximately 1.0 hr of subject time would be required for this determination.

An important step in the process is to identify odors needed for a particular synthetic environment. For the battlefield training of the dismounted infantry, smells such as excrement, body odor, burning materials, decaying bodies, and so forth will be some of the smells to be identified.

The Table below shows some typical sensitivities:

| ODOR | DETECTION (mg/M$^3$) | MW | DETECTION ($\mu$moles/liter) |
|---|---|---|---|
| ether | 0.1 | 74 | $1 \times 10^{-3}$ |
| pyridine | 0.04 | 121 | $3 \times 10^{-4}$ (vomit) |
| butyric acid | 0.001 | 88 | $1 \times 10^{-5}$ (body odor) |
| musk | 0.007 | 160 | $4 \times 10^{-5}$ (perfume) |
| skatol | 0.0000004 | 131 | $3 \times 10^{-9}$ (excrement) |

Development of formulations suitable for use in the dispensing device of the present invention will focus equally on satisfying the jetting characteristics which the device requires, and on the odor sensation which the odorant component of the fluid is to stimulate. The fluids will be formulated to have correct viscosity and surface tension for stable jetting, and a stable combination of ingredients to provide adequate shelf-life at ambient temperature without decomposition of the odorants or the formation of precipitates. The basic carrier fluids, where required, will be either deodorized deionized water, or deodorized pure grain alcohol. Any materials selected to control viscosity, or other properties of the fluids, will not be odoriferous.

An example of how test substances may be utilized will be drawn with the chemical 3-methyl indole (skatol), which is water soluble. The detection level of this substance is about $4 \times 10^{-7}$ mg/m$^3$ in air. For a concentration of 100 times the threshold amount (40 decismels re threshold), there would be $4 \times 10^{-11}$ g/l, or $3.05 \times 10^{-13}$ moles in a liter of air. To dispense the correct amount of this odorant into that liter of air in front of a subject with the dispensing device of the present invention, using a nominal drop volume of $100 \times 10^{-12}$l, would require one drop of a 3.05 millimolar aqueous solution. For butanoic acid (butyric acid) calculations show that the detection threshold is below the volume of a typical 100 pl drop. In fact, at 100 times the detection threshold (40 decismels), only $10^{-9}$ moles/l of air are needed. This corresponds to about 90 ng of pure butanoic acid, or about 1 single microdrop (~90 pl).

The above considerations reinforce the perspective that microdrop jetting will give a very sensitive and precise method of stimulating the olfactory epithelia. The entire dynamic range of smell is about 5 orders of magnitude; by dispensing at 10,000 drops/sec, the dispensing device of the present invention could cover most of this range in 1 sec. Loading jets with 1000-fold different concentrations would give even faster "ramps" of apparent increase in odor source proximity. To produce jettable fluids, the following steps will be followed.

Specific subtasks include:
  a. Selection of ingredients: chemical components utilized to modify fluid properties, such as viscosity or surface tension, will need to be selected for a neutral odor; modified cellulose, polyols, and polysaccharides used as food ingredients will be tested; odorant chemicals will be selected on the basis of vapor pressure, solubility, and efficiency.
  b. Initial formulations: desired odorant chemicals will be formulated into jettable fluids of suitable concentrations and will be submitted to jetting characterization. Ambient and accelerated stability testing will be concurrently tested. Formulation development will be iterative.
  c. Formulations will be tested with prototype dispensing device equipment to prove operability and efficacy of odor stimulation.
  d. Both psychophysical threshold testing and direct physical measurements of odorant concentrations will be made.

Beyond the expanding use of olfactory diagnostics in mental health and neurology, additional medical applications of olfactory testing technology are easily envisioned. In clinical practice, the device of the present invention will offer a method for precision dispensing of any bioactive substance into the inspired airstream. Thus, in drug delivery schemes that propose to use the olfactory receptor cells as an entry portal to the brain (bypassing the blood-brain barrier) the digital dispenser system of the present invention would be an ideal way to dispense the target material onto the olfactory epithelium with great precision. This would be especially useful for treating Alzheimer's disease, where the neuropathology is centered in the olfactory related pathways. Other therapeutic uses of odor-environment control would include such uses as (i) providing odor cues for treating acquired food aversions, (ii) odor cues for conditioning or controlling reproductive hormone function (iii) providing real odor cues for teaching, training and conditioning paradigms for both practitioners and clients of health professions. A training CD-ROM that actually presents to the student the odor that they are supposed to learn to identify would be a powerful training tool. Another use of the digital dispenser of the present invention is in delivering metered doses of nicotine to a subject's lungs by inhalation as a part of a cigarette withdrawal program.

Beyond olfaction, the digital "odor-PROM" chip that is incorporated in the device of the present invention can be viewed more generically as a biomedical "fluid-PROM." These fluid-PROM devices could be used for programmable, interactive control of fluid dispensing in a multitude of biomedical applications, including "patch" applications, where the flex-circuit chip could dispense drugs cutaneously in a complex and interactive pattern, and "implant" applications where a fluid-PROM could dispense in programmed, interactive ways (intelligent, interactive "time release") while the miniature unit passes through the digestive system, or rests in situ in a body cavity or organ space.

EXAMPLE 6

Normative baseline data was collected to examine nostril-specific characteristics of human olfaction. The purpose of this example was to obtain normative data on optimal stimulation parameters for robust and reliable human performance testing, using novel stimulus presentation patterns.

Figure 10:
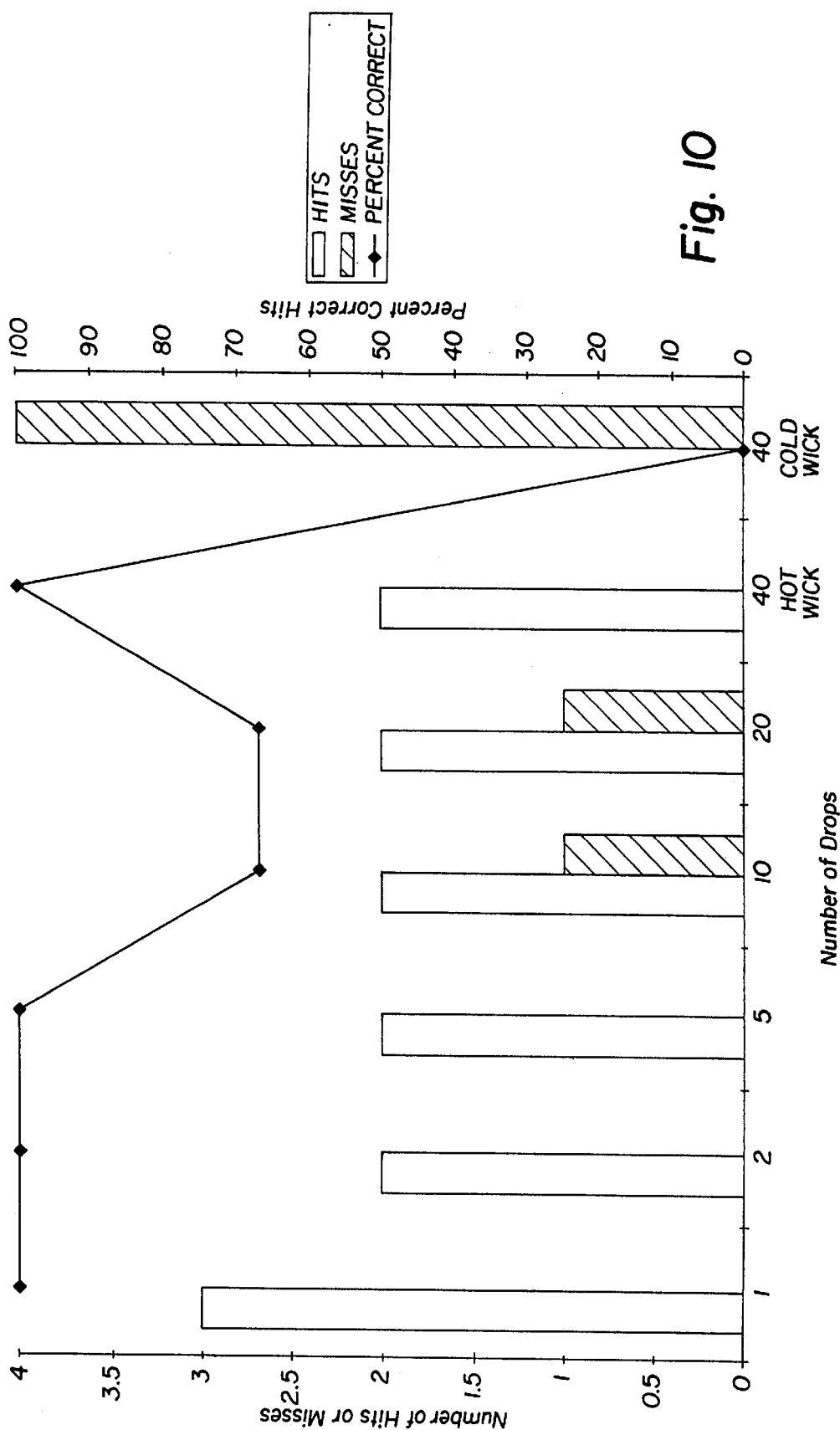
FIG. 10 is a graph of number of hits or misses versus number of drops of ethanol dispensed on the vaporization wick of the ink-jet-based digital dispenser illustrated schematically in FIG. 2.
Figure 11A:
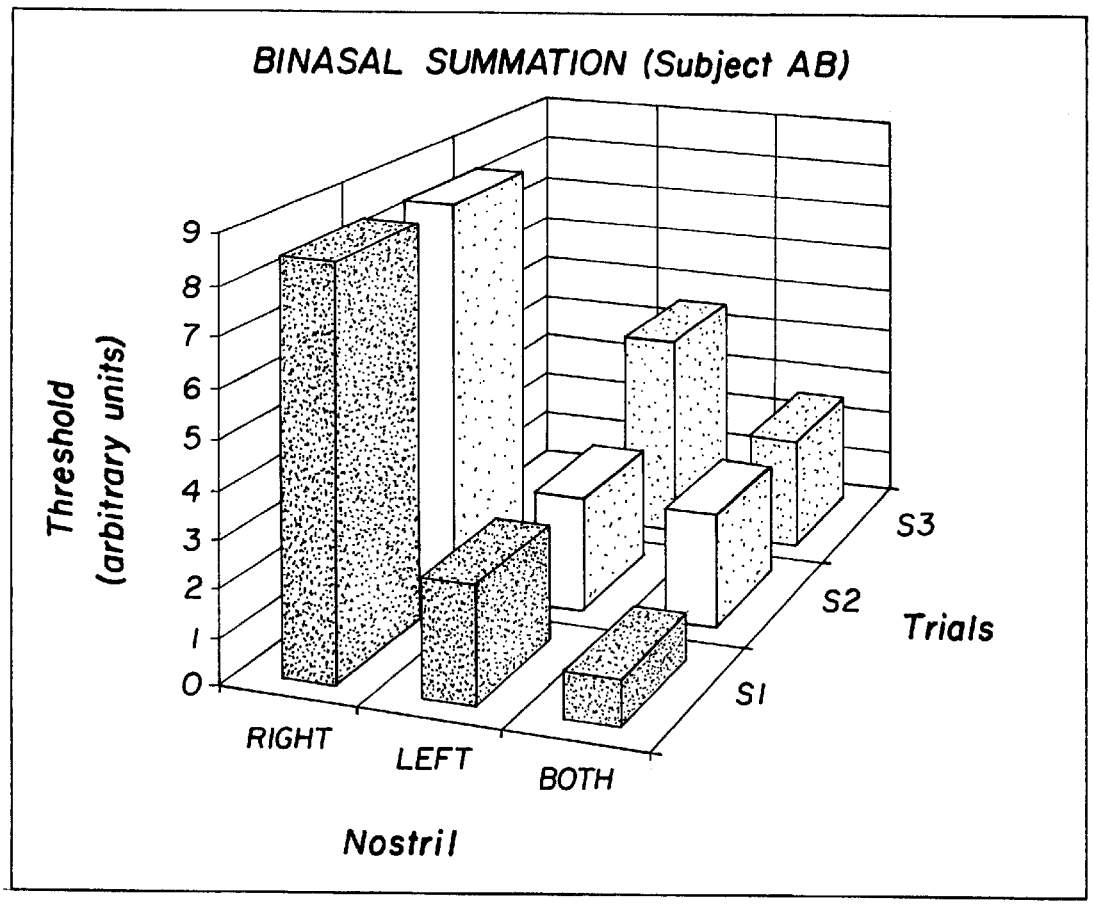
FIGS. 11A and 11B show human subject threshold tests for left, right and left+right combined nostrils conducted on the ink-jet-based digital dispenser illustrated schematically in FIG. 2.
Figure 11B:
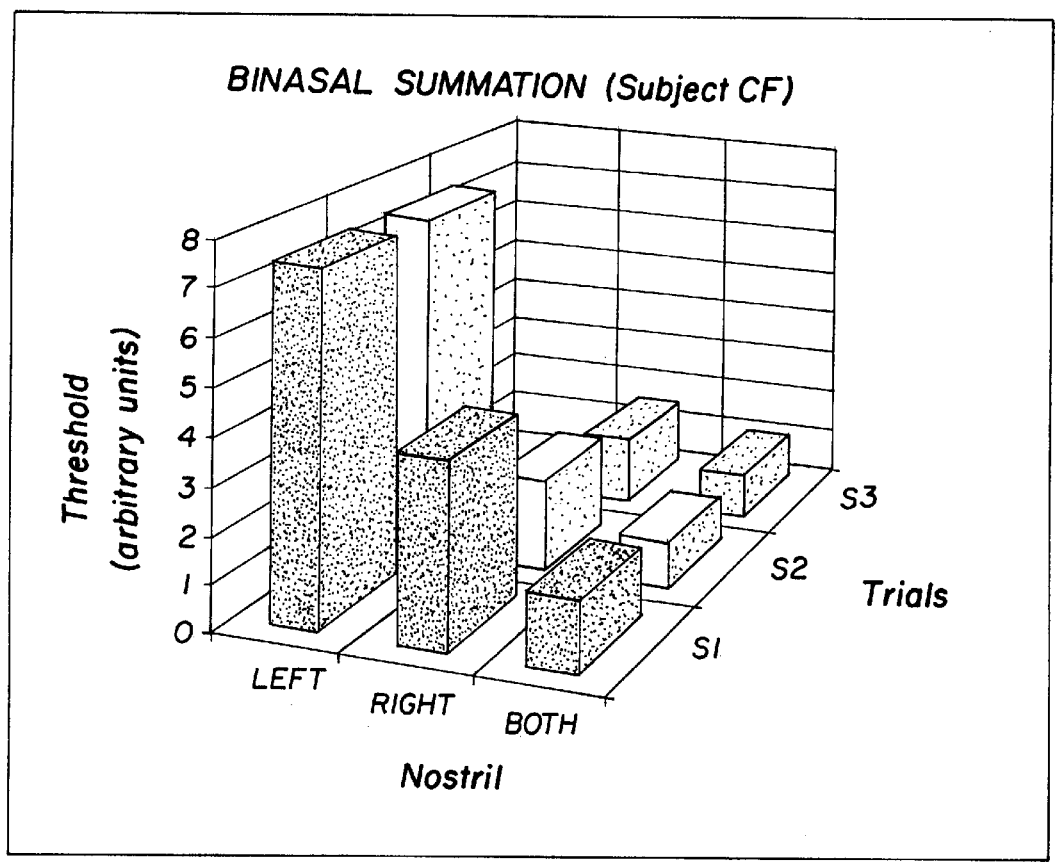
Figure 12:
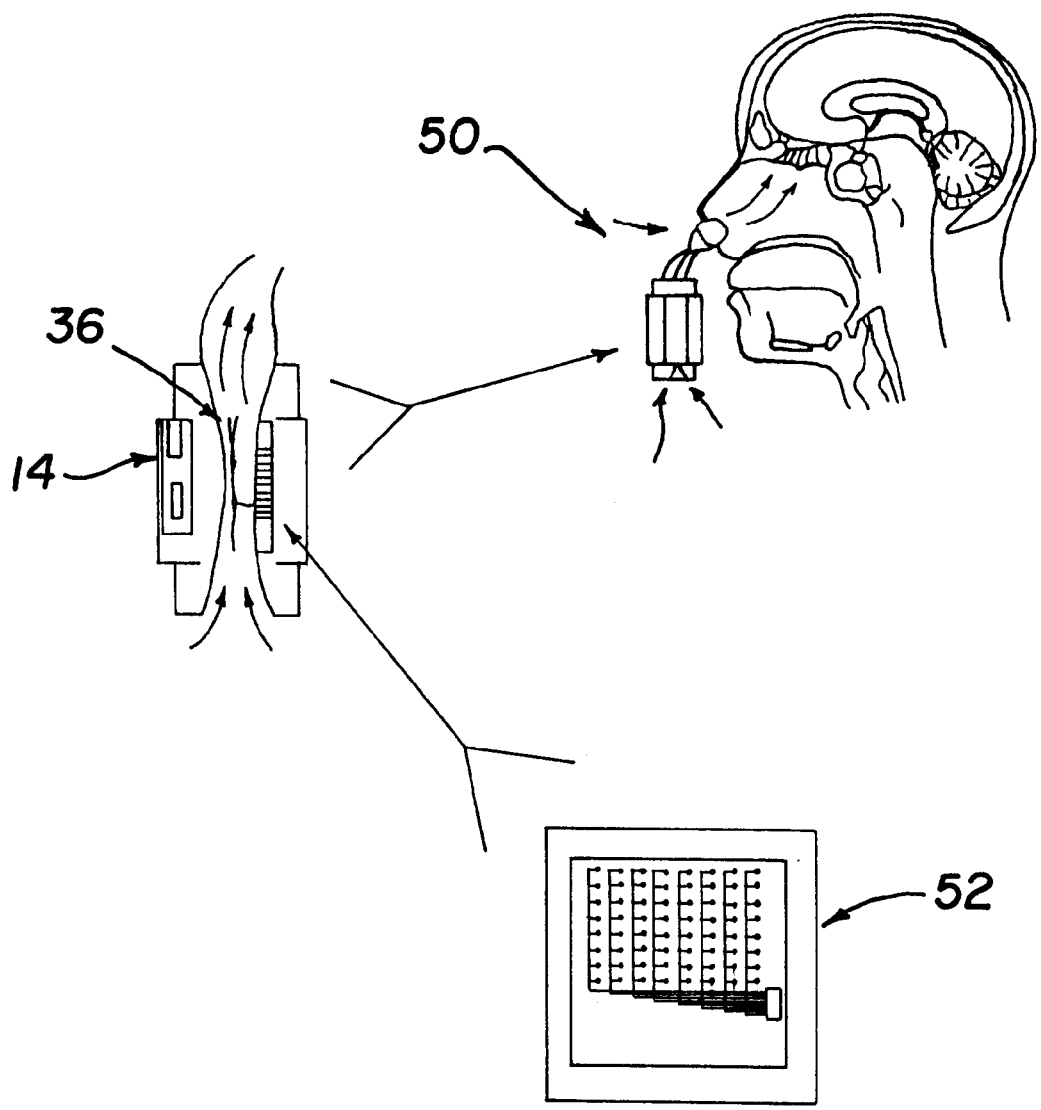
FIG. 12 is a schematic view of a chip-based microdispenser according to the present invention.

Ten normal human subjects were tested with the device according to the present invention shown in FIG. 2. The data collected from these tests are shown in FIGS. 10, 11A, 11B and Table I below.

TABLE I

| Presented/Guessed | Left | Right | Both |
|---|---|---|---|
| Left | 35% | 30% | 35% |
| Right | 40% | 36% | 24% |
| Both | 38% | 15% | 46% |

According to this Example, techniques for obtaining stable thresholds, for obtaining stable measures of bi-nasal differences and bi-nasal summation, and for testing a subject's ability to determine which nostril is being stimulated were developed and tested.

The studies were conducted using the digital dispenser according to FIG. 2. A Receiver Operating Curve technique was used in which stimuli were presented at various intensities (including zero intensity blanks) in random order. Presentations to left nostril, right nostril, and both nostrils were randomly inter-mixed. In all, 10 human subject were tested in various versions of this basic test.

To initiate a trial in these studies, subjects were asked to put their nostrils gently over the two rubber-capped nosepieces, which were alcohol sterilized between tests of different subjects. The soft tissue of the nares against the rubber caps on the airtubes formed a reasonable seal so that the subject's sniffing drew air exclusively through the airtubes. The subject was given a button to press, and at some point after the experimenter said "ready" the subject took a long sniff that had a duration of approximately 1 second. By pushing the button during the sniff, the subject delivered a puff of odor. The press of the button caused the delivery of puffs of various intensity (including zero-blanks) to the left, right, both or no nostrils at the experimenter's selection.

The odorant utilized in the studies was 100% phenyl ethanol (PE). Tests were conducted with an activated charcoal-type fume extractor hood over the instrument, so that stray odor was captured and removed. In some tests, a humidifier was used to humidify the input airstream. The stimulus magnitude (number of microdrops) was varied along a log scale in which 1 minimum "unit" (i.e. increment) corresponded to ⅛th of a Log 10 scale (about 2.5 dS per step). Single steps of this magnitude were used. However, because the human testing units have not yet been calibrated with reference to the actual concentration of odorant gas ascending the airtubes, all results have been expressed as dimensionless thresholds, and are referred to as "units".

In initial tests, subjects were asked to respond "left," "right," "both," or "none" to indicate what stimulus or stimuli they had been given.

The results of the study made it clear that no subject could determine to which nostril or nostrils the stimulus was presented. Table I shows that there was absolutely no correspondence between the nostril of stimulus presentation and the subject's guess about the nostril of presentation. Indeed, Table I shows that the percentage of "hits" (correct determinations of nostril source) was virtually at chance (chance=33%; observed range=35% to 46%) for left, right or both nostril presentations. This finding was expected and confirmed that the test procedure was delivering a "pure" olfactory stimulus, with no detectable trigeminal component.

For measurements of olfactory thresholds, a staircase-type procedure was used in which the test was started with a staircase series from stronger to weaker, and the subject was required to give a "yes" or "no" on each trial. In these experiments, it was found that some subjects had thresholds below a single drop (100–200 pl) of the PE. Accordingly, the stimulus was switched to 1% PE in deionized water. Several variants of the basic staircase method were used: staircase reversal after 1 "no" or after two "nos" or after one "yes" or two "yeses" were tried. Generally, three transitions were sought, with each Yes-No transition used as a single threshold estimate. Presentations to the left nostril and to the right nostril were mixed together randomly, with blank trials approximately every 2–3 trials. In some tests the presentations to both nostrils were intermingled with the tests of single nostrils, with all three presentation modes mixed together at random. In others, the testing of both single nostrils was done first, with the bi-nasal presentations done at the end of testing.

Representative results for the normal subjects are shown in FIGS. 11A and 11B. All subjects showed an inter-nasal difference in threshold, and some (typically with a self-identified sinus congestion at the time of testing) showed vast inter-nasal differences, some large enough to preclude testing of one nostril.

The summation of sensory inputs from the two nares was definite in all of the subjects that were tested for summation. This is shown for two of the normal subjects in FIGS. 11A and 11B. For both subjects, this summation meant that the average threshold for bi-nasal presentation was consistently lower than that for either nostril tested separately. The effect was especially striking since the puff presented to the less sensitive nostril was as many as 4–6 steps in strength below the measured threshold for that nostril tested alone. Even puffs several steps below detection threshold contributed to bi-nasal summation.

EXAMPLE 7

The aim of Example 7 was to compare normal and Alzheimer's diseased patients on an olfactory test utilizing the digital dispenser shown in FIGS. 3A and 3B.

Figure 24:
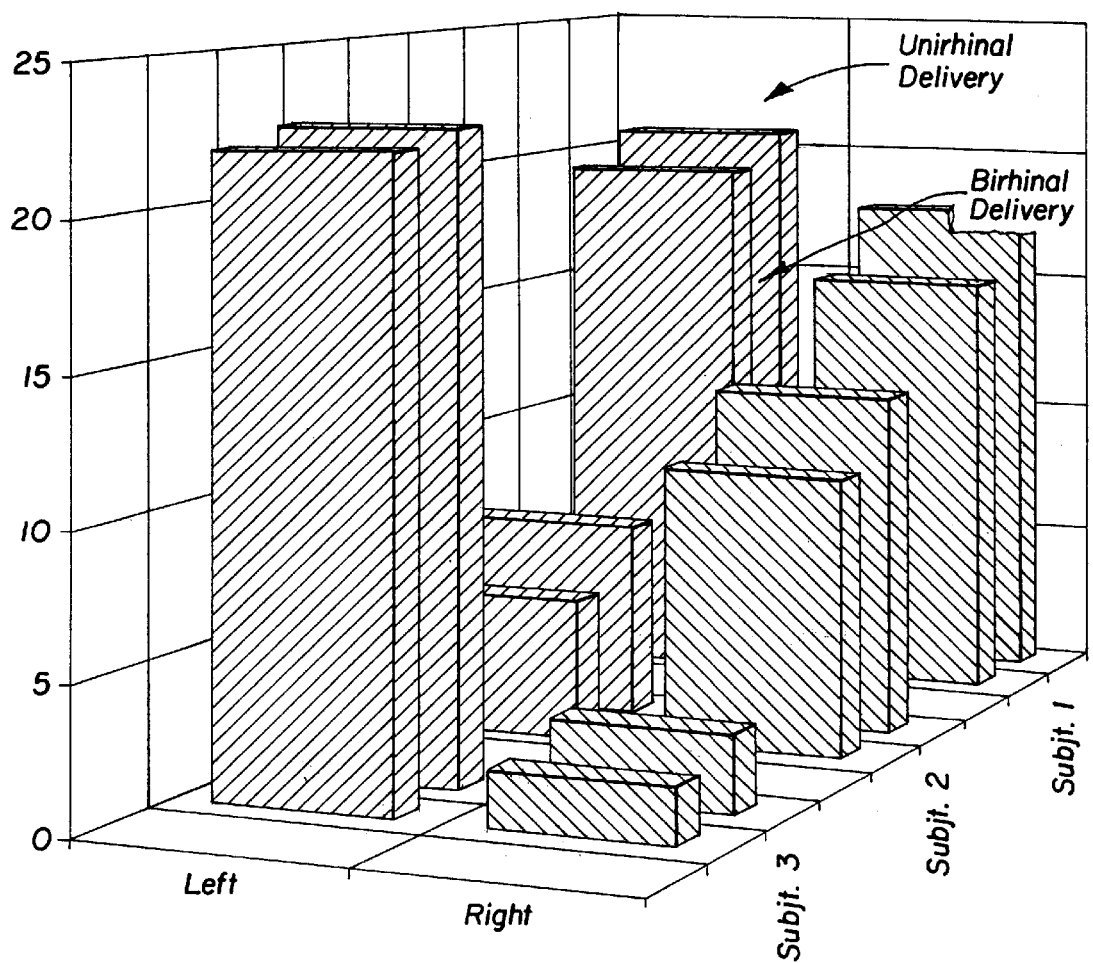
FIG. 24 shows human subject threshold tests for left, right and left and right combined nostrils conducted on the ink-jet-based digital dispenser illustrated schematically in FIGS. 3A and 3B.

The results of the tests conducted according to Example 7 indicated an apparent substantial difference between 4 Alzheimer's subjects and three normal controls. The control subjects gave results quite similar to those obtained with the non-aged controls in the testing of Example 6. All three subjects showed clear internasal summation, with the apparent threshold for bi-nasal presentation consistently lower than that obtained when either nostril was tested separately. These results are shown in FIG. 24.

Figure 25:
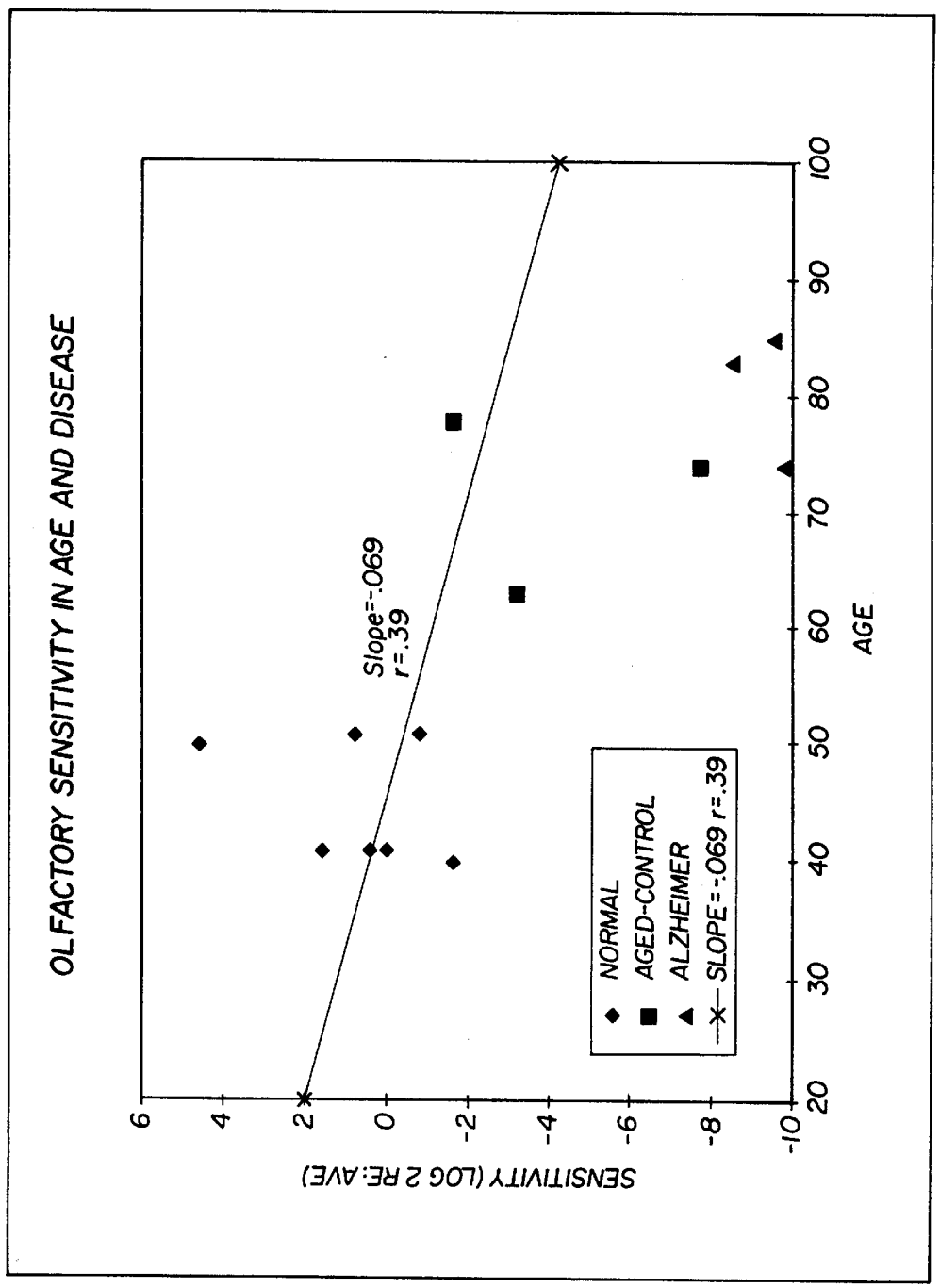
FIG. 25 shows human subject threshold tests for left, right and left and right combined nostrils conducted on the ink-jet-based digital dispenser illustrated schematically in FIGS. 3A and 3B.

None of the four Alzheimer's patients could detect the odor puffs consistently enough to even generate a threshold. There was some uncertainty about the uniformity of the puff generation for the first patient, but the data from the latter three patients are shown in FIG. 25. Two of the subjects were completely unable to detect the stimulus at the maximum strength that could be delivered, even using both nostrils. The third was unable to discriminate stimuli from blanks at any of the intensities tested, which included all but the highest intensity.

EXAMPLE 8

Modeling of Vapor Cloud Flow in Moving Airstreams

Figure 26:
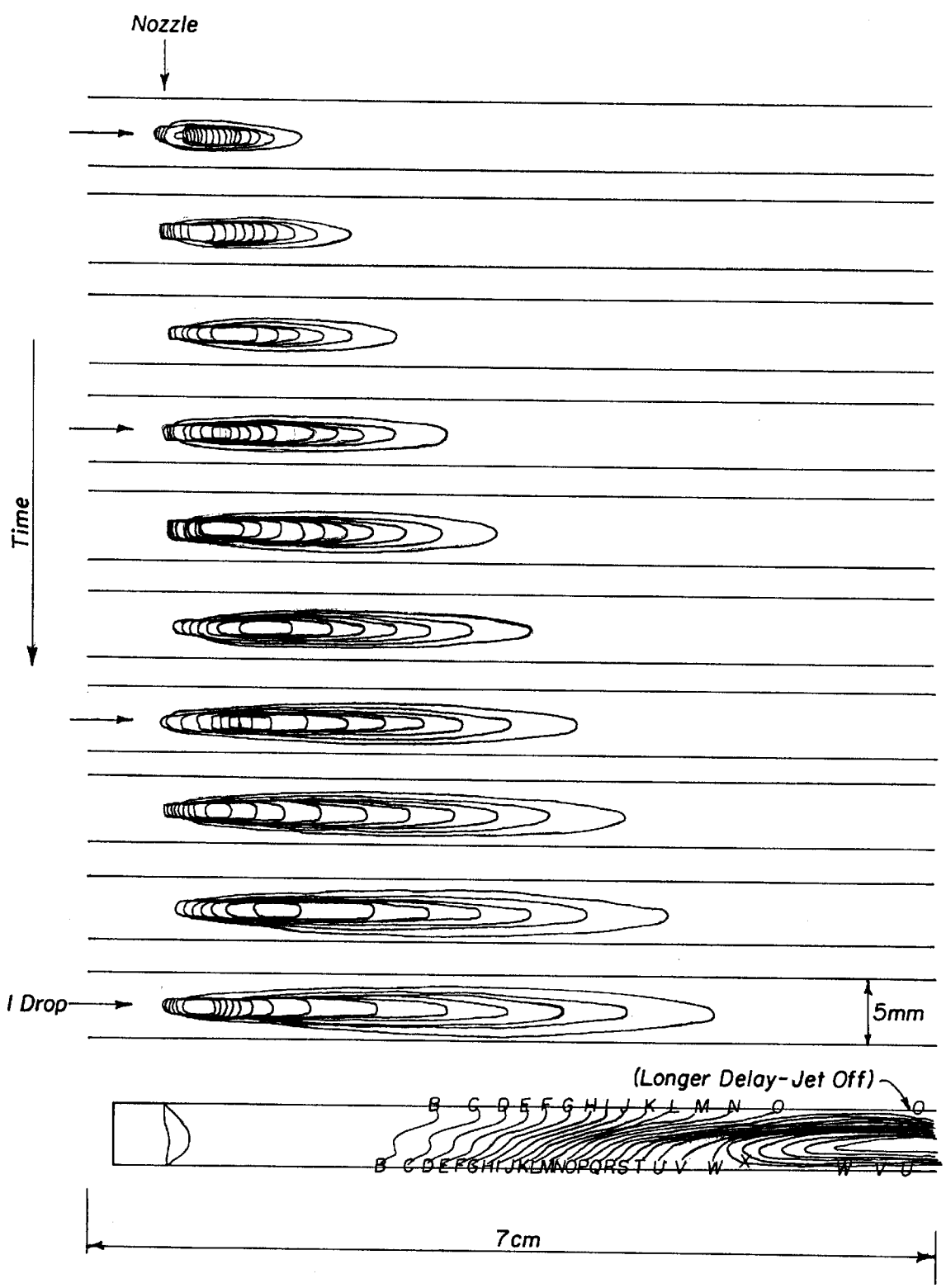
FIG. 26 is a schematic view of the dispersion of an olfactant in an airtube.
Figure 27:
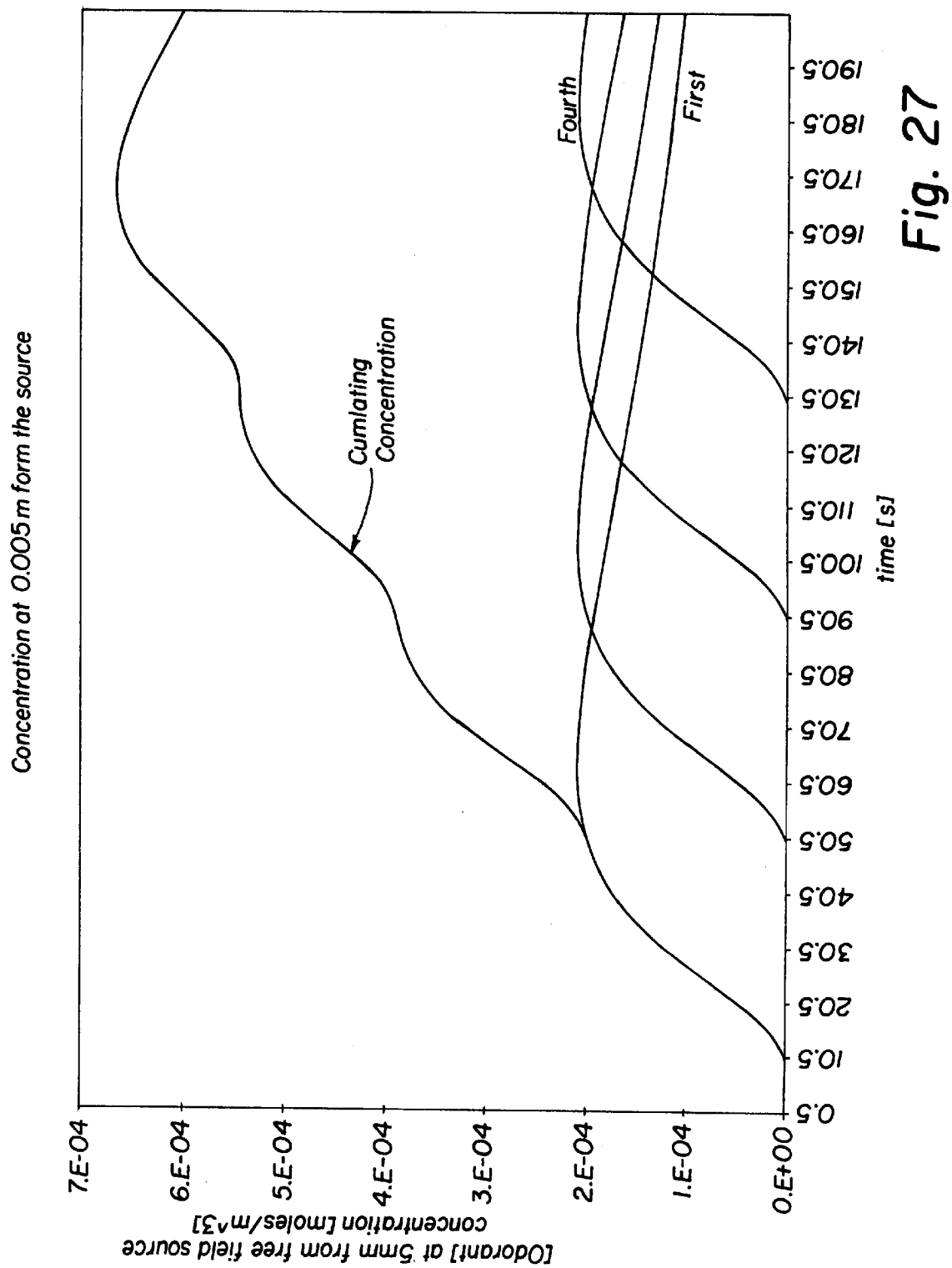
FIG. 27 is a graph of the concentration of an olfactant versus time at 0.005 m from the source of the olfactant.

To deliver olfactory stimuli accurately, the dispersion of the olfactant that will occur as it moves in the airstream must be takeii into account. Several revealing (and counterintuitive) findings emerged in the trials conducted according to this Example. First, the speed of diffusion is sufficiently low so that with a modest airflow (1 m/s) the airflow virtually completely dominates the spread of the vapor cloud. As shown in FIG. 26, in a 7 cm long air tube having a 5 mm diameter, the radial diffusion is so slow that there is incomplete mixing radially at the end of the air tube. As shown in FIG. 26, the images represent successive 5 msec intervals, starting at the top. Odorant is injected (70 pl) at the tube inlet (arrow) and the 1 m/s airflow is from left to right. Four successive 70 pl input drops are jetted during the 50 m/sec period shown in FIG. 26. FIG. 26 makes it clear that forced air flow completely dominates dispersion with a radial gradient still present (i.e. show diffusion) even at the right-most end of the tube. The second interesting result is that it is a physical impossibility to maintain a uniform concentration of odorant at a fixed distance from the source, En by passive diffusion alone as shown in FIG. 27. Some airflow is required if a uniform concentration from a constantly-emitting source is desired.

EXAMPLE 9

Development and Construction of Clinical Testing Systems for Olfaction

1. The 8-fragrance piezo-electric test system will be similar in design to the apparatus shown in FIGS. 3A and 3B. The system will be reliable enough to produce trustworthy, parametric data yet versatile enough to allow a wide variety of psychophysical or psychological tests of patient populations. An enhanced version for analytical research could include such features as built-in odorant waveform monitor (IR), built-in flow meter (reed type), and control circuitry to allow constant-concentration and systematically varying concentration. These units will include drive electronics, interfacing to a palm-top PC, and control software. The drive electronics and interfacels) will be exterior to the hand-held unit.

8-fluid Capability—The design of an eight fluid system will be an expansion of the apparatus shown in FIGS. 3A and 3B, requiring eight jets and associated drive electronics. For a maximum of two odors presented simultaneously, only two pulse former and amplifier circuits will be needed. Each jet will have a separate, coiled-tube reservoir. Each of the jets will be individually calibrated to the particular odorant it will use. Empirical testing and some quantitative modeling will be required to find the best mounting and interconnects compatible with good piezojet acoustic wave jetting.

The drive electronics for each jet will control the number of drops of odorant independently, in order to jet multiple fluids simultaneously at various ratios. This may be done on-line by collecting jetting into the open orifice of a calibrated microcapillary tube, measuring the length of tube filled by 1500 drops. The formation characteristic of individual drops will be monitored by strobe illumination of emerging drops and high-speed video microscopy.

Easy and Reliable start-up—As with conventional ink-jet printers (e.g., Hewlett Packard, Canon) the piezo-fragrance if jet will likely require some attention at initial start-up. To improve start-up, techniques well-known to those of ordinary skill in the art will be explored such as nozzle wiping (by rotating a simple rubber cuff across the nozzles), nozzle sealing after initial loading (by storing the system with a rubber "dam" across the nozzles) and purge cycles at start-up. Reliability data will be gathered by doing simulated "start-up" trials and recording success/failures. "Start-up" data on the apparatus shown in FIGS. 2, 3A and 3B is actually quite favorable (80%+success).

Failure Rate Less Than 5% During Subject Testing—To keep jet failure during a test to an absolute minimum, we will use industry standard procedures well known to those of ordinary skill in the art. The only causes of jet failure occurring more frequently than about once per 10,000 drops are particulate impurities and gas bubbles. Filtering through a standard chromatography frit will remove particles from the odorant. Thorough flushing of the reservoirs with a laboratory-grade detergent followed by a high pressure rinse with de-ionized water removes particulates. To further insure against surface tension induced bubbles, the reservoirs can be provided with specific odorant compatible hydrophilic coatings and the fluid can be degassed.

Improved Wick Geometries and Thermal Characteristics—Wick temperature, wick materials, and wick size have been determined to affect the efficiency and rapidity with which the odorants vaporize, thus affecting the temporal characteristics of the stimulus. The suitable wicks preferably are inert and produce no odor when heated to 200–400° C. during pre-experiment cleaning cycles. The surface of the wick preferably is highly wetting to "pull" the fluid out into a thin film as it lands on the wick. Also, the surface area preferably accommodates up to 40 nl of fluid in a thin film for rapid flash boiling. Finally, the wick preferably has either a large enough thermal inertia or a high enough gain in the temperature control loop so that neither the arrival of drops nor the flow of air during sniffing appreciably alters the temperature of the wick. Preferably, the wick comprises two miniature thermistors coated in molded porcelain.

Known and Stable Relationship Between Drops Dispensed and Vapor Concentration at Exit Tube—This is a key performance requirement, without which the system cannot measure thresholds in a meaningful way. The controlling factors are the wick characteristics above and the fluid wetting and boiling properties. Vapor efflux under constant air flow conditions will be monitored by IR absorptiometry, and the fragrance drop volumes will be varied by controlling drop number and rate. Wick properties and conditions will be investigated to maximize rapid, uniform gas generation across the range of fluids and volumes that will be used for the tests. The system preferably will be linear over a psychophysically-relevant range (0–40 dS).

2. Odor-PROM Chip Device—This is a chip-style unit in which individual stimuli (including different odors and different strengths of same odors) are stored in wells, up to 500 per sq cm. The wells will be preloaded and preprogrammed to generate specific clinical diagnostic tests. These units also will include drive electronics, interfacing to a palm-top PC, and control software. The drive electronics and interface(s) will be exterior to the hand-held unit.

Printed Circuits—The floor of the multi-odor array will consist of a sheet of 0.004 inch polyimide. Printed onto the top will be one set of 30 parallel, gold-plated leads (0.002 inch width; 0.016 pitch) running north-south and a second set of 30 parallel leads overlying the first running east-west. Insulation (printed prior to printing the second set of leads) will separate the leads as they cross over at every junction, but the rest of the lead surfaces will all be exposed. The odor wells will be excimer-machined through a sandwich of 0.012 inch polyester backed by 0.002 inch adhesive, as noted above with commercially available equipment from Neuman Micro Systems, Inc.

To assemble the wells, the adhesive will be exposed on the bottom of the wells, and the wells will be bonded to the polyimide "floor" section, with the "+" shaped intersection of two leads centered in the bottom of each well. Voltage applied to any single E-W lead and any single N-S lead will cause current-induced heating of the single well at that intersection.

Top sealing Material—The material used to seal the wells preferably (i) is durable and stable enough to keep wells sealed, (ii) has a sufficiently strong pressure-bond adhesive on the lower face, for bonding the fluids into the wells, and (iii) is sufficiently brittle that it can be burst by the pressure transient that will be generated by vaporizing the odorant fluid. Candidate materials for this are 0.001–0.0005 inch thick polypropylene, polyester, or acrylic. In a "worst case" scenario, in which no material can be found that meets all of the criteria, then a second step of excimer machining will be added to the manufacture procedure, this time from the top. The top of each well will be separated from the adjoining wells by simply cutting cross-hatch patterns through the material used for the top. Essentially complete, volumetric emptying of single wells can be obtained by this "popping" method.

3. MiniJet—This unit will be compact and non-magnetic having one or two odor capability. This unit will be used for generating stimuli for evoked potentials and for fMRI studies. For both fMRI and evoked potentials, it will be especially useful to be able to selectively present one or the other odor, or odors to one or the other nostril, automatically. In this way, subtraction of one response from another can isolate response components that are unique to one odorant, or are seen only in one hemispheric processing and not in the other.

EXAMPLE 10

Assess the Diagnostic Power of the Olfactory Test System

1. Overview

These studies will be designed to determine the clinical impact of the apparatus and methods according to the present invention. If olfactory testing proves to be a cost-effective way of improving the speed, economy, sensitivity, or specificity of tests for Alzheimer's disease or other neurologic diseases, this will be a direct and major contribution to mental health care delivery.

The apparatus and methods according to the present invention have demonstrated that olfactory testing can improve the certainty of the diagnosis of Alzheimer's disease. These studies will be conducted to determine what test(s) can be the most powerful in actual use.

2. Detailed Methods a. Test selection

The ideal olfactory diagnostic test would be a test that would identify all subjects destined to develop Alzheimer's dementia (100% sensitivity) yet falsely label no normal subject as "pre-Alzheimer's: (specificity 100%). However, short of that "perfect" test, a realistic good outcome would be a test that has a favorable sensitivitylselectivity ratio and is minimally redundant (minimally correlated) with existing cognitive and behavioral measures. The latter would ensure the largest increase in diagnostic certainty from the additional tests.

To minimize redundant overlap and potential confounding with verbal tests of fluency, verbal (semantic) memory, and episodic memory, tests will be evaluated that do not invoke odor naming, odor name recognition, or retention of either odor quality or odor name for periods long enough to tap (with distractors) episodic memory function.

However, some olfactory tests will be included that do involve verbal semantic or episodic memory components. These will be conducted using the apparatus according to the present invention. The purpose in using these "mixed" memory+olfaction tests is for comparison with "gold standard" olfactory tests that are already known to be sensitive to the Alzheimer's pathology. Several such tests are under consideration. One is simple odor identification, as in the UPSIT. (Kesslak, J. D., et al. (1987) Olfactory Tests as Possible Process for Detecting and Monitoring Alzheimer's disease. *Neurobiology of Aging*, 9: 399–403, the entire disclosure of which is hereby incorporated herein by reference.) A more sensitive variant of that test is one developed by Barbara Kelly (Kelly, B. Odor Detection, Odor Quality Discrimination and Odor Identification in Early Alzheimer's Patients. Ph.D. Dissertation, York U., North York, Ontario, 1994), which requires subjects to pick the named odor from a pair of odor stimuli, with a 10-second delay interposed between sampling the two test odors. This test has yielded virtually chance performance in Alzheimer's patients, as compared to almost perfect performance among normal aged. A similar test (delayed matching to sample with odors having familiar names) has also been found to be highly sensitive to Alzheimer's symptomology. Indeed, it has been found that extending the delay between the two test odors up to 30 seconds reveals an even bigger deficit among the earliest stage Alzheimer's patients.

Three specific tests of olfactory ability have been identified which are believed to be sensitive to emerging Alzheimer's pathology but insensitive to episodic or verbal memory demands, as conventionally tested.

These three tests, listed below, represent different levels of information processing from essentially "pure" olfactory sensory tasks to more complex memory tasks. All of these tests can be conducted quickly and precisely by utilizing the novel capabilities of the apparatus of the present invention.

b. Specific Initial Tests i. Test Thresholds for Different Odors with Different Duration Stimuli These tests are chosen because of the mounting evidence that Alzheimer's patients may have an early, odor-selective, hyposmia. Extremely brief stimuli may exaggerate this Alzheimer's deficit. Therefore, odor duration will be crossed with specific odor quality in a quest to find the most sensitive quality and duration combination.

ii. Test Thresholds for Two Different Odors Presented to Two Nares Simultaneously This test forces the central olfactory system to sum inputs from different glomeruli (see Buck, et al., "A Novel Multigene Family May Encode Odorant Receptors: A Molecular Basis For Odor Recognition" *Cell*, 65, 175–187, the entire disclosure of which is incorporated herein by reference) and from the two olfactory bulbs in the task of threshold detection. This neuro-computational task can only be performed after the pathways converge at the pyriform or entorhinal cortex (or higher) in the CNS. The emphasis with this test is not the inter-nasal differences (which largely reflect the capricious asymmetry of nasal airway patency), but, instead, is the CNS capability to sum together disparate inputs for detection. It is suspected that this "highest order" olfactory task might be sensitive to the olfactory system pathology of Alzheimer's.

iii. Same-Different (Match-to-Sample) Tests with Delays of 0 to 120 Seconds, Using Odors Without Common or Familiar Name These tests were chosen because the work of others in the art (Kelly, B. Odor Detection, odor quality discrimination and odor identification in early Alzheimer's Patients. Ph.D. Dissertation, York U., North York, Ontario, 1994; Amoore, J. E. (1997) Diagnostic Aid in Alzheimer's, Parkinson's, Brain Swell Test Kits, the entire disclosures of which are hereby incorporated by reference) indicate that the olfactory sensory memory ("odor image" memory) is selectively impaired in Alzheimer's. This is the quintessential example of a task that is "purely olfactory" but still complex enough to demand high-level central olfactory processing.

c. Testing Methods

Olfactory tests will be performed in a well-ventilated space, with minimal distractions. The tests will all be kept under 30 minutes, so that subject fatigue and stress are minimized. The tests will all be done by having the subject sniff at the air tubes for an approximate one second sniff during which time the subject presses a button. By pressing the button the apparatus either does or does not dispense a "puff" of odorant (to either or both nares). A lap-top or palm-top type computer will be used to control the micro dispensing device and to record the subject's responses.

The subject then answers either "yes" or "no" to indicate whether he/she detected an odor (threshold tests) or whether the odor matched a previously-presented odor (match-to-sample) or a previously named odor (odor identification/recognition tests). For threshold testing, the subject will be presented with pairs of trials (one a stimulus and one a "blank"; given a minimum feasible delay) and will be asked to say which of the two was a stimulus and which was the blank. The threshold will be defined as the lowest intensity at which the subject scored 100% correct. Tests done for comparison with the UPSIT or the OlfactoLabs odorant bottle equipment (see Amoore, J. E. (1997) Diagnostic Aid in Alzheimer's, Parkinson's, Brain Tumor, Head Trauma, Olfacto Labs Publication, Quantitative Smell Test Kits, the entire disclosure of which is hereby incorporated herein by reference) will be conducted according to the conventional manufacturer's instructions.

d. Subject Selections

Three subject pools will be used. Two subject pools will be populations of Alzheimer's diseased patients and their age-matched controls drawn from existing clinic populations of the University of California at Irvine (UC Irvine) and the Florence (South Carolina) Neurological Clinic. The third will be drawn from the McLeod Regional PeeDee Valley Study on Aging, a sample of several hundred elderly people drawn from a population of 5000 regional subjects.

Three types of subjects will be tested, (i) Normal Aged, (ii) Alzheimer's patients in the earliest stages after diagnosis, and (iii) age-matched subjects whose memory performance is impaired (lowest ⅓ of the memory test scores), but who are not within the "dementia" range.

This latter group has already been identified within the PeeDee Valley sample in South Carolina. It is assumed that some of this last group will be diagnosed with Alzheimer's within 1–2 years. Thus, the olfactory tests according to the present invention can be evaluated in a prospective framework with these subjects allowing evaluation of subjects in an early transition stage of disease.

Diagnosis of Alzheimer's disease will be made among 5 patients categorized according to the NINCDS-ADRDA criteria and examined at the UC Irvine Alzheimer's disease Clinic or the Florence Neurological Clinic. Subjects with Alzheimer's disease will be in mild-to-moderate stages of dementia with Mini Mental State Exam scores between 12–24. Control individuals are determined to be healthy using a medical history and cognitively intact through clinical interview. Diagnostic evaluations for dementia included neurological, psychological, laboratory and imaging exams. MRI scans are done within two weeks of the psychometric testing and neurological exam. Other laboratory tests routinely done for evaluation of the Alzheimer's disease patients include a CBC, chemistry panel, B-12, folate, MHA-TP serology, thyroid functions, chest X-Ray, EKG, CSF for cells, glucose, protein, and VDRL, urinalysis, EEG, and HIV when a risk factor is present. Classification of patients is according to the NINCDS-ADRDA criteria for Alzheimer's disease and based on clinical impressions of the neurologist and neuropsychologist.

EXAMPLE 11

Examine Central Nervous System Processing of Olfactory Stimuli by Event-Related Potentials and fMRI The apparatus of the present invention provides a new way to probe brain function with metabolic or electrophysiologic tests. Inasmuch as the classical rhinencephalon (olfactory bulb-pyriform and entorhinal cortex, hippocampal formation, amygdala) is the site of some of the most extensive damage in Alzheimer's disease, it is plausible that direct probing of the physiologic/metabolic function of those systems could be a sensitive probe for the earliest signs of incipient Alzheimer's disease.

The purpose of these studies is to determine whether robust and marked electrophysiological or metabolic signs of dysfunctional olfactory signal processing can be found in the brains of Alzheimer's diseased patients. Finding such physiological signs would (i) shed light on the fundamental nature of the Alzheimer's pathology and (ii) potentially generate a diagnostic test for presymptomatic identification of pre-Alzheimer's patients.

The apparatus of the present invention can generate optimal stimuli for both event-related scalp potentials (ERP) and functional magnetic resonance imaging (fMRI) of cerebral metabolic responses. In the former case, a subject breathing normally through the nose can be given a discrete, single "puff" of odor at any point in the respiration cycle. The leading edge of this "puff" is believed to be fairly sharp, thus generating a clean, time-locked cerebral potential. The presentation of the odorant can be controlled either by the subject (thus adding premotor and motor events to the ERP) or by the experimenter. Different fragrances and/or intensities and hemisphere (olfactory bulb) of presentation can all be provided arbitrarily, by the experimenter's simply firing different jets.

The apparatus of the present invention can also be fabricated in a non-ferrous, non-magnetic version for use in fMRI. With the subject breathing through his or her nose, the fragrance jet can be used to turn on and of f one or more fragrances in either or both nostril(s). A steady-state aroma level can also be maintained for as long as needed to accumulate informative metabolic images.

Detailed Methods Scalp Evoked Potentials

Both a Standard, Constant Flow Olfactometer (Evans, et al. (1995) Chemosensory (Olfactory) Event-Related Potentials in Normal Human Subjects: Effects of Age and Gender. *Electroencephalography and Clinical Neurophysiology* as: 293–301; Evans, et al. (1995) Olfactory Event-Related Potentials in Alzheimer's Disease; 18*th Annual Meeting of the Association for Chemoreception Sciences*) and the apparatus according to the present invention will be used to generate the stimuli. It is anticipated that the two technologies will be combined to use the apparatus according to the present invention to inject odor "puffs" into the airstream of the constant-flow olfactometer. This "hybrid" machine may prove to be the best system, combining simplicity with constant-flow precision. Individual subjects will be tested with each method, in a single setting.

Constant Flow Olfactometer Stimulus

The conventional olfactometer features: 1) tandem, three-way electromagnetic solenoid valves which switch between continuous streams of odorous and clean air; 2) pressure regulators and relief valves at the input and exhaust ports of the solenoid valves to reduce fluctuation in pressure and volume flow rate with solenoid activation; 3) a "carrier" flow of humidified air into which the odorant stimulus is injected to further reduce fluctuation in volume flow rate with solenoid activation; and 4) a flow dilution system to control stimulus concentration and humidity.

This system introduces a constant airflow into the nostril via a cannula which is inserted through the naris. The subject breathes through the mouth, so that the airflow containing the odorants is not disturbed. Besides the odor, there are no other cues such as sound, pressure change, or humidity change to indicate the onset of a stimulus. Measured at the cannula tip, the stimulus has a rise time of about 50 msec (½ height response).

OdorJet Stimulus

With stimulation by the apparatus according to the present invention, the subject will breathe naturally through the nose, with both nostrils resting on airtubes. During selected inspirations, the odorant dispenser will be activated by the experimenter, producing a discrete "puff" of odorant gas. The trigger pulse will be used to synchronize evoked potential averaging. As with the Constant Flow system of the olfactometer, the apparatus according to the present invention will give the subject no clue (besides odor) when the stimulus has been triggered.

Modeling Airflow and the Stimulus

A model human airway can be used to determine the actual temporal envelopes of the various stimuli generated. By aiming an IR beam across the immediate region of the neuroepithelium (just below the cribiform plate, the "ceiling" of that portion of the airway) the flow of odorant gas across the neuroepithelium region can be directly monitored.

These empirical data will illuminate the basic nature of the olfactory stimuli by demonstrating how the turbulence induced by airflow over the turbinate bones smears and distorts the temporal envelope.

Electrophysiologic Methods

Evoked potentials will be recorded from scalp electrodes according to standard methods (Evans and Starr, 1993 "Stimulus Parameters and Temporal Evolution of the Olfactory Evoked Potential in Rats", *Chemical Senses*, 17: 61–77; Evans, et al., 1995 "Chemosensory (Olfactory) Event-Related Potentials in Normal Human Subjects: Effects of Age and Gender." *Electroencephalography and Clinical Neurophysiology*, 95: 293–301). Electrodes will be placed at $F_z$, $C_z$, $P_z$, T3, T4 and referenced to A1. An eye channel (supraorbital referenced to infraorbital) will be used to register the electro-oculogram (EOG) allowing offline rejection of single trials contaminated by eye movements or blinking. The electroencephalogram will be amplified 20,000 times, bandpass filtered at 0.1–100 Hz and notch filtered at 60 Hz using a Grass® Model 12 Neurodata Acquisition System™. The filtered electroencephalogram will be digitized at a rate of 200 Hz and single trials consisting of 500 data points per channel will be saved in individual data files. The electromagnetic solenoid valves of the olfactometer or the trigger pulse of the apparatus according to the present invention will be used to synchronize signal averaging for averaged evoked potentials.

Peak latencies of the evoked potential components will be calculated from the time of stimulus onset at the nostril to the point of maximum voltage or to a point extrapolated from the intersection of the ascending and descending limbs of a waveform. Peak amplitudes will be defined as the difference between the maximum voltage of a component and the average voltage of the prestimulus baseline. Interpeak amplitudes will be calculated as the difference between the peak amplitudes of two successive components.

fMRI Methods

As with the evoked potential studies, the purpose of the fMRI studies is to determine whether reliable signs of dysfunctional odor sensory processing can be found in patients in the earliest stages of incipient Alzheimer's disease. This search will proceed by comparing normal and early Alzheimer's diseased patients.

Subjects

Participating in this study will be 10 healthy males and females, 60-80 years of age, and 10 males and females diagnosed with Alzheimer's disease based on and the NINCDS-ADRDA criteria and examined at the UC Irvine Alzheimer's Disease Clinic, as described above.

Scan Procedures

MRI is done at 1.5 Tesla using a GE Signa scanner and head coil. Saggital $T_1$, Axial, $T_2$ weighted, and coronal $T_1$ weighted coronal images are clinically evaluated by a radiologist to screen for neuropathology or other abnormalities. The functional MRI experiments will be performed on GE Signa 1.5T scanner, equipped with SMIS head coil and data acquisition system (Surrey Medical Imaging Systems, Surrey, England) which enables the EPI capability.

Anatomical images will be taken to locate the olfactory cortex by using the pulse sequence for $T_1$ weighted 3-D spoiled gradient recalled acquisition sequence (SPGR). Each subject will be scanned for 128, 2.5 mm thick coronal slices acquired at TE=5 ms, TR—24 ms, and flip angle of 30°. Several olfactory processing regions, including pyriform, entorhinal, and hippocampal cortices and the amygdala nuclei will be selected for examination for comparison of normal and Alzheimer's diseased subjects. Functional imaging will be performed by using GE-EPI pulse sequences. With the current setting, 64 k-space lines with 128 frequency encoding steps can be acquired in one data acquisition window from one excitation. The acquired data will be zero-filled to 256×256 points for image reconstruction. The total data acquisition time for each image is less than 200 ms. The functional images will be taken in 21 alternating "off/on, on/off" cycles.

Olfactory stimuli for the functional MRI will be presented with an apparatus according to the present invention that is not sensitive to the magnetic fields generated by the MRI. The scanner room will be free of external distractions, with lights off, and the viewing screen illuminated only when a stimulus is presented. Onset of the olfactory stimulus will be recorded to mark the exact time of presentation and fMRI acquisition. Using the apparatus of the present invention, the fMRI images can be acquired in conditions of no-odor, odor 1 only, odor 2 only.

Data Analysis

Functional images will be analyzed for pixel intensity within identified regions of interest (ROI) using commercially available software packages (such as Analyze and Image & SPDM). Localization of ROIs will be facilitated by overlaying the functional images on high-resolution, high contrast images acquired to optimize structural identification. ROIs to be examined for stimulation include the primary olfactory cortices (such as pyriform, entorhinal) and areas distal to those structures (hippocampus, amygdala). Control areas that should not increase in activity will also be examined and include corpus callosum and brain stem. Anatomical ROIs are determined from 3D reconstruction of coronal images. To standardize brain position the coronal images are obtained perpendicular to the Sylvian fissure. ROI boundaries based on anatomical landmarks are designated for the olfactory processing regions. All slices containing the ROI are used to determine the volume (mm$^3$). MR images are displayed on a sun Sparkstation with Analyze software for image reconstruction and quantification. Intensity levels for cerebrospinal fluid (CSF), and gray and white matter are determined by sampling multiple areas of the ventricles, cortical mantle and corpus callosum, respectively. Structures in each hemisphere are examined and analyzed independently. Computer assisted area analysis involved the experimenter, unaware of the subject's stimulation condition, drawing the ROI, the image digitized, pixel number and area measurements with appropriate intensity levels automatically counted (Kesslak, J. P., Nalcioglu, O., and Cotman, C. W. (1991)—Quantitation of magnetic resonance scans for hippocampal and paraphippocampal atrophy in Alzheimer's Disease. Neurology, 41: 51–54; and Kesslak, J. P., Nagata, S. F., Lott, I., Nalcioglu, O. (1994)—Magnetic resonance imaging analysis of age related changes in the brains of individuals with Down's syndrome, Neurology, 44: 1039–1045). The ROI's are defined by standardized brain landmarks (Amaral, D. G., Insausti, R. In: Paxinos, G. (1990) ed. "The Human Nervous System". Academic Press; Daniels, D. L., Haughton, V. M., Nadich, T. P. (1987) "Cranial and Spinal Magnetic Resonance Imaging An Atlas and Guide", Raven Press; DeArmond, S. J., Fusco, M. M., Dewey, M. M. (1989) "Structure of the Human Brain: A Photographic Atlas" (3rd Ed.) Oxford University Press; and Duvernoy, H. (1991) "The Human Brain-Surface, Three Dimensional Sectional Anatomy" Springer-Vergag), as previously described (Kesslak, et al., 1991; Kesslak, et al., 1994).

While the present invention has been described with reference to a presently preferred embodiment, it will be appreciated by those of ordinary skill in the art that various modifications, changes, alternatives and variations may be made therein without departing from the spirit and scope thereof as defined in the appended claims.

The invention was made with government support under a grant or contract awarded by the National Institutes of Mental Health. The United States government may have certain rights in this invention.

What is claimed is:

1. Apparatus for micro-dispensation of airborne materials for inhalation or sniffing, comprising:

at least one fluid reservoir;

means for micro-dispensing fluid from said at least one reservoir;

means for generating airborne materials for inhalation or sniffing by a subject; and means for delivering airborne materials for inhalastion or sniffing by said subject wherein said means for delivering said airborne materials selectively delivers said airborne materials to discrete portions of said subject's olfactory epithelium wherein said discrete portions of said subject's olfactory epithelium have a size of 10,000 to 100,000 square microns.

2. Apparatus for micro-dispensation of airborne materials for inhalation or sniffing, comprising:

at least one fluid reservoir;

means for micro-dispensing fluid from said at least one reservoir comprising an ink-jet type dispenser;

means for generating airborne materials from said fluid for inhalation or sniffing by a subject; and means for delivering airborne materials for inhalation or sniffing by said subject wherein said means for delivering said airborne materials delivers said airborne materials to discrete portions of an area selected from the group consisting of said subject's olfactory epithelium and vomeronasal organ wherein said discrete portions have a size off from 10,000 to 100,000 square microns.

3. Apparatus for micro-dispensation of airborne materials for inhalation or sniffing, comprising:

at least one fluid reservoir containing fluid to be dispensed;

a digital micro-dispenser in communication with said at least one fluid reservoir and a controller operably connected to the micro-dispenser and capable of controllably causing the micro-dispenser to dispense discrete micro droplets of said fluid;

a heating wick for generating airborne materials from said fluid for inhalation or sniffing by a subject; and the digital micro-dispenser being positioned to dispense said micro droplets onto the heating wick.

4. Apparatus for micro-dispensing of airborne materials according to claim 3 wherein said digital micro-dispenser is an ink-jet type dispenser.

5. Apparatus for micro-dispensation of airborne materials according to claim 3 or 4 wherein the digital micro-dispenser comprises a transducer selected from the group consisting of piezoelectric, electrostrictive, magnetostrictive and electromechanical transducers.

6. Apparatus for micro-dispensation of airborne materials according to claim 3 or 4 wherein the digital micro-dispenser comprises a thermal ink-jet type dispenser.

7. Apparatus for micro-dispensation of airborne materials according to claim 3 or 4 wherein said digital micro-dispenser is configured to dispense fluid from said at least one fluid reservoir in volumes ranging from approximately 10 to 1,000 picoliters.

8. Apparatus for micro-dispensation of airborne materials according to claim 3 or 4 wherein the fluid contained in said at least one said fluid reservoir comprises a group consisting of drugs, fragrances and substances comprising a volatile component.

9. Apparatus for micro-dispensing of airborne materials according to claim 8 wherein said fluids are dispensed with a fluid vehicle selected from the group consisting of water, ethanol and propylene glycol.

10. Apparatus for micro-dispensation of airborne materials for inhalation or sniffing according to claim 3 or 4 wherein said at least one fluid reservoir is a plurality of fluid reservoirs and said digital micro-dispenser comprises a plurality of micro-dispensers in fluid communication with said plurality of fluid reservoirs and wherein said controller is operably connected to the plurality of micro-dispensers and capable of controllably causing each micro-dispenser to dispense discrete micro-droplets of fluid from one or more of said plurality of fluid reservoirs; and the plurality of digital micro-dispensers are positioned to dispense micro-droplets onto said heating wick.

11. Apparatus for micro-dispensation of airborne materials according to claim 10 wherein the plurality of micro-dispensers comprise at least two ink-jet dispensers positioned in a side-by-side arrangement oriented to dispense said micro-droplets onto a heating wick.

12. Apparatus for micro-dispensation of airborne materials according to claim 10 wherein the plurality of micro-dispensers comprise a plurality of ink-jet type dispensers arranged in a radial orientation to dispense said microroplets onto a heating wick.

13. Apparatus for micro-dispensation of airborne materials according to claim 12 wherein said heating wick is a conductive screen.

14. Apparatus for micro-dispensation of airborne materials according to claim 10 wherein said heating wick further comprises a plurality of said heating wicks and whereby the plurality of micro-dispensers are positioned to dispense micro-droplets onto different ones of said plurality of heating wicks.

15. Apparatus for micro-dispensing of airborne materials according claim 10 further including structure for delivering said airborne materials for inhalation or sniffing by said subject.

16. Apparatus for micro-dispensing of airborne materials according to claim 15 wherein said structure delivers said airborne materials to the inspired air or personal air space of said subject.

17. Apparatus for micro-dispensation of airborne materials according to claim 16 wherein the structure that delivers said airborne materials to the subject's inspired air or personal air space comprises virtual reality headgear.

18. Apparatus for micro-dispensation of airborne materials according to claim 15 wherein said structure comprises at least one air flow channel for presenting said airborne materials to said subject's nostrils.

19. Apparatus for micro-dispensation of airborne materials according to claim 16 wherein said structure comprises two air flow channels for presenting said airborne materials to said subject's nostrils.

20. Apparatus for micro-dispensation of airborne materials according to claim 4 wherein said ink-jet dispenser micro-dispenses said fluid at a rate of from 1 to 10,000 drops of fluid per second.

21. Apparatus for micro-dispensation of airborne materials for inhalation or sniffing according to claim 3, comprising:

the at least one fluid reservoir comprises an elongated tube reservoir connected to the digital micro-dispenser wherein said tube is bendable to a form which occupies less space.

22. Apparatus for micro-dispensing of airborne materials for inhalation or sniffing according to claim 21 wherein said elongated tube reservoir is in the form of a coiled tube.

23. Apparatus for micro-dispensation of airborne materials according to claim 22, wherein said coiled tube reservoir is wrapped around at least a portion of the micro-dispenser.

24. Apparatus for micro-dispensation of airborne materials according to claim 3 wherein the controller controlling the digital micro-dispenser is also in control of the heating wick; and said controller controls the temporal envelope of said airborne materials.

25. Apparatus for micro-dispensation of airborne materials according to claim 24 wherein the controller controls the temporal envelope of said airborne materials by controlling the number and rate at which droplets are deposited upon the heating wick.

26. Apparatus for micro-dispensation of airborne materials according to claim 25 wherein the controller controls the temporal envelope of said airborne materials by controlling the operating temperature of the heating wick.

27. Apparatus for micro-dispensation of airborne materials for inhalation or sniffing, comprising:

a plurality of fluid reservoirs containing fluid to be dispensed;

a plurality of digital micro-dispensers comprising an ink-jet type dispenser in communication with said plurality of fluid reservoirs and a controller operably connected to the micro-dispenser and capable of controllably causing the micro-dispenser to dispense discrete micro-droplets of said fluids;

at least one heating wick under control of the controller for generating airborne materials from said fluids for inhalation or sniffing by a subject; and the plurality of ink-jet dispensers being positioned to dispense said micro-droplets onto said at least one heating wick.

28. Apparatus for micro-dispensation of airborne materials according to claim 27 further including at least one droplet of a fluid micro-dispensed from said plurality of reservoirs by said ink-jet dispenser onto the heating wick to generate a puff of airborne materials for inhalation or sniffing.

29. Apparatus for micro-dispensing of airborne materials according to claim 27 further including a plurality of droplets of a fluid micro-dispensed by said ink-jet from said plurality of reservoirs onto the at least one heating wick to generate a puff of airborne materials for inhalation or sniffing.

30. Apparatus for micro-dispensation of airborne materials according to claim 27 further including at least one droplet of a plurality of fluids micro-dispensed from said plurality of reservoirs by said ink-jet dispenser onto said heater to generate a puff of airborne material for inhalation or sniffing.

31. Apparatus for micro-dispensation of airborne materials according to claim 27 further including a plurality of droplets of a plurality of fluids micro-dispensed by said ink-jet from said plurality of reservoirs to generate a puff of airborne materials for inhalation or sniffing.

32. Apparatus for micro-dispensing of airborne of vapor for inhalation or sniffing, comprising:
 a chip comprising a multiplicity of individual fluid reservoirs having fluid disposed therein;
 heating elements in contact with the fluid in the individual fluid reservoirs capable of vaporizing fluid disposed in said individual fluid reservoirs;
 a digital programmable controller capable of generating airborne materials from the fluid in the reservoirs by activating the heating elements for inhalation or sniffing of the airborne vapors by s subject; and
 wherein said chip is provided with a cover for encapsulating the fluids within each said reservoir until the activation of the heating elements.

33. Apparatus for micro-dispensing of airborne materials according to claim 32, wherein:
 the fluid in the individual fluid reservoirs is the same fluid selected from the group consisting of drugs, fragrances and substances comprising a volatile component.

34. Apparatus for micro-dispensing of airborne materials according to claim 33, wherein:
 the same fluid is contained in plurality of different reservoirs at different concentrations of the same substance whereby different concentrations of airborne materials may be generated by selection of particular reservoirs having different concentrations of said fluid.

35. Apparatus for the micro-dispensing of airborne materials for inhalation or sniffing according to claim 32, wherein the digital programmable controller is capable of generating combined airborne vapor materials from said fluid by activating two or more of the heating elements at the same time.

36. Apparatus for micro-dispensation of airborne vapors according to claim 32 further including a puff of vapor from at least one of fluids in the reservoirs upon activation of a heating element.

37. Apparatus for micro-dispensation of airborne materials for inhalation or sniffing, comprising:
 a chip comprising a multiplicity of individual fluid reservoirs, each of said reservoirs having a first fluid and a second fluid therein;
 heating elements in contact with the first fluid in the individual fluid reservoirs;
 a digital programmable controller capable of generating airborne materials from the fluid in the reservoirs by activating the heating elements; and
 the first fluid and the second fluid being ejected upon vaporization of the first fluid when the heating elements are activated.

38. Apparatus for micro-dispensation of airborne materials according to claim 37 further including a heating wick positioned to receive second fluid upon ejection of second fluid from the reservoir by first fluid; and
 wherein said second fluid is converted to vapor upon contacting said heating wick.

39. A method for micro-dispensation of airborne material, comprising the steps of:
 providing a digital dispenser for micro-dispensing discrete droplets of fluid;
 providing at least one heating wick for generating airborne materials from fluid deposited thereon;
 heating the wick to a selected temperature above ambient temperature; and
 depositing at least one individual droplet of said fluid by operating said micro-dispenser upon the at least one heated wick to generate airborne materials from said fluid for inhalation or sniffing by a subject.

40. A method for micro-dispensation of airborne materials according to claim 39, comprising the steps of:
 wherein the step of depositing at least one individual droplet of said fluid comprises depositing fluid selected from a group consisting of drugs, fragrances, and substances comprising a volatile component.

41. A method for micro-dispensation of airborne materials according to claim 39, comprising the steps of:
 further including the step of delivering said airborne materials for inhalation or sniffing to a subject.

42. A method for micro-dispensation of airborne materials according to claim 41 wherein the step of delivering said airborne materials for inhalation or sniffing to said subject comprises the step of moving said airborne materials through at least one air flow channel for presenting said airborne materials to said subject's nostrils.

43. A method for micro-dispensation of airborne materials according to claim 39, further including the step of controlling the temporal envelope of the airborne materials by adjusting the temperature of the heating wick.

44. A method for micro-dispensation of airborne materials according to claim 43, wherein the temporal envelope of said airborne materials is further adjusted by the step of controlling the number and rate at which droplets are deposited upon the heated wick.

45. A method for micro-dispensation of airborne materials according to claim 39, further including the step of sensing the generated volatilized airborne material by means of an electronic sensor.

46. A method for micro-dispensation of airborne material, comprising the steps of:
 providing a digital dispenser for micro-dispensing discrete droplets of fluid;
 providing a fluid supply to the digital micro-dispenser;
 providing a heating wick which can be operated at variable temperatures; and
 depositing one or more individual droplets of said fluid from said micro-dispenser upon said heated wick at a selected temperature which controls rise time and amplitude of a fluid vapor puff produced from said fluid droplets impacting said heating wick;
 whereby a temporal envelope of fluid vapor puffs is controlled by controlling the temperature of the wick.

* * * * *